(12) United States Patent
Yamanaka et al.

(10) Patent No.: US 8,951,801 B2
(45) Date of Patent: Feb. 10, 2015

(54) METHOD FOR MAKING IPS CELLS

(75) Inventors: Shinya Yamanaka, Kyoto (JP); Naoki Goshima, Tokyo (JP); Momoko Maekawa, Kyoto (JP); Yoshifumi Kawamura, Tokyo (JP); Hiromi Mochizuki, Tokyo (JP)

(73) Assignees: Kyoto University, Kyoto (JP); National Institute of Advanced Industrial Science and Technology, Tokyo (JP); Japan Biological Informatics Consortium, Tokyo (JP)

( * ) Notice: Subject to any disclaimer, the term of this patent is extended or adjusted under 35 U.S.C. 154(b) by 57 days.

(21) Appl. No.: 13/203,735

(22) PCT Filed: Feb. 19, 2010

(86) PCT No.: PCT/JP2010/053024
§ 371 (c)(1),
(2), (4) Date: Nov. 14, 2011

(87) PCT Pub. No.: WO2010/098419
PCT Pub. Date: Sep. 2, 2010

(65) Prior Publication Data
US 2012/0052583 A1 Mar. 1, 2012

Related U.S. Application Data

(60) Provisional application No. 61/208,853, filed on Feb. 27, 2009, provisional application No. 61/276,123, filed on Sep. 8, 2009.

(51) Int. Cl.
*C12N 15/00* (2006.01)
*C07H 21/02* (2006.01)
*C07H 21/04* (2006.01)

(52) U.S. Cl.
USPC ............. 435/455; 530/350; 536/23.1

(58) Field of Classification Search
USPC ............. 435/325, 455; 530/350; 536/23.1
See application file for complete search history.

(56) References Cited

U.S. PATENT DOCUMENTS

| 2009/0068742 A1 | 3/2009 | Yamanaka |
| 2011/0231944 A1 | 9/2011 | Watarai et al. |
| 2011/0236362 A1 | 9/2011 | Watarai et al. |
| 2013/0029423 A1 | 1/2013 | Yamanaka et al. |

FOREIGN PATENT DOCUMENTS

| CN | 101613717 A | 12/2009 |
| EP | 1970446 A1 * | 12/2006 |
| EP | 2 096 169 A1 | 9/2009 |
| WO | WO 2007/069666 A1 | 6/2007 |
| WO | WO 2008/118820 A2 | 10/2008 |
| WO | WO 2009/057831 A1 | 5/2009 |
| WO | WO 2010/027062 A1 | 3/2010 |
| WO | WO 2010/027094 A1 | 3/2010 |
| WO | WO 2010/098419 A1 | 9/2010 |
| WO | WO 2011/016588 A1 | 2/2011 |

OTHER PUBLICATIONS

Takahashi (Cell, 2006, vol. 126:663-676).*
Okita (Nature, 2007, vol. 448, p. 313-317).*
Wernig (Nature, 2007, vol. 448, p. 318-324).*
Yu (Science, 2007, vol. 318, p. 1917-1920).*
Meissner (Nature Biotechnology, 2007, vol. 25: 1177-1181).*
Blelloch (Cell Stem Cell, 2007, vol. 1, p. 245-247).*
Brambrink (Cell Stem Cell, Feb. 7, 2008, vol. 2, No. 2, p. 151-159).*
Aoi (Science, Aug. 1, 2008, vol. 321, No. 5889, p. 699-702, available online Feb. 14, 2008).*
Nakagawa (Nat Biotechnol, 2008, vol. 26: 101-106).*
Wernig (Cell Stem Cell, 2008, vol. 2:10-12).*
Lyssiotis (PNAS, Jun. 2, 2009, vol. 106, No. 22, p. 8912-8917).*
Mandayam (Histol. Histopathol. Oct. 2009, vol. 24, No. 10, p. 1343-13535).*
Heng (Cell Stem Cell, Feb. 2010, vol. 6, No. 2, p. 167-174).*
Feng (Cell Stem Cell, Apr. 3, 2009, vol. 4, p. 301-312).*
Database DDBJ/EMBL/GenBank [online], Accession No. NM_024335, "*Homo sapiens* Iroquois homeobox protein 6 (IRX6), mRNA" (Feb. 19, 2004).
Feng et al., *Nature Cell Biology*, 11(2): 197-203 (2009).
Guo et al., *Development*, 136: 1063-1069 (2009).
Hanna et al., *Cell*, 133(2): 250-264 (2008).
Heng et al., *Cell Stem Cell*, 6(2): 167-174 (2010).
Huangfu et al., *Nature Biotechnology*, 26(11): 1269-1275 (2008).
Jiang et al., *Nature Cell Biology*, 10: 353-360 (2008).
Kim et al., *Journal of Biological Chemistry*, 277(34): 30901-30913 (2002).
Kim et al., *Nature*, 454: 646-650 (2008).
Liao et al., *Cell Research*: 18: 600-603 (2008).
Lyssiotis et al., *Proc. Natl. Acad. Sci. USA*, 106(22): 8912-8917 (2009).
Mali et al., *Stem Cells*, 26: 1998-2005 (2008).

(Continued)

*Primary Examiner* — Michael C. Wilson
(74) *Attorney, Agent, or Firm* — Leydig, Voit & Mayer, Ltd.

(57) ABSTRACT

Reprogramming substances capable of substituting for Klf4, selected from the group consisting of members of the IRX family (e.g., IRX6), members of the GLIS family (e.g., GLIS1), members of the PTX family (e.g., PITX2), DMRTB1, and nucleic acids that encode the same, are provided. Also provided are a method of producing iPS cells, comprising the step of introducing into a somatic cell both one or more kinds of the above-described nuclear reprogramming substances and a substance capable of inducing iPS cells from a somatic cell when combined with Klf4. Still also provided are iPS cells comprising an extraneous nucleic acid that encodes any one of the above-described nuclear reprogramming substances, that can be obtained by the method, and a method of producing somatic cells by inducing the iPS cells to differentiate.

16 Claims, 29 Drawing Sheets
(18 of 29 Drawing Sheet(s) Filed in Color)

(56) References Cited

OTHER PUBLICATIONS

Markoulaki et al., *Nature Biotechnology*, 27(2): 169-171 (2009).
McConnell, et al., *Bioassays*, 29: 549-557 (2007).
Nakagawa et al., *Nature Biotechnology*, 26(1): 101-106 (2008).
Nakatake et al., *Molecular Cellular Biology*, 26(20): 7772-7782 (2006).
Nandan et al., *Histol Histopathol.*, 24(10): 1343-1355 (2009).
Okita et al., *Nature*, 448: 313-317 (2007).
Ottolenghi et al., *Genomics*, 79(3): 333-343 (2002).
Park et al., *Nature*, 451: 141-146 (2008).
Semina et al., *Nature Genetics*, 14(4): 392-399 (1996).
Shi et al., *Cell Stem Cell*, 2: 525-528 (2008).
Takahashi et al., *Cell*, 126: 663-676 (2006).
Takahashi et al., *Cell*, 131: 861-872 (2007).
Takeuchi et al., *Gene Expression Patterns*, 7(1-2): 51-56 (2006).
Yu et al., *Science*, 318: 1917-1920 (2007).
Zardo et al., *Leukemia*, 22(8): 1503-1518 (2008).
European Patent Office, Supplementary European Search Report in European Patent Application No. EP 10 74 6298 (Jul. 31, 2012).
Japanese Patent Office, International Search Report in International Patent Application No. PCT/JP2010/053034 (May 25, 2010), English translation.
Kim et al., *Cell*, 136: 411-419 (2009).
Maherali et al., *Cell Stem Cell*, 1: 55-70 (2007).
Nakagawa et al., *Proc. Natl. Acad. Sci. USA*, 107(32): 14152-14157 (2010).
Zhao et al., *Cell Stem Cell*, 3: 475-479 (2008).
Japanese Patent Office, International Search Report in International Patent Application No. PCT/JP2010/053874 (May 31, 2011) English translation.
Aruga, *Mol. Cell. Neurosci.*, 26(2): 205-221 (2004).
Maekawa et al., *Nature*, 474(7350): 225-229 and supplementary information pp. 1-19 (2011).
Sabiosciences: "Induced Pluripotent Stem Cells —Quick Facts", Technical Notes (Jan. 1, 2009) [retrieved on Apr. 17, 2013, from the Internet at http://sabiosciences.com/manuals/iPSCstemCELLS.pdf].
European Patent Office, European Search Report in European Patent Application No. 13 15 8495 (May 17, 2013).
Kim et al., *The Journal of Biological Chemistry*, 277(34): 30901-30913 (2002).
European Patent Office, Extended European Search Report in European Patent Application No. 11744817.5 (Dec. 13, 2013).
Bernhardt et al., *Biotechnology Journal*, 7(6): 810-821 (2012).
Bosnali et al., *Biol. Chem.*, 389: 851-861 (2008).
Heng et al., *Biomedicine and Pharmacotherapy*, 59: 132-134 (2005).
Heng et al., *Cell Tissue Res.*, 321: 147-150 (2005).
Mitrovic, *Medicine and Biology*, 10(3): 101-105 (2003).
Morrison et al., *Developmental Dynamics*, 236: 481-488 (2007).
National Institutes of Health, "1:the Stem Cell," in *Stem Cells: Scientific Progress and Future Research Directions*, pp. 1-4 (Jun. 2001).
Schmidt et al., *Genome Biology*, 13(10): 251-262 (2012).
Thomson et al., *Proc. Natl. Acad. Sci. USA*, 92: 7844-7848 (1995).
Yee, *Nature Education*, 3(9): 25 (2010) (as retrieved from http://www.nature.com/scitable/topicpage/turning-somatic-cells-into-pluripotent-stem-cells-14431451 on Mar. 27, 2014).
European Patent Office, Extended European Search Report in European Patent Application No. 13 15 8495 (Feb. 3, 2014).
Djuric et al., *Stem Cell Research & Therapy*, 1: 3 [doi:10.1186/scrt3] (2010).
Chinese Patent Office, First Office Action in Chinese Patent Application No. 201180009618.9 (Jul. 18, 2013), English translation.

* cited by examiner

METHOD FOR MAKING IPS CELLS

CROSS-REFERENCE TO RELATED APPLICATIONS

This patent application is the U.S. national phase of International Patent Application No. PCT/JP2010/053024, filed on Feb. 19, 2010, which claims the benefit of U.S. Provisional Patent Application Nos. 61/276,123, filed on Sep. 8, 2009, and 61/208,853, filed on Feb. 27, 2009.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 96,658 bytes ASCII (Text) file named "708871SequenceListing.txt," created Aug. 26, 2011.

TECHNICAL FIELD OF THE INVENTION

The present invention relates to a novel nuclear reprogramming substance and use thereof, more specifically to a novel nuclear reprogramming substance that can substitute for Klf4, and a method of establishing induced pluripotent stem (hereinafter referred to as iPS) cells using the same.

BACKGROUND OF THE INVENTION

In recent years, mouse and human iPS cells have been established one after another. Yamanaka et al. identified genes expressed specifically in pluripotent cells such as ES cells and germ cells by analyzing the EST database, and conducted functional analyses using the knockout mouse technique and the like. Taking into consideration some reports by other research groups, they selected 24 genes as candidate substances that induce pluripotency (reprogram the nucleus) in somatic cells [WO 2007/069666 A1; Takahashi, K. and Yamanaka, S., Cell, 126: 663-676 (2006)]. They induced iPS cells by introducing these 24 genes into fibroblasts (MEF) from a reporter mouse wherein the neomycin resistance gene is knocked-in into the Fbx15 locus and forcing the cells to express these genes, by means of retrovirus. They proceeded to narrow the coverage of the genes that are most important to nuclear reprogramming by transferring 23 out of the 24 genes, and eventually identified the four genes Oct3/4, Sox2, Klf4 and c-Myc as essential factors for nuclear reprogramming in somatic cells [WO 2007/069666 A1; Takahashi, K. and Yamanaka, S., Cell, 126: 663-676 (2006)].

In addition, Yamanaka et al. succeeded in establishing iPS cells (Nanog iPS cells) that show almost the same gene expression and epigenetic modification profiles as those in embryonic stem (ES) cells and preparing a chimeric mouse, by producing a transgenic mouse wherein the green fluorescent protein (GFP) and puromycin-resistance genes are integrated into the locus of Nanog, whose expression is more localized in pluripotent cells than Fbx15 expression, forcing MEF derived from the mouse to express the above-mentioned four genes, and selecting puromycin-resistant and GFP-positive cells [Okita, K. et al., Nature, 448: 313-317 (2007)]. Thereafter, it was revealed that iPS cells could also be produced with three factors other than the c-Myc gene, which also contributes to the germline of chimeric mouse [Nakagawa, M. et al., Nat. Biotechnol., 26: 101-106 (2008)].

Furthermore, Yamanaka et al. succeeded in establishing iPS cells by introducing the same four genes or three genes as those used in the mouse into human skin fibroblasts [WO 2007/069666 A1; Takahashi, K. et al., Cell, 131: 861-872 (2007)]. Hence, it has been demonstrated that iPS cells comparable to ES cells in terms of pluripotency can be produced in both humans and mice, by introducing defined factors into somatic cells.

Of the four genes Oct3/4, Sox2, Klf4 and c-Myc, Oct3/4 and Sox2 are reportedly essential for maintaining self-renewal and pluripotency of ES cells, and c-Myc has also been reported to be involved in maintaining self-renewal and pluripotency of ES cells. Meanwhile, Klf4 belongs to the family of Krüppel-like factor (Klf), a transcriptional factor that controls various biological processes, including proliferation, differentiation, development, and apoptosis [McConnell, B. B. et al., Bioassays, 29: 549-557 (2007)], but details of its functions remain unclear. Epiblast stem cells (EpiSC) established from the epiblast of post-implantation embryo, unlike ES cells, are incapable of forming a chimeric embryo even when injected into a host blastocyst. In EpiSC, however, Oct3/4 and Sox2 are expressed at levels similar to those in ES cells, whereas the Klf4 gene is expressed at remarkably lower levels. Recently, it was reported that by transferring the Klf4 gene alone into EpiSC, a nature similar to that of ES cells can be acquired [Guo, G. et al., Development, 136: 1063-1069 (2009)].

Since ES cells exhibit no morphological changes even when Klf4 is knocked down by RNAi [Nakatake, Y. et al., Mol. Cell. Biol., 26: 7772-7782 (2006)], however, Klf4 may be unessential to the maintenance of the undifferentiated state of ES cells. Yamanaka et al. hypothesized that the same four genes could be substituted by other genes belonging to the same respective families, and showed that iPS cells could be established even when Klf4 was replaced with Klf1, Klf2 or Klf5 [WO 2007/069666 A1; Nakagawa, M. et al., Nat. Biotethnol., 26: 101-106 (2008)]. A group of Thomson et al. reported that human iPS cells could be generated using Nanog and Lin28 in place of Klf4 and c-Myc [WO 2008/118820 A2; Yu, J. et al., Science, 318: 1917-1920 (2007)]; the function of Klf4 can be thought to have many common aspects compared with Nanog.

When ES cells are treated with retinoic acid to induce their differentiation, not only expression of Klf4, but also expression of Klf2 and Klf5 decrease. Taking note of this fact, Jiang et al. knocked down Klf2, Klf4 and Klf5 simultaneously, and found that differentiation was induced in the ES cells, showing that at least some of the members of the Klf family, such as Klf2 and Klf5, can functionally substitute for Klf4 in ES cells [Jiang, J. et al., Nat. Cell Biol., 10: 353-360 (2008)]. They proceeded to transfer the Klf2 or Klf5 gene, or other transcriptional factors and epigenetic regulatory factor, along with the three genes Oct3/4, Sox2 and c-Myc, into MEF; they confirmed that Klf2 and Klf5 can substitute for Klf4, and found that Esrrb, an orphan nuclear receptor similar to estrogen receptors, is also capable of substituting for Klf4 [Feng, B. et al., Nat. Cell Biol., 11: 197-203 (2009)].

SUMMARY OF THE INVENTION

In finding clinical applications for iPS cells, it is of paramount importance to elucidate all details of the nuclear reprogramming mechanism. To identify unknown nuclear reprogramming substances that can substitute for existing nuclear reprogramming substances of public knowledge is of great significance not only in helping elucidate the nuclear reprogramming mechanism, but also in developing a process for establishing iPS cells best suited for clinical applications. Accordingly, it is an object of the present invention to identify a novel nuclear reprogramming substance, particularly a novel nuclear reprogramming substance that can substitute for Klf4, and provide a novel method of establishing iPS cells using the same.

To accomplish the object, the present inventors performed comprehensive gene analysis that can be used to establish iPS cells as substitutes for Klf4, out of gene libraries not only of genes expressed specifically in pluripotent cells such as ES cells, but also of a broader range of transcriptional factors. As a result, the inventors found that iPS cells can be established efficiently when a gene belonging to the IRX family, a gene belonging to the GLIS family, a gene belonging to the PTX family or the DMRT-like family B with proline-rich C-terminal, 1 (DMRTB1) gene, along with the three genes Oct3/4, Sox2 and c-Myc, is transferred into adult mouse skin fibroblasts or MEF, identified these transcriptional factors as novel nuclear reprogramming substances that can functionally substitute for Klf4, and developed the present invention.

Accordingly, the present invention provides the following:

[1] A method of producing iPS cells, comprising the step of transferring into a somatic cell the following (1) and (2):
(1) one or more kinds of substances selected from the group consisting of members of the IRX family, members of the GLIS family, members of the PTX family, DMRTB1, and nucleic acids that encode the same,
(2) a substance capable of inducing iPS cells from a somatic cell when combined with Klf4.
[2] The method according to [1] above, wherein the substances mentioned in (1) above include at least one kind of substance selected from the group consisting of iroquois homeobox protein 6 (IRX6), GLIS family zinc finger 1 (GLIS1), paired-like homeodomain transcription factor 2 isoform b (PITX2), DMRTB1 and nucleic acids that encode the same.
[3] The method according to [1] above, wherein the substance mentioned in (2) above is selected from the group consisting of members of the Oct family, members of the Sox family, members of the Myc family, the Nanog and Lin families, and nucleic acids that encode the same.
[4] The method according to [1] above, wherein the substance mentioned in (2) above is Oct3/4.
[5] The method according to [1] above, wherein the substance mentioned in (2) above is Oct3/4 and Sox2.
[6] The method according to [1] above, wherein the substance mentioned in (2) above is Oct3/4 and c-Myc.
[7] The method according to [1] above, wherein the substance mentioned in (2) above is Oct3/4, Sox2 and c-Myc.
[8] An inducer of iPS cells from a somatic cell, comprising the following (1) and (2):
(1) one or more kinds of substances selected from the group consisting of members of the IRX family, members of the GLIS family, members of the PTX family, DMRTB1, and nucleic acids that encode the same,
(2) a substance capable of inducing iPS cells from a somatic cell when combined with Klf4.
[9] The inducer according to [8] above, wherein the substances mentioned in (1) above include at least one kind of substance selected from the group consisting of IRX6, GLIS1, PITX2, DMRTB1 and nucleic acids that encode the same.
[10] An iPS cell containing an extraneous nucleic acid that encodes one or more kinds of factors selected from the group consisting of members of the IRX family, members of the GLIS family, members of the PTX family and DMRTB1.
[11] The iPS cell according to [10] above, containing an extraneous nucleic acid that encodes one or more kinds of factors selected from the group consisting of IRX6, GLIS1, PITX2 and DMRTB1.
[12] The iPS cell according to [10] above, wherein the at least one kind of extraneous nucleic acid is integrated in the genome.
[13] A method of producing somatic cells, comprising treating the iPS cell according to [10] above to induce the differentiation thereof into somatic cells.
[14] An inducer of iPS cells from a somatic cell, comprising one or more kinds of substances selected from the group consisting of members of the IRX family, members of the GLIS family, members of the PTX family, DMRTB1, and nucleic acids that encode the same, wherein the inducer is transferred into a somatic cell, along with a substance capable of inducing iPS cells from a somatic cell when combined with Klf4.
[15] A use of one or more kinds of substances selected from the group consisting of members of the IRX family, members of the GLIS family, members of the PTX family, DMRTB1, and nucleic acids that encode the same, for producing iPS cells, wherein the substance(s) is transferred into a somatic cell, along with a substance capable of inducing iPS cells from a somatic cell when combined with Klf4.
[16] A substance selected from the group consisting of members of the IRX family, members of the GLIS family, members of the PTX family, DMRTB1, and nucleic acids that encode the same, as an inducer of iPS cells from a somatic cell, wherein the substance is transferred into a somatic cell, along with a substance capable of inducing iPS cells from a somatic cell when combined with Klf4.
[17] A use of the iPS cell according to [10] above in producing somatic cells.
[18] The iPS cell according to [10] above as a source of cells in producing somatic cells.

According to the present invention, it has been shown that members of the IRX family, members of the GLIS family, members of the PTX family and DMRTB1 are capable of functionally substituting for Klf4 in nuclear reprogramming. Investigating the mechanisms of actions of these nuclear reprogramming substances is expected to promote the elucidation of the nuclear reprogramming mechanism. The fact that genes other than those expressed specifically in ES cells have been newly identified as nuclear reprogramming substances by the present invention suggests that other nuclear reprogramming substances that are now unknown will be found in the future.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(PITX2) into Nanog-GFP mouse MEF. P0 shows images taken at the time of colony establishment; P1 shows images for the 1st generation; P2 shows images for the 2nd generation. The photographs of OS+G6, OS+H8, and OS+H10 are as of P0. For each set of three photographs, the left panel shows a GFP-positive colony image, the central panel shows a phase-contrast image, and the right panel shows a superposed photograph of the GFP-positive colony image and phase-contrast image.

Figure 19:
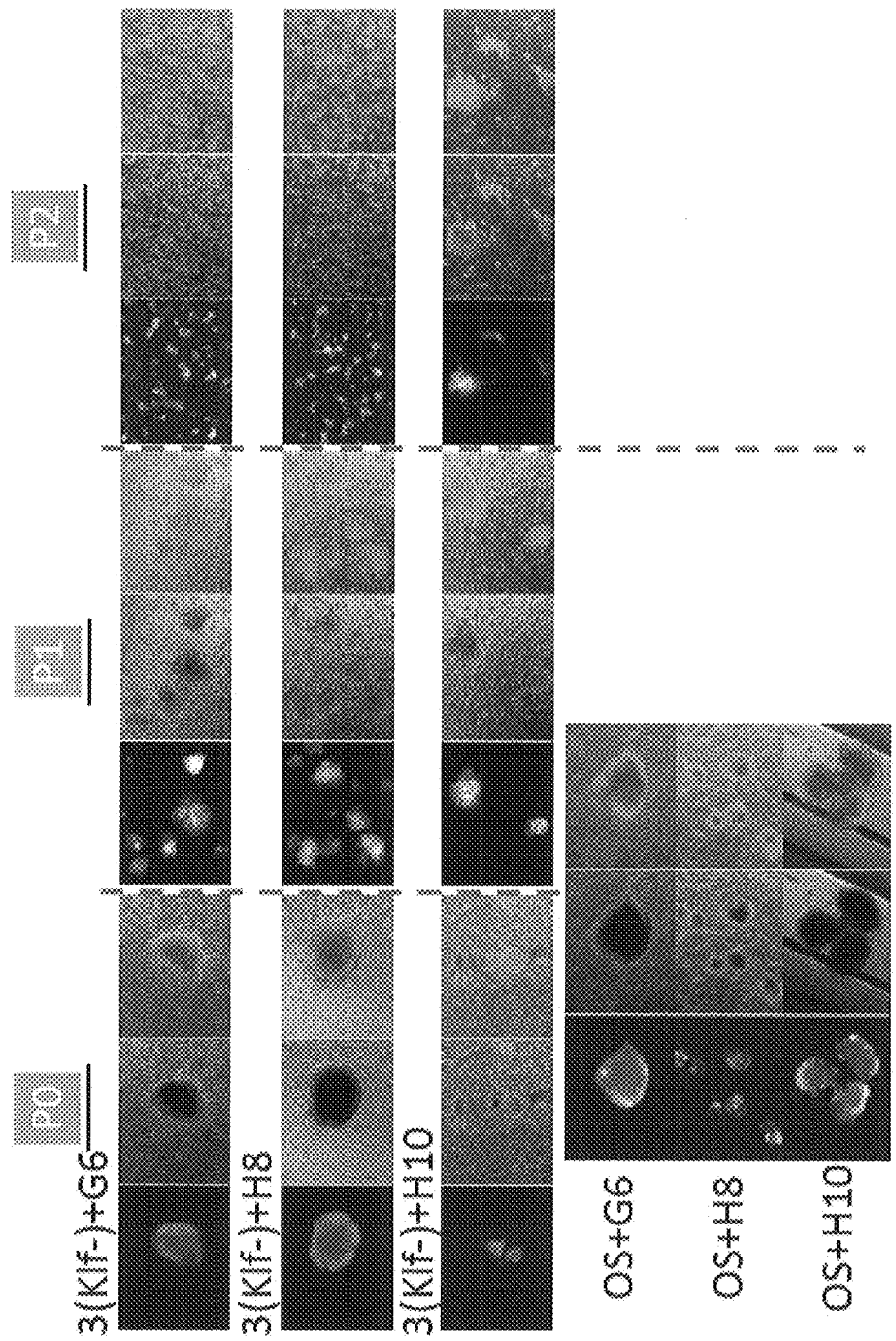
FIG. 19 is a photographic representation of colonies of iPS cells established by transferring a combination of 3 factors (Oct3/4, Sox2, c-Myc) and G6 (GLIS1), H8 (DMRTB1) or H10 (PITX2) into Nanog-GFP mouse MEF, and colonies of iPS cells established by transferring a combination of 2 factors (Oct3/4, Sox2) and G6 (GLIS1), H8 (DMRTB1) or H10
Figure 20:
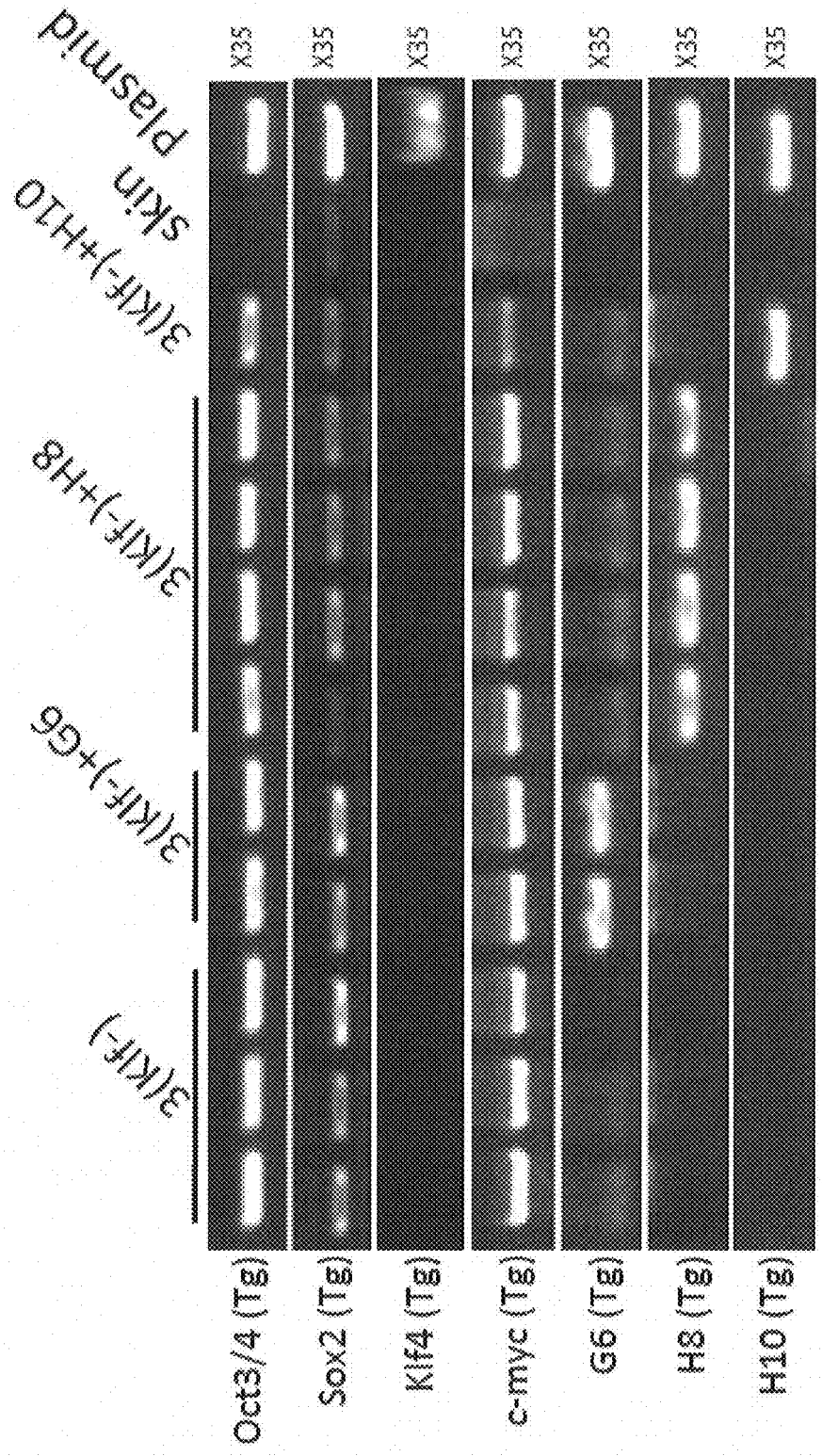

FIG. 20 is a photographic representation of the results of genomic-PCR on the iPS cell clones shown in FIG. 19 (3 factors+G6, H8 or H10). In this figure, "skin" indicates the fibroblast used as a source of somatic cells, and "plasmid" indicates positive controls prepared by amplifying each gene incorporated into pMXs.

Figure 21:
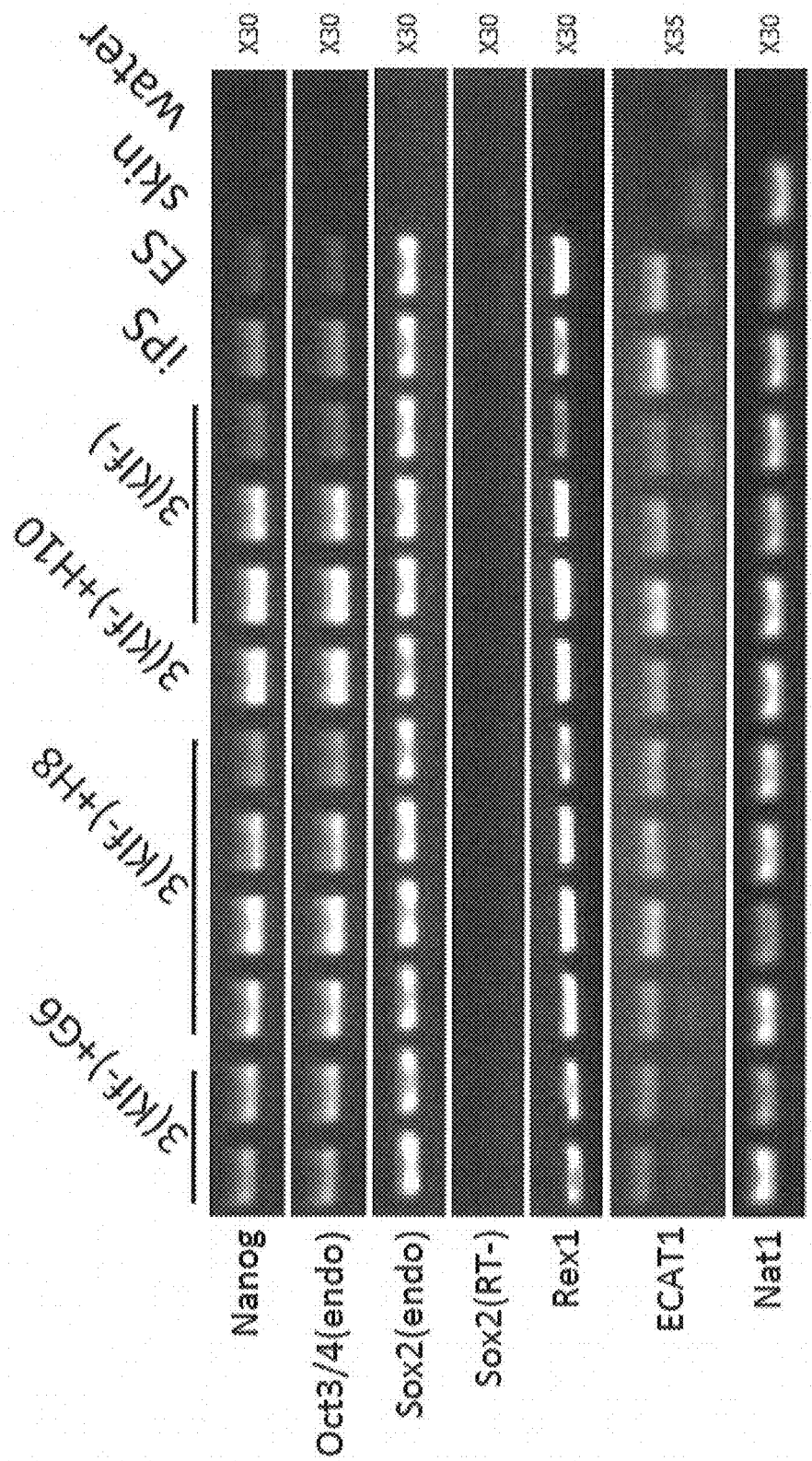

FIG. 21 is a photographic representation of the results of RT-PCR on the iPS cell clones shown in FIG. 19 (3 factors+G6, H8 or H10). In this figure, "skin" indicates the fibroblast used as a source of somatic cells, and "ES" and "iPS" indicate mouse ES cells and iPS cells established using 4 factors (Oct3/4, Sox2, c-Myc, Klf4).

Figure 22:
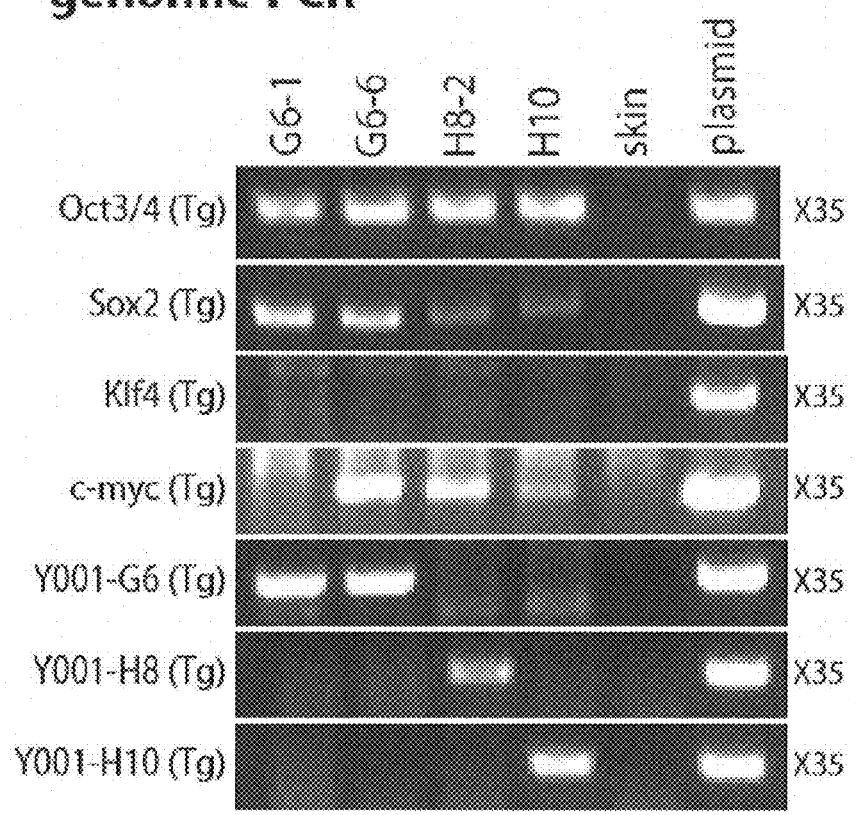

FIG. 22 is a photographic representation of the results of genomic-PCR on teratomas prepared by subcutaneous injection of iPS clones established from adult mouse (Nanog-GFP mouse) skin fibroblasts (G6-1 clone, G6-6 clone, H8-2 clone, H10 clone) into immunodeficient mice. In this figure, "skin" indicates the fibroblast used as a source of somatic cells, and "plasmid" indicates positive controls prepared by amplifying each gene incorporated into pMXs.

Figure 23:
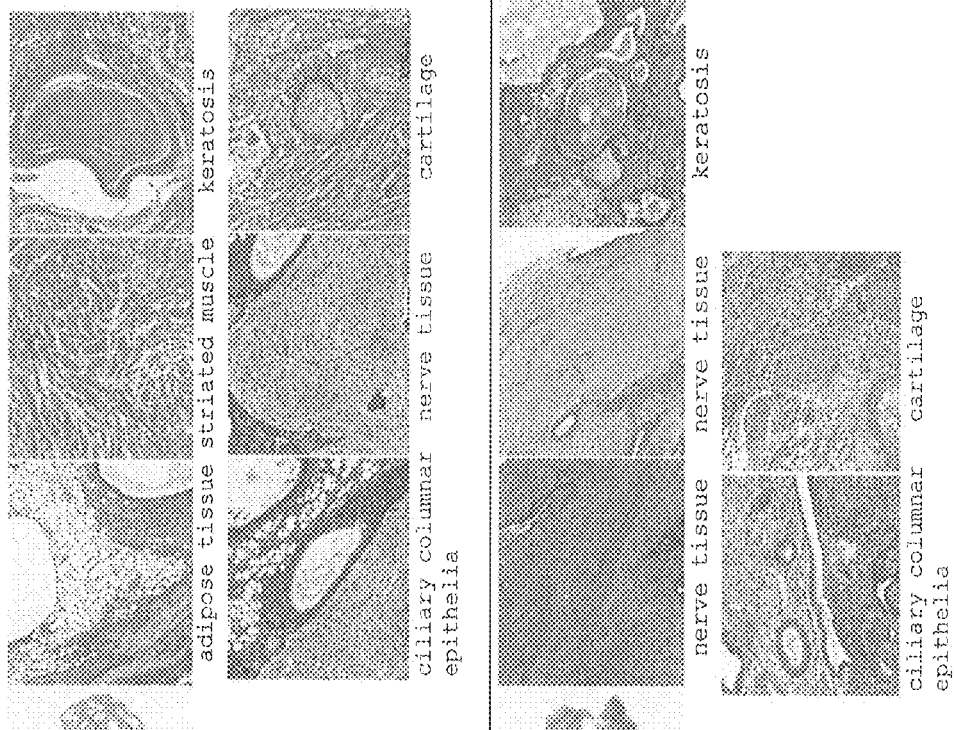

FIG. 23 shows histologically stained images (hematoxylin-eosin stain) of teratomas prepared by subcutaneous injection of G6-1 clone or G6-6 clone into immunodeficient mice.

Figure 24:
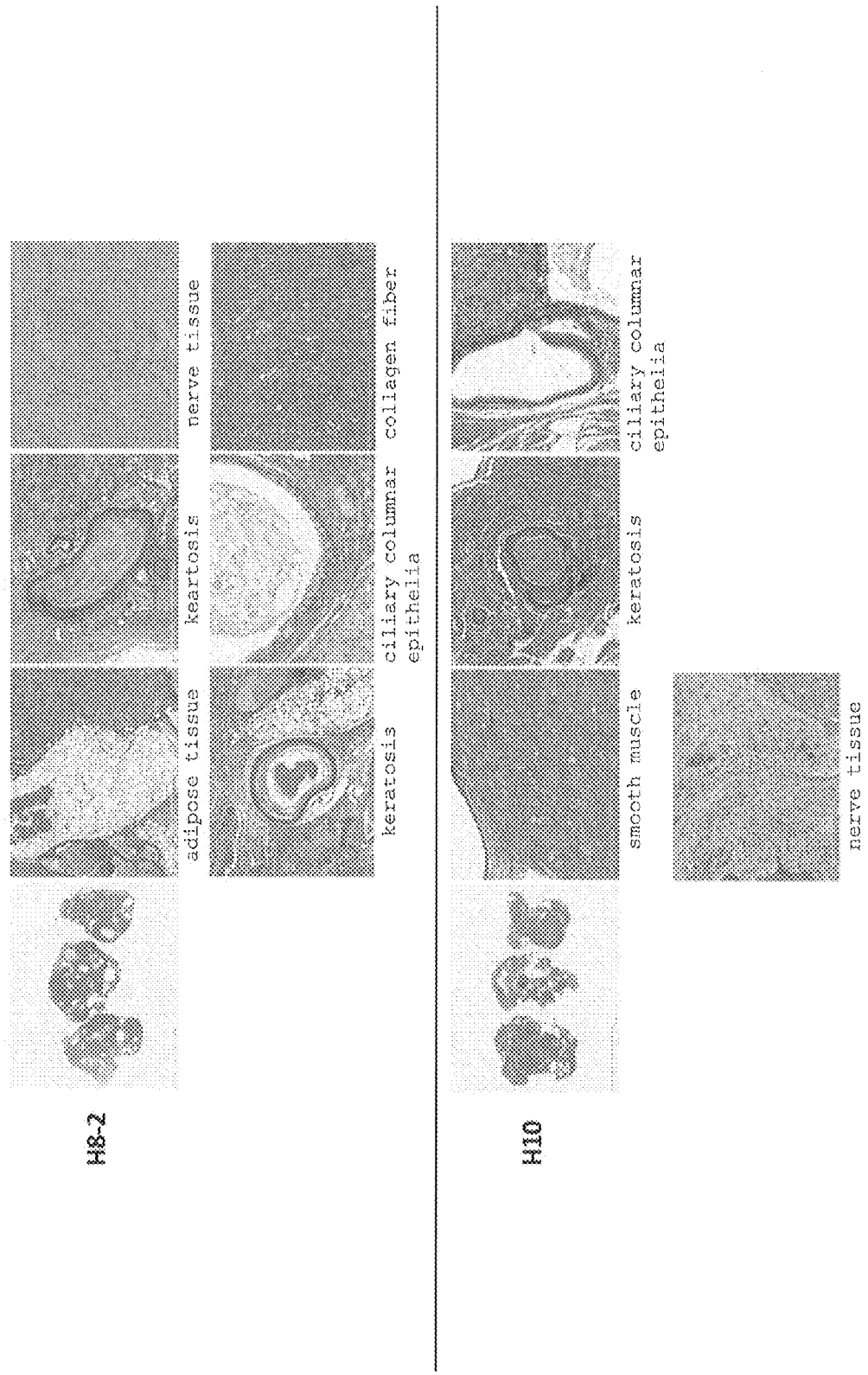

FIG. 24 shows histologically stained images (hematoxylin-eosin stain) of teratomas prepared by subcutaneous injection of H8-2 clone or H10 clone into immunodeficient mice.

Figure 25:
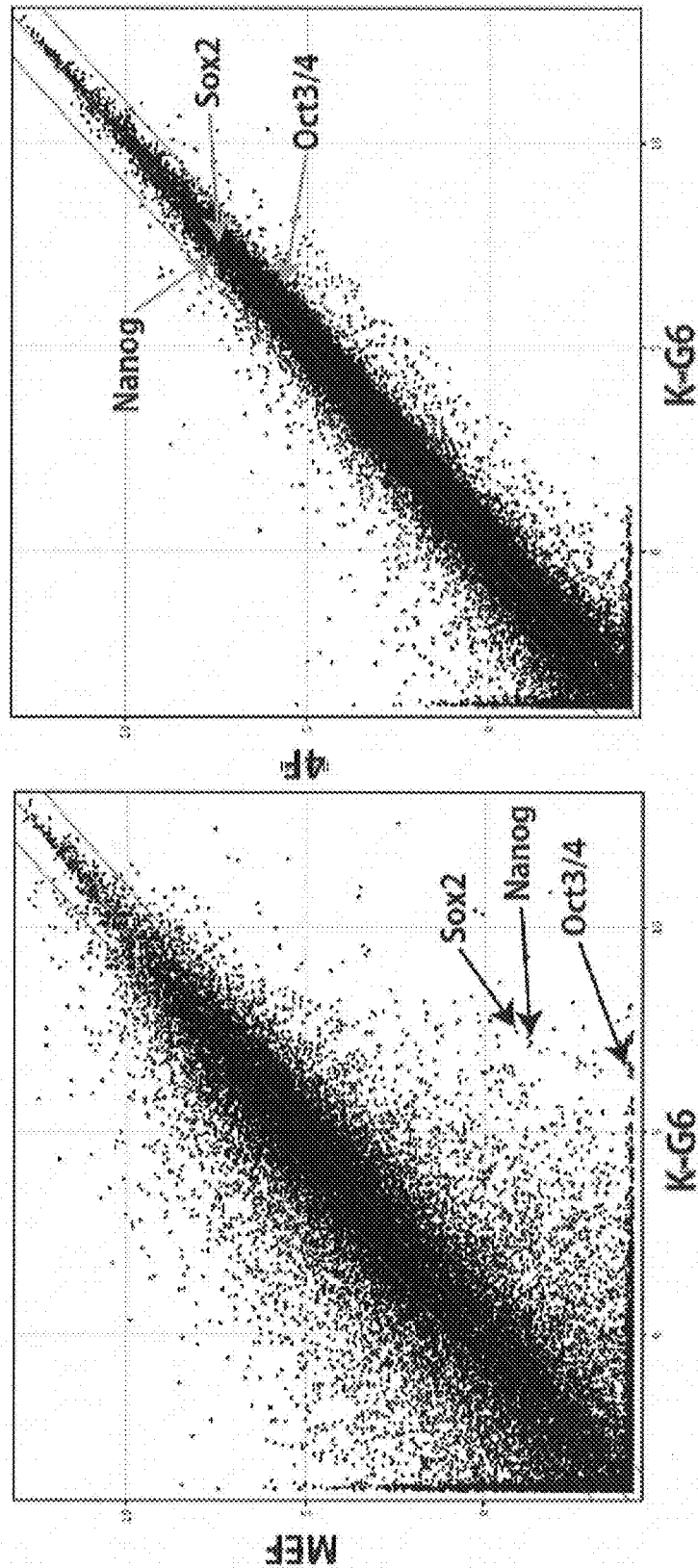

FIG. 25 shows a scatter plot showing the results of DNA microarray analyses performed to determine whether or not a difference in gene expression pattern is present between K-G6 and MEF, or between K-G6 and 4F gene (fold change line: 2-fold).

Figure 26:
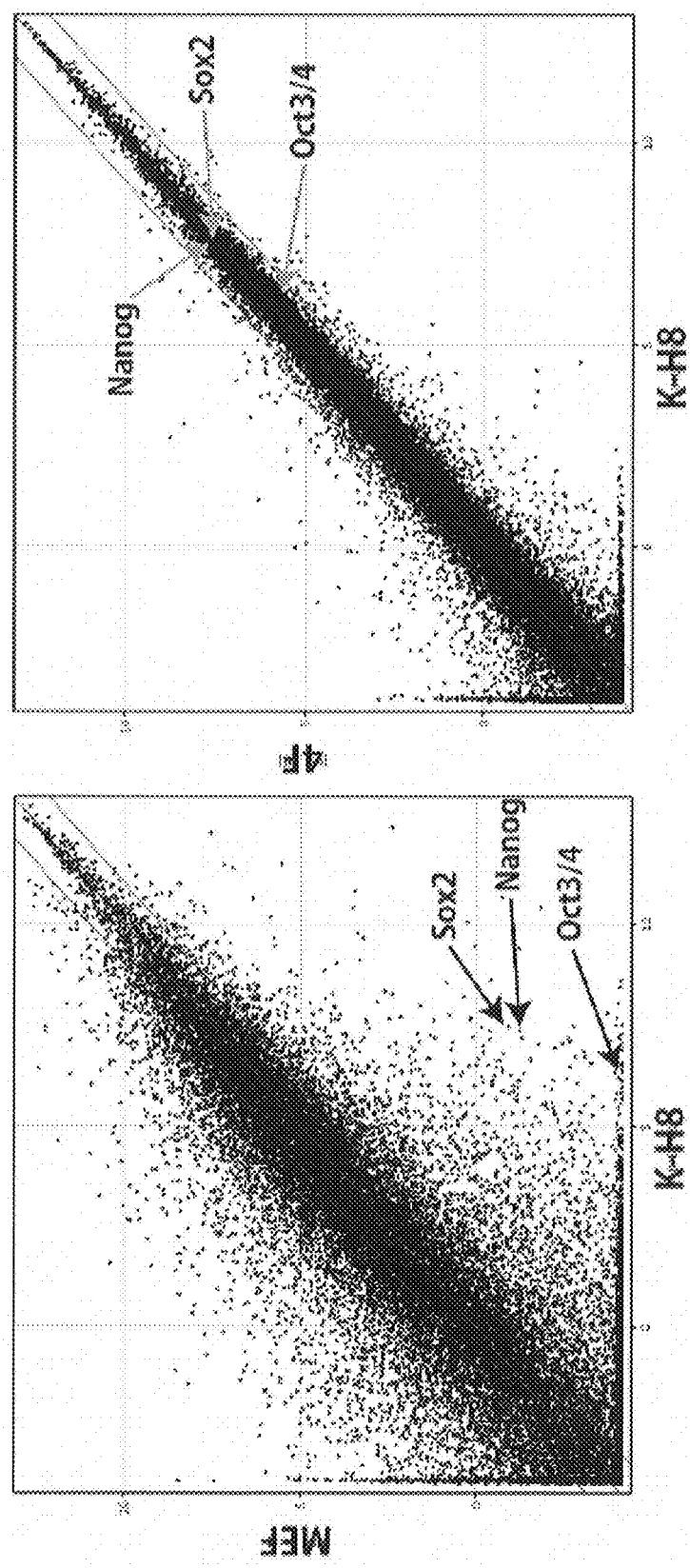

FIG. 26 shows a scatter plot showing the results of DNA microarray analyses performed to determine whether or not a difference in gene expression pattern is present between K-H8 and MEF, or between K-H8 and 4F (fold change line: 2-fold).

Figure 27:
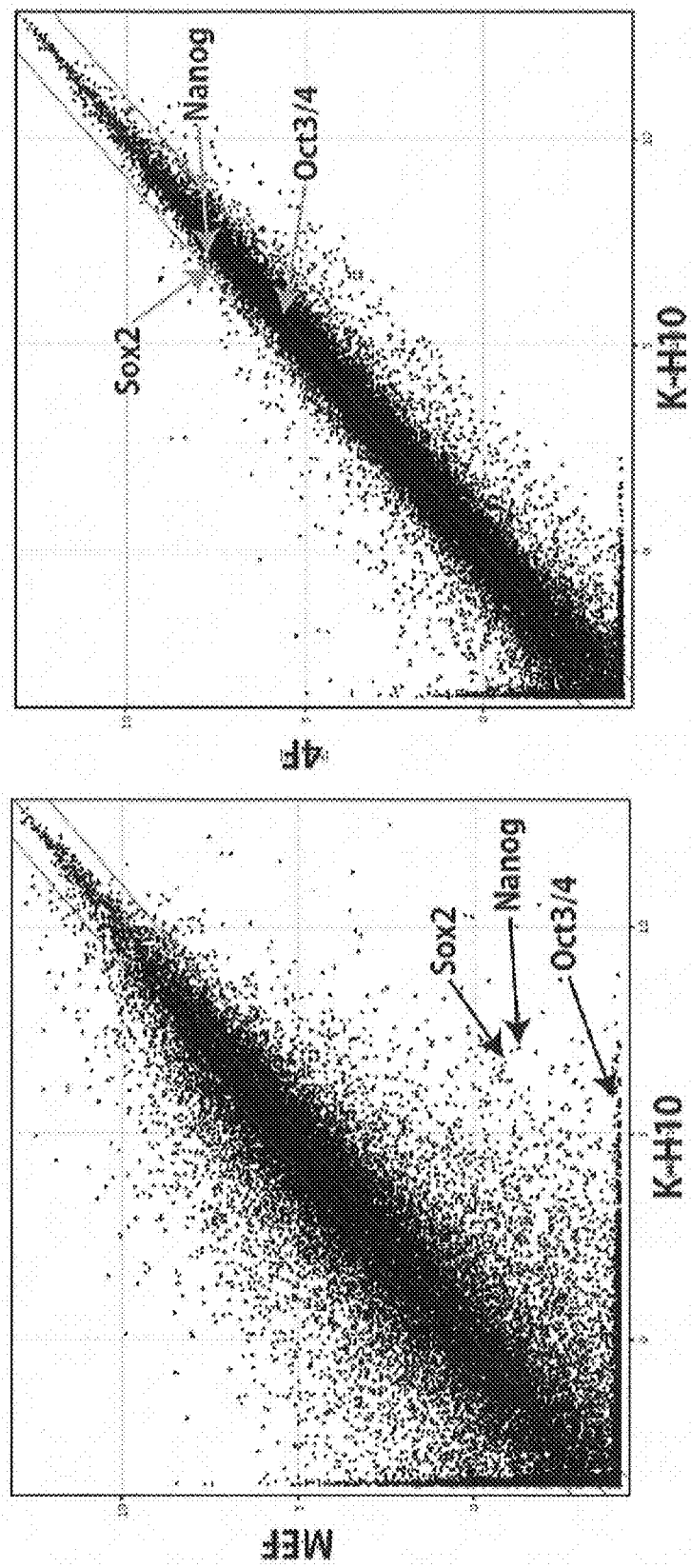

FIG. 27 shows a scatter plot showing the results of DNA microarray analyses performed to determine whether or not a difference in gene expression pattern is present between K-H10 and MEF, or between K-H10 and 4F gene (fold change line: 2-fold).

Figure 28:
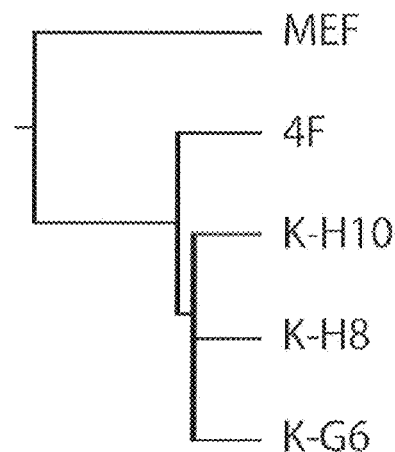

FIG. 28 shows the results of clustering performed on the basis of the correlation coefficient between respective cells.

Figure 29:
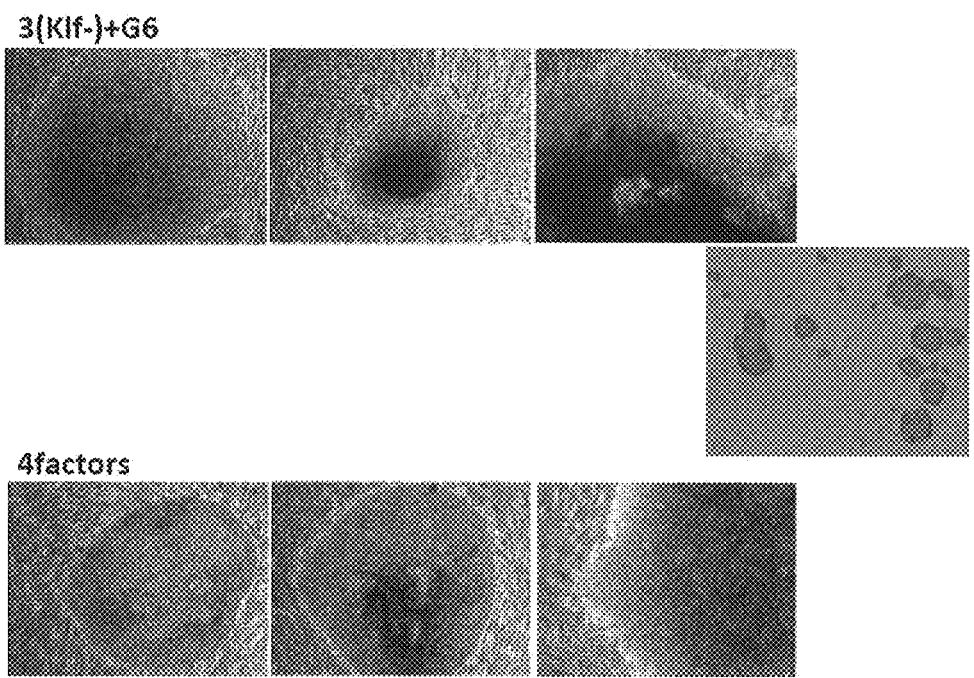

FIG. 29 is a photographic representation of a colony image and alkaline phosphatase stain image of iPS cells established by transferring 3 genes (Oct3/4, Sox2, c-Myc) and G6 (GLIS1) into HDF. For control, a colony image of iPS cells established with 4 genes (Oct3/4, Sox2, c-Myc, Klf4) is also shown.

Figure 30:
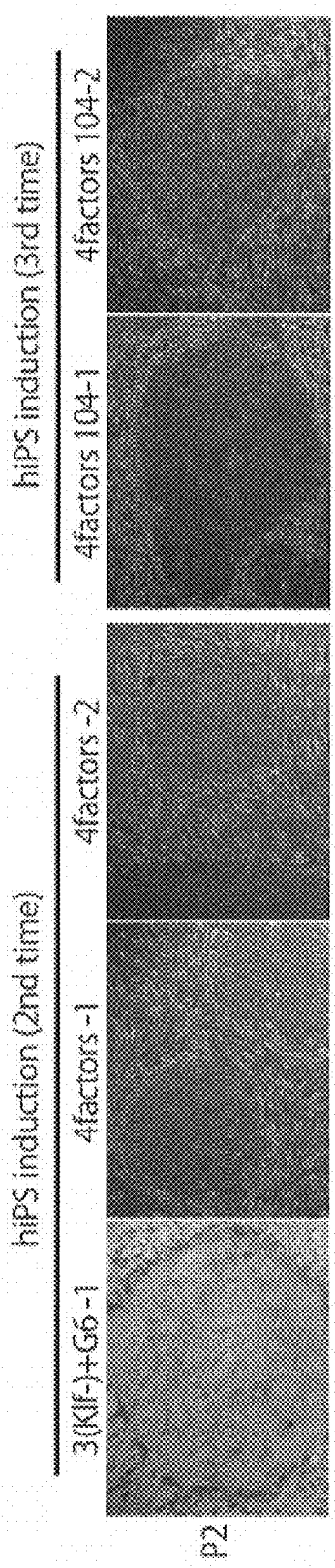

FIG. 30 is a photographic representation of a 2nd-generation colony of iPS cells established by transferring 3 genes (Oct3/4, Sox2, c-Myc) and G6 (GLIS1) into HDF. For control, a colony image of iPS cells established with 4 genes (Oct3/4, Sox2, c-Myc, Klf4) is also shown.

Figure 31:
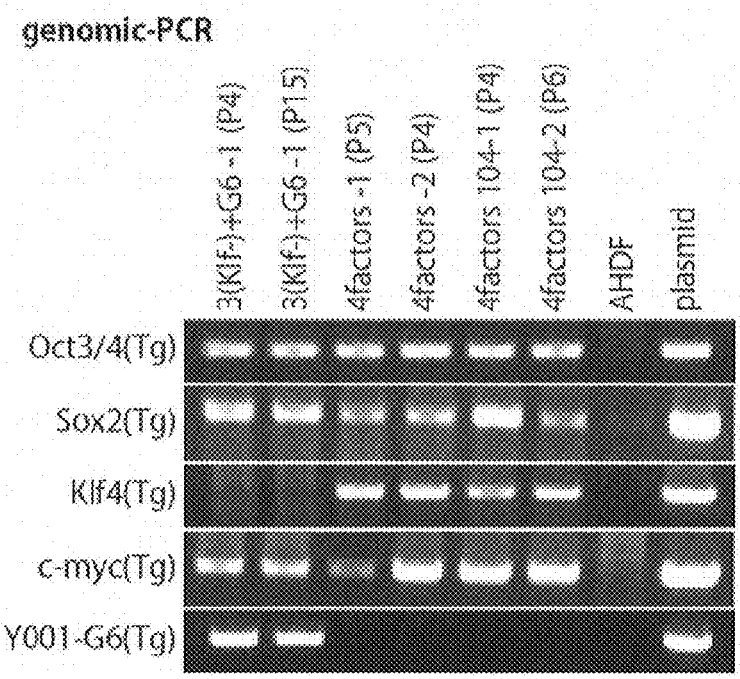

FIG. 31 is a photographic representation of the results of genomic-PCR on an iPS cell clone established by transferring 3 genes (Oct3/4, Sox2, c-Myc) and G6 (GLIS1) into HDF. In this figure, "4 factors" indicates an iPS cell established with 4 genes (Oct3/4, Sox2, c-Myc, Klf4), "AHDF" indicates the adult skin fibroblasts used as a source of somatic cells, and "plasmid" indicates positive controls prepared by amplifying each gene incorporated in pMXs.

Figure 32:
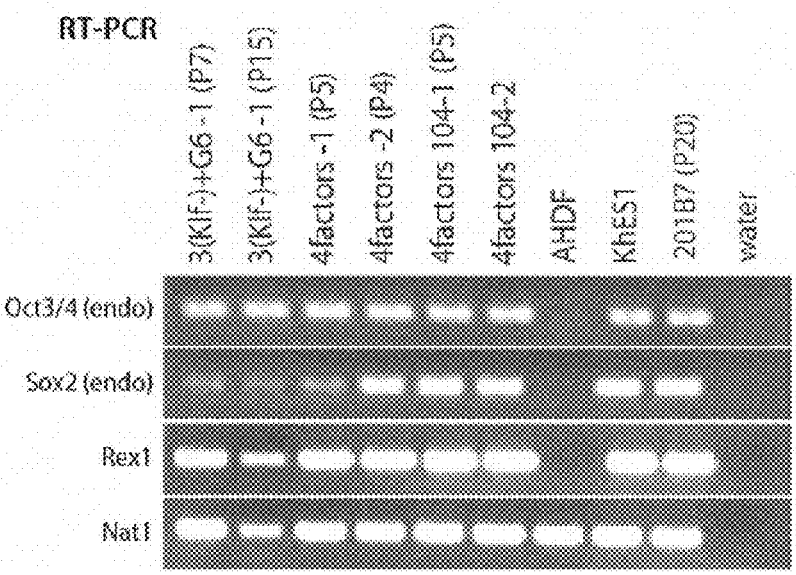

FIG. 32 is a photographic representation of the results of RT-PCR on an iPS cell clone established by transferring 3 genes (Oct3/4, Sox2, c-Myc) and G6 (GLIS1) into HDF. In this figure, "4 factors" and "AHDF" are identical to those in FIG. 31, "KhES1" indicates human ES cells, and "201B7" indicates iPS cells established in the past [Cell, 131:861-872 (2007)].

Figure 33:
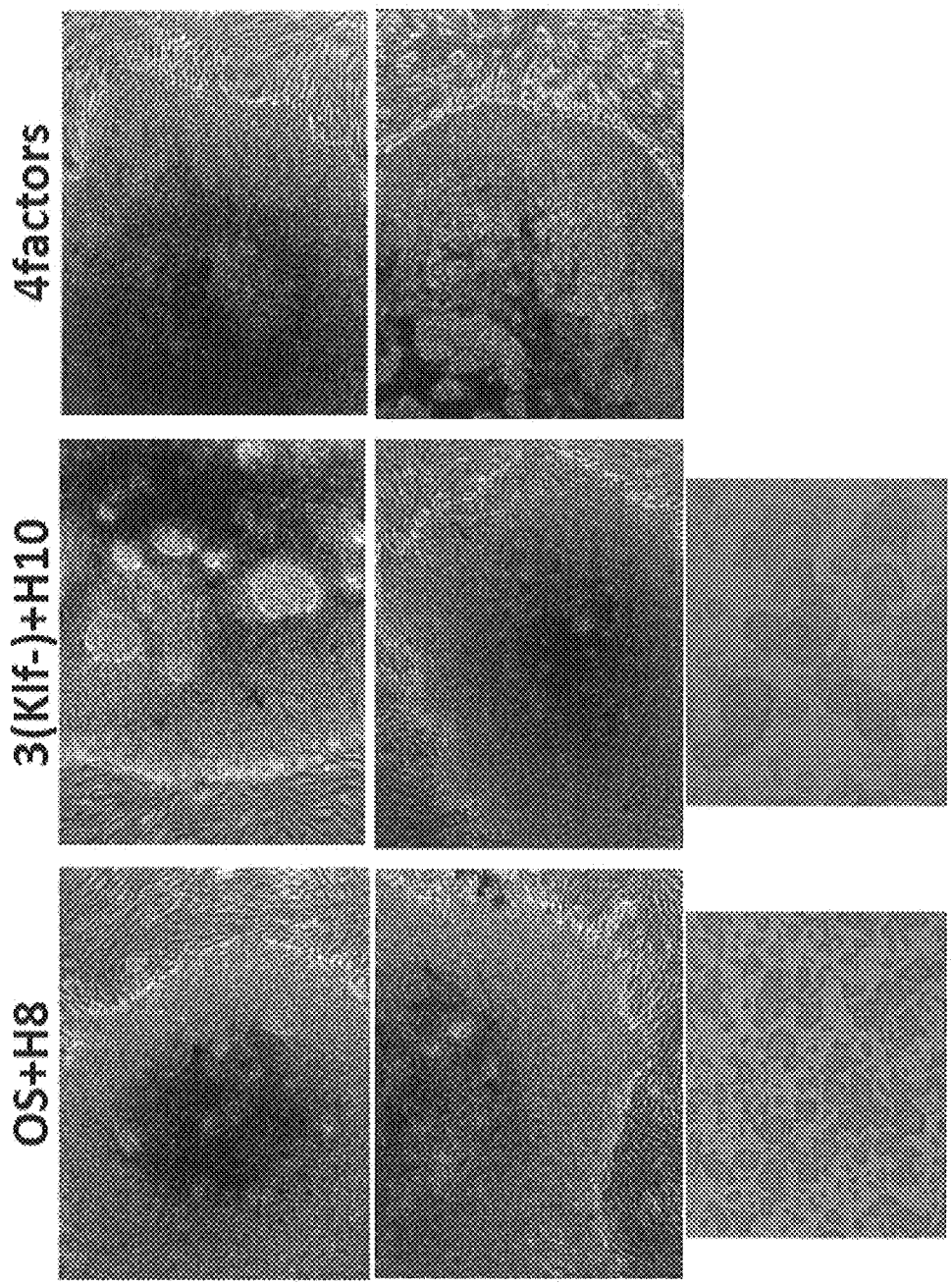

FIG. 33 is a photographic representation of colony images and alkaline phosphatase stain images of iPS cells established by transferring 2 genes (Oct3/4, Sox2) and H8 (DMRTB1), or 3 genes (Oct3/4, Sox2, c-Myc) and H10 (PITX2), into DP31. For control, a colony image of iPS cells established with 4 genes (Oct3/4, Sox2, c-Myc, Klf4) is also shown.

Figure 34:
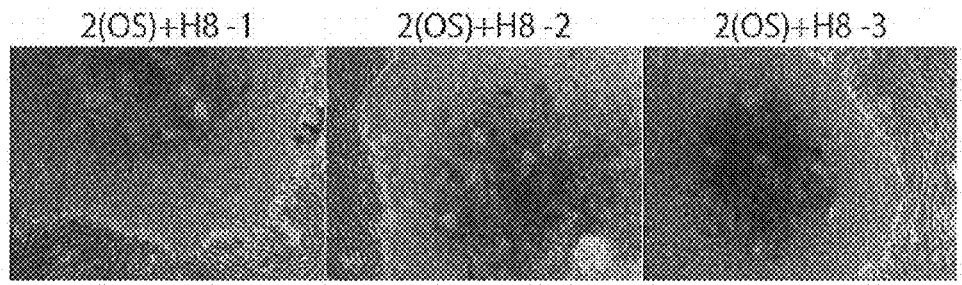

FIG. 34 is a photographic representation of a 1st-generation colony of iPS cells established by transferring 2 genes (Oct3/4, Sox2) and H8 (DMRTB1) into DP31.

Figure 35:
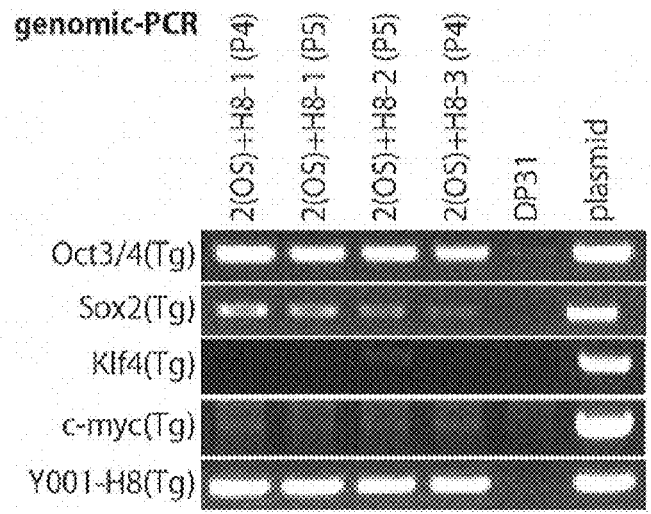

FIG. 35 is a photographic representation of the results of genomic-PCR on an iPS cell clone established by transferring 2 genes (Oct3/4, Sox2) and H8 (DMRTB1) into DP31. In this figure, "DP31" indicates the dental pulp stem cell clone used as a source of somatic cells, and "plasmid" indicates positive controls prepared by amplifying each gene incorporated into pMXs.

Figure 36:
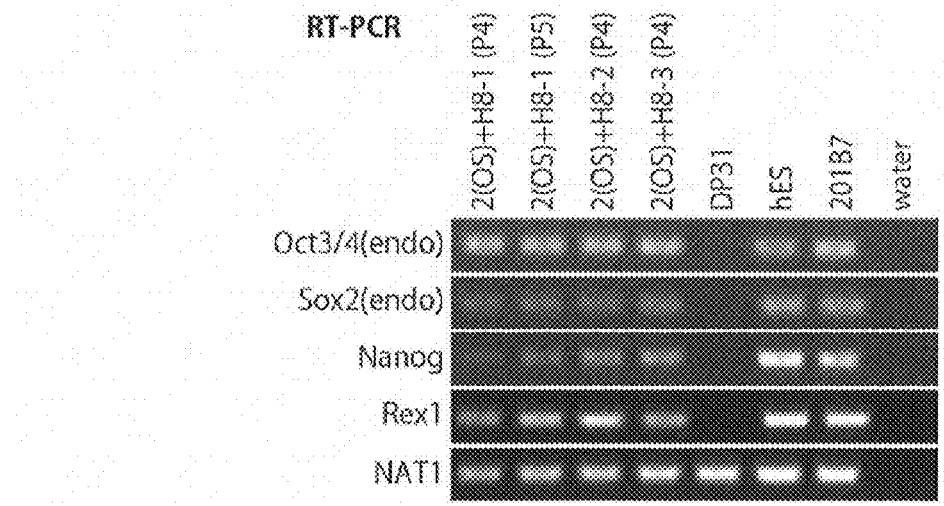

FIG. 36 is a photographic representation of the results of RT-PCR on an iPS cell clone established by transferring 2 genes (Oct3/4, Sox2) and H8 (DMRTB1) into DP31. In this figure, "DP31" indicates the dental pulp stem cell clone used as a source of somatic cells, "hES" indicates human ES cells, and "201B7" indicates iPS cells established in the past [Cell, 131:861-872 (2007)].

Figure 37:

FIG. 37 is a photographic representation of a 1st-generation colony of iPS cells established by transferring 3 genes (Oct3/4, Sox2, c-Myc) and H10 (PITX2) into DP31.

Figure 38:
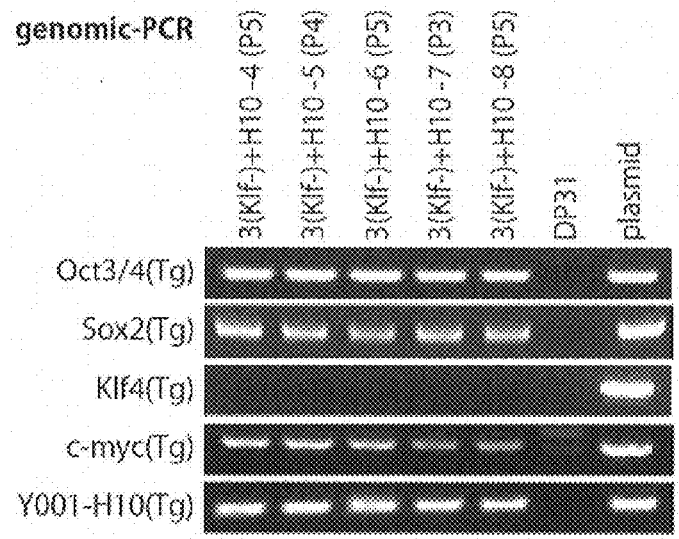

FIG. 38 is a photographic representation of the results of genomic-PCR on an iPS cell clone established by transferring 3 genes (Oct3/4, Sox2, c-Myc) and H10 (PITX2) into DP31. In this figure, "DP31" indicates the dental pulp stem cell clone used as a source of somatic cells, and "plasmid" indicates positive controls prepared by amplifying each gene incorporated into pMXs.

Figure 39:
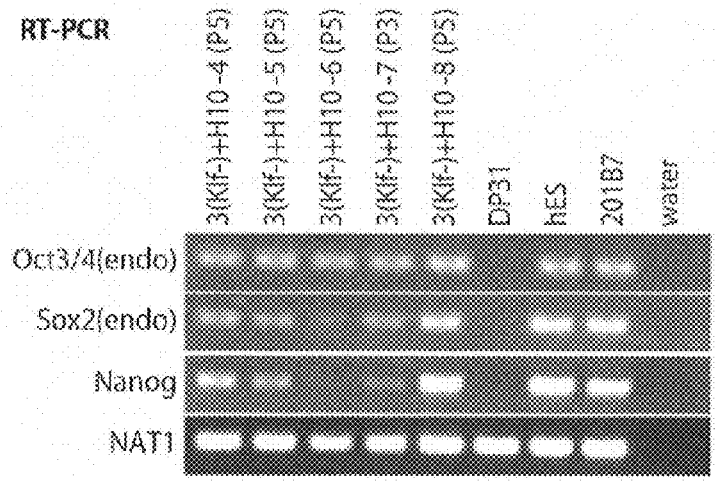

FIG. 39 is a photographic representation of the results of RT-PCR on an iPS cell clone established by transferring 3 genes (Oct3/4, Sox2, c-Myc) and H10 (PITX2) into DP31. In this figure, "DP31" indicates the dental pulp stem cell clone used as a source of somatic cells, "hES" indicates human ES cells, and "201B7" indicates iPS cells established in the past [Cell, 131:861-872 (2007)].

Figure 40:
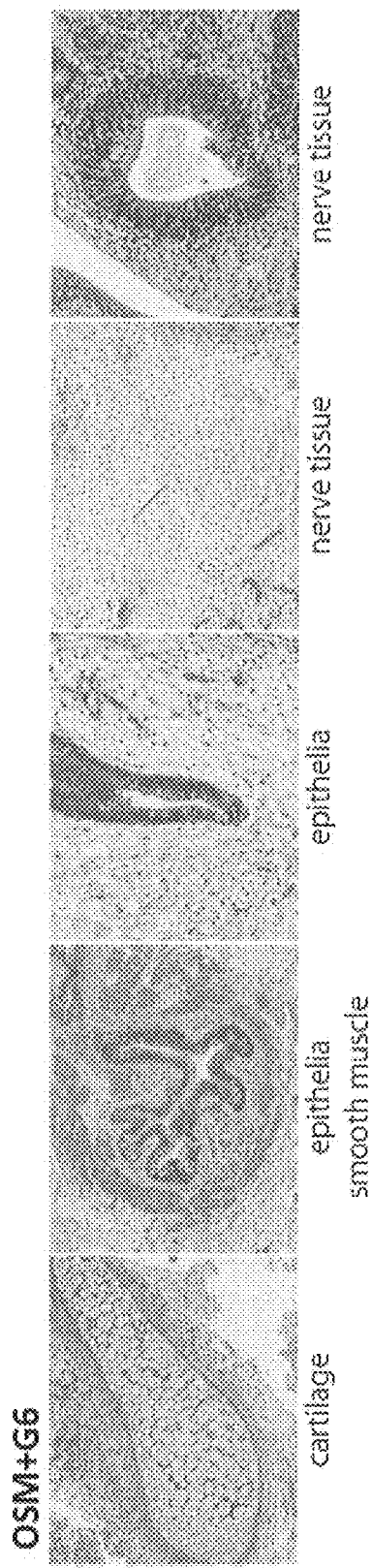

FIG. 40 shows a histologically stained image (hematoxylin-eosin stain) of a teratoma prepared by injecting an iPS cell clone established with 3 genes (Oct3/4, Sox2, c-Myc) and G6 (GLIS1) into an Scid mouse testis.

DETAILED DESCRIPTION OF THE INVENTION

The present invention provides a novel nuclear reprogramming substance that can substitute for Klf4 and a method of producing iPS cells by transferring the substance and a nuclear reprogramming substance capable of inducing iPS cells from a somatic cell when combined with Klf4, into a somatic cell.

(a) Novel Nuclear Reprogramming Substance (Substitute for Klf4)

In the present invention, "a nuclear reprogramming substance" refers to any substance(s) capable of inducing an iPS cell from a somatic cell, which may be composed of any substance such as a proteinous factor or a nucleic acid that encodes the same (including forms incorporated in a vector), or a low-molecular compound. A nuclear reprogramming substance that can substitute for Klf4, identified by the present invention, is a protein out of members of the IRX family, members of the GLIS family, members of the PTX family and DMRT-like family B with proline-rich C-terminal, 1 (DMRTB1), or a nucleic acid that encodes the same.

The IRX (iroquois homeobox) family has a homeobox domain, and is thought to play a multiple role during the pattern formation process in the vertebral embryo. Examples of members of this gene family include, but are not limited to, iroquois homeobox protein 1 (IRX1), IRX2, IRX3, IRX4, IRX5, IRX6 and the like, with preference given to IRX6. IRX6 is a gene not expressed in human and mouse ES cells.

The GLIS family comprises transcriptional factors having five C2H2 type zinc finger regions, and controlling the expression of various genes in the process of embryogenesis positively or negatively. Examples of members of this gene family include, but are not limited to, GLIS family zinc finger 1 (GLIS1), GLIS2, GLIS3 and the like, with preference given to GLIS1. GLIS1 is a gene not expressed in mouse ES cells.

The PTX family has a homeobox domain, and is involved in organogenesis and determination of lateral asymmetry. Examples of members of this gene family include, but are not limited to, paired-like homeodomain transcription factor 1 (PITX1), PITX2, PITX3 and the like, with preference given to PITX2. PITX2 is known to occur in three isoforms (isoforms a, b and c). Although any isoform can be used, isoform b, for example, is preferably used.

DMRT-like family B with proline-rich C-terminal, 1 (DMRTB1) is a transcriptional factor of unknown function having a doublesex DNA binding motif. DMRTB1 is a gene not expressed in human and mouse ES cells.

Although the members of the IRX family, members of the GLIS family, members of the PTX family and DMRTB1 used in the present invention may be proteins derived from optionally chosen mammals (e.g., humans, mice, rats, monkeys, bovines, horses, pigs, dogs and the like) or nucleic acids that encode the same, proteins or nucleic acids of human or mouse origin are preferred. Information on the amino acid sequences and cDNA sequences of the above-described nuclear reprogramming substances of human or mouse origin can be acquired by referring to the NCBI accession numbers shown in Table 1; those skilled in the art are easily able to isolate nucleic acids that encode the respective proteins on the basis of the cDNA sequence information, and to produce recombinant proteins as required.

TABLE 1

| Gene name | Human | | Mouse | |
|---|---|---|---|---|
| | cDNA | Protein | cDNA | Protein |
| IRX1 | NM_024337 | NP_077313 | NM_010573 | NP_034703 |
| IRX2 | NM_033267 | NP_150366 | NM_010574 | NP_034704 |
| IRX3 | NM_024336 | NP_077312 | NM_008393 | NP_032419 |
| IRX4 | NM_016358 | NP_057442 | NM_018885 | NP_061373 |
| IRX5 | NM_005853 | NP_005844 | NM_018826 | NP_061296 |
| IRX6 | NM_024335 | NP_077311 | NM_022428 | NP_071873 |
| | (SEQ ID NO: 1) | (SEQ ID NO: 2) | (SEQ ID NO: 3) | (SEQ ID NO: 4) |
| GLIS1 | NM_147193 | NP_671726 | NM_147221 | NP_671754 |
| | (SEQ ID NO: 5) | (SEQ ID NO: 6) | (SEQ ID NO: 7) | (SEQ ID NO: 8) |
| GLIS2 | NM_032575 | NP_115964 | NM_031184 | NP_112461 |
| GLIS3 | NM_001042413 | NP_001035878 | NM_175459 | NP_780668 |
| PITX1 | NM_002653 | NP_002644 | NM_011097 | NP_035227 |
| PITX2 (isoform a) | NM_153427 | NP_700476 | NM_001042504 | NP_001035969 |
| PITX2 (isoform b) | NM_153426 | NP_700475 | NM_011098 | NP_035228 |
| | (SEQ ID NO: 9) | (SEQ ID NO: 10) | (SEQ ID NO: 11) | (SEQ ID NO: 12) |
| PITX2 (isoform c) | NM_000325 | NP_000316 | NM_001042502 | NP_001035967 |
| PITX3 | NM_005029 | NP_005020 | NM_008852 | NP_032878 |
| DMRTB1 | NM_033067 | NP_149056 | XM_205469 | XP_205469 |
| | (SEQ ID NO: 13) | (SEQ ID NO: 14) | (SEQ ID NO: 15) | (SEQ ID NO: 16) |

A natural or artificial mutant protein having an identity of 90% or more, preferably 95% or more, more preferably 98% or more, particularly preferably 99% or more, to each amino acid sequence shown above, and possessing a potential for nuclear reprogramming as a substitute for Klf4 equivalent to that of the wild-type protein and a nucleic acid that encodes the same, can also be utilized as the nuclear reprogramming substance of the present invention that can substitute for Klf4.

Out of members of the IRX family, members of the GLIS family, members of the PTX family and DMRTB1 (including nucleic acids that encode the same), any one kind alone may be used, and two kinds or more may be used in combination.

(b) Nuclear Reprogramming Substance Capable of Inducing iPS Cells when Combined with Klf4

Currently, the following combinations of nuclear reprogramming substances comprising Klf4 are known to be capable of inducing iPS cells from a somatic cell (hereinafter, only the names of protein factors are given).

(1) Oct3/4, Klf4, c-Myc
(2) Oct3/4, Klf4, c-Myc, Sox2 (Sox2 is replaceable with Sox1, Sox3, Sox15, Sox17 or Sox18; c-Myc is replaceable with T58A (active mutant), N-Myc, or L-Myc)
(3) Oct3/4, Klf4, c-Myc, Sox2, Fbx15, Nanog, Eras, ECAT15-2, Tcl1, β-catenin (active mutant S33Y)
(4) Oct3/4, Klf4, c-Myc, Sox2, TERT, SV40 Large T
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV16 E6, HPV16 E7
(8) Oct3/4, Klf4, c-Myc, Sox2, TERT, Bmil

[For more information on the factors shown above, see WO 2007/069666 (for information on replacement of Sox2 with Sox18 in the combination (2) above, see *Nature Biotechnology*, 26, 101-106 (2008)); for the combination "Oct3/4, Klf4, c-Myc, Sox2", see also *Cell*, 126, 663-676 (2006), *Cell*, 131, 861-872 (2007) and the like; for the combination "Oct3/4, Klf4, c-Myc, Sox2, hTERT, SV40 Large T", see also Nature, 451, 141-146 (2008).]

(9) Oct3/4, Klf4, Sox2 [see *Nature Biotechnology*, 26, 101-106 (2008)]

(10) Oct3/4, Klf4, c-Myc, Sox2, Nanog, Lin28 [see *Cell Research* (2008) 600-603]

(11) Oct3/4, Klf4, c-Myc, Sox2, SV40 Large T (see also *Stem Cells*, 26, 1998-2005 (2008))

(12) Oct3/4, Klf4 [see also *Nature*, 454, 646-650 (2008); *Cell Stem Cell*, 2: 525-528 (2008)]

(13) Oct3/4, Klf4, L-Myc

Therefore, preferable combinations of nuclear reprogramming substances capable of inducing iPS cells when combined with Klf4 are combinations of the same substances as (1)-(13) above, but excluding Klf4, i.e., (i) Oct3/4, c-Myc
(ii) Oct3/4, c-Myc, Sox2 (Sox2 is replaceable with Sox1, Sox3, Sox15, Sox17 or Sox18; c-Myc is replaceable with T58A (active mutant), N-Myc, or L-Myc)
(iii) Oct3/4, c-Myc, Sox2, Fbx15, Nanog, Eras, ECAT15-2, Tcll, β-catenin (active mutant S33Y)
(iv) Oct3/4, c-Myc, Sox2, TERT, SV40 Large T
(v) Oct3/4, c-Myc, Sox2, TERT, HPV16 E6
(vi) Oct3/4, c-Myc, Sox2, TERT, HPV16 E7
(vii) Oct3/4, c-Myc, Sox2, TERT, HPV16 E6, HPV16 E7
(viii) Oct3/4, c-Myc, Sox2, TERT, Bmil
(ix) Oct3/4, Sox2
(x) Oct3/4, c-Myc, Sox2, Nanog, Lin28
(xi) Oct3/4, c-Myc, Sox2, SV40 Large T
(xii) Oct3/4, and
(xiii) Oct3/4, L-Myc. With regard to (i)-(xiii) above, Oct3/4 can be replaced with other members of the Oct family, e.g., Oct1A, Oct6 and the like. Furthermore, Sox2 (or Sox1, Sox3, Sox15, Sox17, Sox18) can be replaced with other members of the Sox family, e.g., Sox7 and the like.

Judging from these facts combined together, a nuclear reprogramming substance capable of inducing iPS cells when combined with Klf4 is preferably selected from among members of the Oct family (e.g., Oct3/4, Oct1A, Oct6), members of the Sox family (e.g., Sox2, Sox1, Sox3, Sox7, Sox15, Sox17, Sox18), members of the Myc family (e.g., c-Myc, n-Myc, L-Myc), and the Nanog and members of Lin families (e.g., Lin28, Lin28b). More preferably, a combination that comprises at least Oct3/4 and may optionally further comprise Sox2 and/or c-Myc [i.e., any one of (a) Oct3/4, (b) Oct3/4+Sox2, (c) Oct3/4+c-Myc, and (d) Oct3/4+Sox2+c-Myc] can be used, and this may be used in further combination with Nanog and/or Lin28. Here, a combination comprising L-Myc in place of c-Myc also represents a preferred embodiment.

Any combination other than (i) to (xiii) above but comprising all the constituents of any one thereof and further comprising any other optionally chosen substance can also be included in the scope of "nuclear reprogramming substances" in the present invention. For example, members of the Klf family (e.g., Klf1, Klf2, Klf5) or other known substitutional factors (e.g., member of the Esrr family such as Esrrb, Esrrg and the same) may be used in combination as other substances. Provided that the somatic cells to undergo nuclear reprogramming express one or more of the constituents of any one of (i) to (xiii) above endogenously at a level sufficient to cause nuclear reprogramming, the combination of the remaining constituents only, excluding the one or more constituents expressed can also be included in the scope of "nuclear reprogramming substances capable of inducing iPS cells when combined with Klf4" in the present invention.

Out of these combinations, a combination of the 2 factors Oct3/4 and Sox2 [i.e., (ix) above] or a combination of the 3 factors Oct3/4, Sox2 and L-Myc [i.e., (ii) above] is preferred with the use of the resulting iPS cells for therapeutic purposes in mind. Meanwhile, when the use of the iPS cells for therapeutic purposes is not in mind (e.g., use as a research tool such as for drug discovery screening, and the like), a combination of the four factors Oct3/4, c-Myc (or L-Myc), Sox2 and Lin28, or a combination of 5 factors consisting of the same 4 factors and Nanog [i.e., (x) above] is preferred.

Information on the mouse and human cDNA sequences of the aforementioned individual proteinous factors is available with reference to the NCBI accession numbers mentioned in WO 2007/069666 (in the publication, Nanog is described as ECAT4). Information on mouse and human cDNA sequences of Lin28 can be acquired with reference to NCBI accession number NM_145833 and NM_024674, respectively. Information on mouse and human cDNA sequences of Lin28b can be acquired with reference to NCBI accession number NM_001031772 and NM_001004317, respectively; information on mouse and human cDNA sequences of L-Myc can be acquired with reference to NCBI accession number NM_008506 and NM_001033081, respectively; those skilled in the art are able to easily isolate these cDNAs. When used as the nuclear reprogramming substance, the protein factor itself can be prepared by inserting the cDNA obtained into an appropriate expression vector, transferring the vector into a host cell, culturing the cell, and recovering a recombinant proteinous factor from the resulting culture. Meanwhile, when the nuclear reprogramming substance used is a nucleic acid that encodes a proteinous factor, the cDNA obtained is inserted into a viral or plasmid vector to construct an expression vector, and the vector is subjected to the step of nuclear reprogramming.

Nuclear reprogramming substances capable of inducing iPS cells when combined with Klf4 include not only combinations of the above-described conventionally known proteinous factors or nucleic acids that encode the same, but also combinations of proteinous factors that will be newly discovered or nucleic acids that encode the same, and can further include combinations comprising a non-proteinous factor such as a low-molecular compound, as far as it is capable of converting a somatic cell to an iPS cell when introduced into the somatic cell along with Klf4.

(c) Sources of Somatic Cells

Any cells, but other than germ cells, of mammalian origin (e.g., humans, mice, monkey, swine, rat etc.) can be used as starting material for the production of iPS cells in the present invention. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation, age of animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as nerve stem cells, hematopoietic stem cells, mesenchymal stem cells, and dental pulp stem cells.

The choice of individual mammal as a source of somatic cells is not particularly limited; however, when the iPS cells obtained are to be used for regenerative medicine in humans, it is particularly preferable, from the viewpoint of prevention of graft rejection, that somatic cells are patient's own cells or collected from another person (donor) having the same or substantially the same HLA type as that of the patient. Here, the statement that the HLA type is "substantially the same" means that there is an agreement of the HLA types to the extent that allows a cell graft to survive in a patient receiving cells obtained by inducing differentiation from the somatic cell-derived iPS cell, transplanted with the use of an immunosuppressant and the like. Examples include cases where the primary HLA types (e.g., 3 loci HLA-A, HLA-B and HLA-DR) are the same and the like (the same applies below). When the iPS cells obtained are not to be administered (transplanted) to a human, but used as, for example, a source of cells for screening for evaluating a patient's drug susceptibility or adverse reactions, it is likewise desirable to collect the somatic cells from the patient or another person with the same genetic polymorphism correlating with the drug susceptibility or adverse reactions.

Somatic cells separated from a mammal such as mouse or human can be pre-cultured using a medium known per se suitable for the cultivation thereof, depending on the kind of the cells. Examples of such media include, but are not limited to, a minimal essential medium (MEM) comprising about 5 to 20% fetal calf serum, Dulbecco's modified Eagle medium (DMEM), RPMI1640 medium, 199 medium, F12 medium, and the like. When a transfer reagent such as cationic liposome, for example, is used in bringing the cell into contact with a nuclear reprogramming substance (and, as required, also with the iPS cell establishment efficiency improver described below), it is sometimes preferable to exchange the medium with a serum-free medium in order to prevent transfer efficiency reductions.

(d) How to Transfer Nuclear Reprogramming Substance into Somatic Cell

Transfer of the "nuclear reprogramming substance that can substitute for Klf4" described in (a) above and the "nuclear reprogramming substance capable of inducing iPS cells when combined with Klf4" described in (b) above into a somatic cell can be performed using a method of protein transfer into cells which is known per se, provided that the substance is a proteinous factor. Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Genlantis), Pro-Ject™ Protein Transfection Reagent (PIERCE), PULSin™ delivery reagent (Polyplus-transfection) and ProVectin (IMGENEX); those based on a lipid, such as Profect-1 (Targeting Systems); those based on a membrane-permeable peptide, such as Penetrain Peptide (Q biogene), Chariot Kit (Active Motif), and GenomONE (Ishihara Sangyo), which employs HVJ envelop (inactivated Sendai virus), and the like. The transfer can be achieved per the protocols attached to these reagents, a common procedure being as described below. Nuclear reprogramming substance(s) is(are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as *drosophila*-derived AntP, HIV-derived TAT (Frankel, A. et al, Cell 55, 1189-93 (1988); Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl. Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1 (Morris, M. C. et al. Nature Biotechnol. 19, 1173-6 (2001)), Pep-7 (Gao, C. et al. Bioorg. Med. Chem. 10, 4057-65 (2002)), SynB1 (Rousselle, C. et al. Mol. Pharmacol. 57, 679-86 (2000)), HN-I (Hong, F. D. & Clayman, G L. Cancer Res. 60, 6551-6 (2000)), and HSV-derived VP22. PTD-derived CPPs include polyarginines such as 11R [Cell Stem Cell, 4:381-384 (2009)] and 9R [Cell Stem Cell, 4:472-476 (2009)].

A fusion protein expression vector incorporating a cDNA of a nuclear reprogramming substance and a PTD or CPP sequence is prepared to allow the recombinant expression of the fusion protein, and the fusion protein is recovered for use in for transfer. This transfer can be achieved as described above, except that no protein transfer reagent is added.

Microinjection, a method of placing a protein solution in a glass needle having a tip diameter of about 1 μm, and injecting the solution into a cell, ensures the transfer of the protein into the cell.

Other useful methods of protein transfer include electroporation, the semi-intact cell method [Kano, F. et al. Methods in Molecular Biology, Vol. 322, 357-365 (2006)], transfer using the Wr-t peptide [Kondo, E. et al., Mol. Cancer. Ther. 3(12), 1623-1630 (2004)] and the like.

The protein transfer operation can be performed one or more optionally chosen times (e.g., once or more to 10 times or less, or once or more to 5 times or less, and the like); preferably, the transfer operation can be performed twice or more (e.g., 3 times or 4 times) repeatedly. The time interval for repeated transfer is, for example, 6 to 48 hours, preferably 12 to 24 hours.

If emphasis is placed on iPS cell establishment efficiency, it is preferable to use the nuclear reprogramming substance in the form of a nucleic acid that encodes the same, rather than as the proteinous factor itself. The nucleic acid may be a DNA, an RNA, or a DNA/RNA chimera, and may be double-stranded or single-stranded. Preferably, the nucleic acid is a double-stranded DNA, particularly cDNA.

A cDNA of a nuclear reprogramming substance is inserted into an appropriate expression vector comprising a promoter capable of functioning in a host somatic cell. Useful expression vectors include, for example, viral vectors such as retrovirus, lentivirus, adenovirus, adeno-associated virus, herpes-virus and Sendai virus, plasmids for the expression in animal cells (e.g., pA1-11, pXT1, pRc/CMV, pRc/RSV, pcDNAI/Neo) and the like.

The kind of vector used can be chosen as appropriate according to the intended use of the iPS cells obtained. Useful vectors include, for example, adenovirus vectors, plasmid vectors, adeno-associated virus vectors, retrovirus vectors, lentivirus vectors, Sendai virus vectors and the like.

Examples of promoters used in expression vectors include the EF1alpha promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1alpha promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of useful selectable marker genes include the dihydrofolate reductase gene, the neomycin resistant gene, the puromycin resistant gene and the like.

The nucleic acids as nuclear reprogramming substances (reprogramming genes) may be separately integrated into different expression vectors, or 2 kinds or more, preferably 2 to 3 kinds, of genes may be incorporated into a single expression vector. Preference is given to the former case with the use of a retrovirus or lentivirus vector, which offer high gene transfer efficiency, and to the latter case with the use of a plasmid, adenovirus, or episomal vector and the like. Furthermore, an expression vector incorporating two kinds or more of genes and another expression vector incorporating one gene alone can be used in combination.

In the context above, when a plurality of genes are incorporated in one expression vector, these genes can preferably be inserted into the expression vector via an intervening sequence enabling polycistronic expression. By using an intervening sequence enabling polycistronic expression, it is possible to more efficiently express a plurality of genes incorporated in one kind of expression vector. Useful sequences enabling polycistronic expression include, for example, the 2A sequence of foot-and-mouth disease virus (SEQ ID NO:2; PLoS ONE 3, e2532, 2008, Stem Cells 25, 1707, 2007), IRES sequence (U.S. Pat. No. 4,937,190) and the like, with preference given to the 2A sequence.

An expression vector harboring a nucleic acid as a nuclear reprogramming substance can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. For example, specific means using a retroviral vector are disclosed in WO2007/69666, *Cell*, 126, 663-676 (2006) and *Cell*, 131, 861-872 (2007). Specific means using a lentivirus vector is disclosed in *Science*, 318, 1917-1920 (2007). When iPS cells are utilized as a source of cells for regenerative medicine, it is preferable that the reprogramming gene be expressed transiently, without being integrated into the chromosome of the cells because the expression (reactivation) of the reprogramming gene possibly increases the risk of carcinogenesis in the tissues regenerated from a differentiated cell from an iPS cell. From this viewpoint, use of an adenoviral vector, whose integration into chromosome is rare, is preferred. Specific means using an adenoviral vector is disclosed in *Science*, 322, 945-949 (2008). Because adeno-associated virus is also low in the frequency of integration into chromosome, and is lower than adenoviral vectors in terms of cytotoxicity and inflammation inducibility, it can be mentioned as another preferred vector. Because Sendai viral vector is capable of being stably present outside the chromosome, and can be degraded and removed using an siRNA as required, it is preferably utilized as well. Regarding Sendai viral vector, one described in *J. Biol. Chem.*, 282, 27383-27391 (2007), *Proc. Jpn. Acad., Ser. B* 85, 348-362 (2009) or JP Patent No. 3602058 can be used.

When a retroviral vector or a lentiviral vector is used, even if silencing of the transgene has occurred, it possibly becomes reactivated; therefore, for example, a method can be used preferably wherein a nucleic acid that encodes a nuclear reprogramming substance is cut out using the Cre/loxP system, when it has become unnecessary. That is, with a loxP sequence arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivated (SIN) LTR prepared by deleting the sequence, or substituting the sequence with a polyadenylation sequence such as of SV40. Specific means using the Cre-loxP system and SIN LTR is disclosed in Chang et al., *Stem Cells*, 27: 1042-1049 (2009).

Meanwhile, being a non-viral vector, a plasmid vector can be transferred into a cell using the lipofection method, liposome method, electroporation method, calcium phosphate co-precipitation method, DEAF dextran method, microinjection method, gene gun method and the like. Specific means using a plasmid as a vector are described in, for example, *Science*, 322, 949-953 (2008) and the like.

When a plasmid vector or adenovirus vector or the like is used, gene transfer can be performed once or more optionally chosen times (e.g., once to 10 times, or once to 5 times). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009); Woltjen et al., *Nature*, 458: 766-770 (2009).

Another preferred non-recombination type vector is an episomal vector autonomously replicable outside the chromosome. A specific procedure for using an episomal vector is disclosed by Yu et al. in *Science*, 324, 797-801 (2009). As required, an expression vector may be constructed by inserting a reprogramming gene into an episomal vector having loxP sequences placed in the same orientation at both the 5' and 3' sides of the vector element essential for the replication of the episomal vector, and this may be transferred into a somatic cell.

Examples of the episomal vector include vectors comprising a sequence required for its autonomous replication, derived from EBV, SV40 and the like, as a vector element. Specifically, the vector element required for its autonomous replication is a replication origin or a gene that encodes a protein that binds to the replication origin to regulate its replication; examples include the replication origin oriP and EBNA-1 gene for EBV, and the replication origin on and SV40 large T antigen gene for SV40.

The episomal expression vector contains a promoter that controls the transcription of the reprogramming gene. The promoter used can be the same promoter as the above. The episomal expression vector may further comprise an enhancer, poly-A addition signal, selection marker gene and the like as desired, as described above. Examples of selection marker gene include the dihydrofolate reductase gene, neomycin resistance gene and the like.

Examples of loxP sequences that can be used in the present invention include a bacteriophage P1-derived wild-type loxP sequence (SEQ ID NO:17), and an optionally chosen mutant loxP sequence capable of deleting the sequence between the loxP sequences by recombination when placed in the same orientation at positions sandwiching the vector element essential for the replication of the reprogramming gene. Examples of mutant loxP sequences include lox71 (SEQ ID NO:18), which has a mutation in the 5' side repeat sequence, lox66 (SEQ ID NO:19), which has a mutation in the 3' side repeat sequence, lox2272, lox511 and the like which have a mutation in the spacer moiety thereof. Although the two loxP sequences placed on the 5' and 3' sides of the vector element may be identical or not, an identical one (e.g., a pair of lox2272 sequences, a pair of lox511 sequences) is used in the case of mutant loxP sequences having a mutation in the spacer region thereof. Preferably, a combination of a mutant loxP sequence having a mutation in the 5' side repeat sequence (e.g., lox71) and a mutant loxP sequence having a mutation in the 3' side repeat sequence (e.g., lox66) is used. In this case, the loxP sequence remaining on the chromosome after the recombination has double mutations in the repeat sequences on the 5' and 3' sides, and is therefore unlikely to be recognized by Cre recombinase; therefore, the risk of causing a deletion mutation in the chromosome due to unwanted recombination is reduced. When both lox71 and lox66 are used, either mutant loxP sequence may be placed on the 5' and 3' sides of the aforementioned vector element, but it is necessary that the mutant loxP sequence be inserted in the orientation such that the mutated site is located at the outer end of the loxP sequence.

The two loxP sequences are placed in the same orientation on the 5' and 3' sides of a vector element essential for the replication of the reprogramming gene (i.e., replication origin, or a gene sequence that binds to the replication origin to regulate its replication). The vector element between the loxP sequences may be either a replication origin, or a gene sequence that encodes a protein that binds to the replication origin to regulate its replication, or both.

An episomal vector can be introduced into a cell using, for example, lipofection method, liposome method, electroporation method, calcium phosphate co-precipitation method, DEAE dextran method, microinjection method, gene gun method and the like. Specifically, the method described in *Science*, 324: 797-801 (2009), for example, can be used.

Whether or not the vector element required for replication of reprogramming gene has been removed from the iPS cell can be determined by performing Southern blot analysis or PCR analysis using a nucleic acid comprising a base sequence inside the vector element and/or in the vicinity of the loxP sequence as a probe or primer, with an episome fraction isolated from the iPS cell as the template, to examine for the presence or absence of a band or the length of the band detected. An episome fraction can be prepared using a method well known in the art, for example, the method described in *Science*, 324: 797-801 (2009).

When the nuclear reprogramming substance capable of inducing iPS cell by combination with Klf4 is a low-molecular compound, introducing thereof into a somatic cell can be achieved by dissolving the substance at an appropriate concentration in an aqueous or non-aqueous solvent, adding the solution to a medium suitable for cultivation of somatic cells isolated from human or mouse [e.g., minimal essential medium (MEM) comprising about 5 to 20% fetal bovine serum, Dulbecco's modified Eagle medium (DMEM), RPMI1640 medium, 199 medium, F12 medium and combinations thereof, and the like] so that the nuclear reprogramming substance concentration will fall in a range that is sufficient to cause nuclear reprogramming in somatic cells and does not cause cytotoxicity, and culturing the cells for a given period. The nuclear reprogramming substance concentration varies depending on the kind of nuclear reprogramming substance used, and is chosen as appropriate over the range of about 0.1 nM to about 100 nM. Duration of contact is not particularly limited, as far as it is sufficient to cause nuclear reprogramming of the cells; usually, the nuclear reprogramming substance may be allowed to be co-present in the medium until a positive colony emerges.

(e) iPS Cell Establishment Efficiency Improvers

In recent years, a wide variety of substances that improve the efficiency of establishment of iPS cells, which has traditionally been low, have been proposed one after another. Therefore, in addition to the above-described nuclear reprogramming substance, the efficiency of establishment of iPS cell can be expected to be increased by bringing these iPS cell establishment efficiency improvers into contact with a somatic cell.

Examples of iPS cell establishment efficiency improvers include, but are not limited to, histone deacetylase (HDAC) inhibitors [e.g., valproic acid (VPA) (*Nat. Biotechnol.*, 26(7): 795-797 (2008)], low-molecular inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine) [*Nat. Biotechnol.*, 26(7): 795-797 (2008)], G9a histone methyltransferase inhibitors [e.g., low-molecular inhibitors such as BIX-01294 (*Cell Stem Cell*, 2: 525-528 (2008), nucleic acid-based expression inhibitors such as siRNAs and shRNAs against G9a (e.g., G9a siRNA (human) (Santa Cruz Biotechnology) and the like) and the like], L-channel calcium agonists (e.g., Bayk8644) [*Cell Stem Cell*, 3, 568-574 (2008)], p53 inhibitors [e.g., siRNA and shRNA against p53 (*Cell Stem Cell*, 3, 475-479 (2008)), UTF1 [*Cell Stem Cell*, 3, 475-479 (2008)], Wnt Signaling inducers (e.g., soluble Wnt3a) [*Cell Stem Cell*, 3, 132-135 (2008)], 2i/LIF [2i is an inhibitor of mitogen-activated protein kinase signaling and glycogen synthase kinase-3, *PloS Biology*, 6(10), 2237-2247 (2008)], ES cell-specific miRNAs [e.g., miR-302-367 cluster (Mol. Cell. Biol. doi:10.1128/MCB.00398-08), miR-302 (RNA (2008) 14: 1-10), miR-291-3p, miR-294 and miR-295 (these three described in Nat. Biotechnol. 27: 459-461 (2009))] and the like. As mentioned above, the nucleic acid-based expression inhibitors may be in the form of expression vectors harboring a DNA that encodes an siRNA or shRNA.

Among the constituents of the aforementioned nuclear reprogramming substances, SV40 large T and the like, for example, can also be included in the scope of iPS cell establishment efficiency improvers because they are deemed not essential, but auxiliary, factors for somatic cell nuclear reprogramming. In the situation of the mechanisms for nuclear programming remaining unclear, the auxiliary factors, which are not essential for nuclear reprogramming, may be conveniently considered as nuclear reprogramming substances or iPS cell establishment efficiency improvers. Hence, because the somatic cell nuclear reprogramming process is understood as an overall event resulting from contact of nuclear reprogramming substance(s) and iPS cell establishment efficiency improver(s) with a somatic cell, it seems unnecessary for those skilled in the art to always distinguish between the nuclear reprogramming substance and the iPS cell establishment efficiency improver.

Contact of an iPS cell establishment efficiency improver with a somatic cell can be achieved as described above for each of cases: (a) the improver is a proteinous factor, (b) the improver is a nucleic acid that encodes the proteinous factor, and (c) the improver is a low-molecular compound.

An iPS cell establishment efficiency improver may be brought into contact with a somatic cell simultaneously with a nuclear reprogramming substance, or either one may be contacted in advance, as far as the efficiency of establishment of iPS cells from the somatic cell is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming substance and an iPS cell establishment efficiency improver are both used in the form of a viral or non-viral vector, for example, both may be simultaneously introduced into the cell.

(f) Improving the Establishment Efficiency by Culture Conditions

The efficiency of establishment of iPS cells can be further improved by culturing the somatic cells therefor under hypoxic conditions in the step of nuclear reprogramming of the cells. The term hypoxic conditions as used herein means that the oxygen concentration in the ambient atmosphere during cell culture is significantly lower than that in the air. Specifically, such conditions include lower oxygen concentrations than the oxygen concentrations in the ambient atmosphere of 5-10% $CO_2$/95-90% air, which is commonly used for ordinary cell culture; for example, oxygen concentrations of 18% or less in the ambient atmosphere are applicable.

Preferably, the oxygen concentration in the ambient atmosphere is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The oxygen concentration in the ambient atmosphere is preferably 0.1% or more (e.g., 0.2% or more, 0.3% or more, 0.4% or more and the like), 0.5% or more (e.g., 0.6% or more, 0.7% or more, 0.8% or more, 0.9% or more and the like), or 1% or more (e.g., 1.1% or more, 1.2% or more, 1.3% or more, 1.4% or more and the like).

There is no limitation on how to create hypoxic conditions in a cellular environment; the easiest of suitable methods is to culture cells in a $CO_2$ incubator that allows control of oxygen concentrations. Such $CO_2$ incubators are commercially available from a number of manufacturers of equipment (e.g., $CO_2$ incubators for hypoxic culture manufactured by Thermo Scientific, Ikemoto Scientific Technology, Juji Field Inc., and Wakenyaku Co., Ltd. can be used).

The timing of beginning cell culture under hypoxic conditions is not particularly limited, as far as it does not interfere with improving the efficiency of establishment of iPS cells compared with that obtained at a normal oxygen concentration (20%). The starting time may be before or after contact of nuclear reprogramming substances with a somatic cell, and may be at the same time as the contact. For example, it is preferable that cell culture under hypoxic conditions be begun just after contacting a nuclear reprogramming substance with a somatic cell, or after a given time (e.g., 1 to 10 (e.g., 2, 3, 4, 5, 6, 7, 8 or 9) days) following the contact.

The duration of cell culture under hypoxic conditions is not particularly limited, as far as it does not interfere with improving the efficiency of establishment of iPS cells compared with that obtained at a normal oxygen concentration (20%); examples include, but are not limited to, between 3 days or more, 5 days or more, 7 days or more or 10 days or more, and 50 days or less, 40 days or less, 35 days or less or 30 days or less. The preferred duration of cell culture under hypoxic conditions also varies depending on the oxygen concentration in the ambient atmosphere; those skilled in the art can adjust as appropriate the duration of cell culture according to the oxygen concentration used. In an embodiment of the present invention, when iPS cell candidate colonies are selected with drug resistance as an indicator, it is preferable that a normal oxygen concentration be restored from hypoxic conditions by the start of drug selection.

Furthermore, the preferred starting time and duration of cell culture under hypoxic conditions also vary depending on the choice of nuclear reprogramming substances used, the efficiency of establishment of iPS cells under conditions involving a normal oxygen concentration, and other factors.

After the nuclear reprogramming substance(s) (and iPS cell establishment efficiency improver(s)) is(are) brought into contact with the cell, the cell can be cultured under conditions suitable for the cultivation of, for example, ES cells. In the case of mouse cells, the cultivation is carried out with the addition of Leukemia Inhibitory Factor (LIF) as a differentiation suppressor to an ordinary medium. Meanwhile, in the case of human cells, it is desirable that basic fibroblast growth factor (bFGF) and/or stem cell factor (SCF) be added in place of LIF. Usually, the cells are cultured in the co-presence of mouse embryo-derived fibroblasts (MEFs) treated with radiation or an antibiotic to terminate the cell division thereof, as feeder cells. Usually, STO cells and the like are commonly used as MEFs, but for inducing iPS cells, SNL cells [McMahon, A. P. & Bradley, A. *Cell* 62, 1073-1085 (1990)] and the like are commonly used. Co-culture with feeder cells may be started before contact of the nuclear reprogramming substance, at the time of the contact, or after the contact (e.g., 1-10 days later).

A candidate colony of iPS cells can be selected by a method with drug resistance and reporter activity as indicators, and also by a method based on visual examination of morphology. As an example of the former, a colony positive for drug resistance and/or reporter activity is selected using a recombinant somatic cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant somatic cells include MEFs from a mouse having the βgeo (which encodes a fusion protein of β-galactosidase and neomycin phosphotransferase) gene knocked-in to the Fbx15 locus [Takahashi & Yamanaka, *Cell*, 126, 663-676 (2006)], MEFs from a transgenic mouse having the green fluorescent protein (GFP) gene and the puromycin resistance gene integrated in the Nanog locus [Okita et al., *Nature*, 448, 313-317 (2007)] and the like. Meanwhile, examples of the latter method based on visual examination of morphology include the method described by Takahashi et al. in *Cell*, 131, 861-872 (2007). Although the method using reporter cells is convenient and efficient, it is desirable from the viewpoint of safety that colonies be selected by visual examination when iPS cells are prepared for the purpose of human treatment. When the two factors Oct3/4 and Sox2 are used as nuclear reprogramming substances capable of inducing iPS cells by combination with Klf4, the resulting colonies are mostly of iPS cells of high quality comparable to ES cells, although the number of clones established decreases, so that iPS cells can be efficiently established even without using reporter cells.

The identity of the cells of a selected colony as iPS cells can be confirmed by positive responses to the above-described Nanog (or Oct3/4) reporters (puromycin resistance, GFP positivity and the like), as well as by the formation of a visible ES cell-like colony; however, to increase the accuracy, it is possible to perform tests such as alkaline phosphatase staining, analysis of the expression of various ES-cell-specific genes, and transplantation of the selected cells to a mouse and confirmation of teratoma formation.

When a nuclear reprogramming substance capable of substituting for Klf4 is transferred into a somatic cell in the form of a nucleic acid that encodes a protein selected from among members of the IRX family, members of the GLIS family, members of the PTX family and DMRTB1, the iPS cell obtained is a novel cell that is distinct from conventionally known iPS cells in that the exogenous nucleic acid is contained therein. In particular, if the exogenous nucleic acid is transferred into the somatic cell using a retrovirus, lentivirus or the like, the exogenous nucleic acid is usually integrated in the genome of the iPS cell obtained, so that the character of containing the exogenous nucleic acid is stably retained.

The iPS cells thus established can serve various purposes. For example, differentiation of the iPS cells into a wide variety of cells (e.g., myocardial cells, blood cells, nerve cells, vascular endothelial cells, insulin-secreting cells and the like) can be induced by means of a reported method of differentiation induction of ES cells. Therefore, inducing iPS cells using somatic cells collected from a patient or another person of the same or substantially the same HLA type would enable stem cell therapy based on transplantation, wherein the iPS cells are differentiated into desired cells (cells of an affected organ of the patient, cells having a therapeutic effect on disease, and the like), and the differentiated cells are transplanted to the patient. Furthermore, because functional cells (e.g., liver cells) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Example 1

Screening of a Novel Reprogramming Factor

Figure 1:
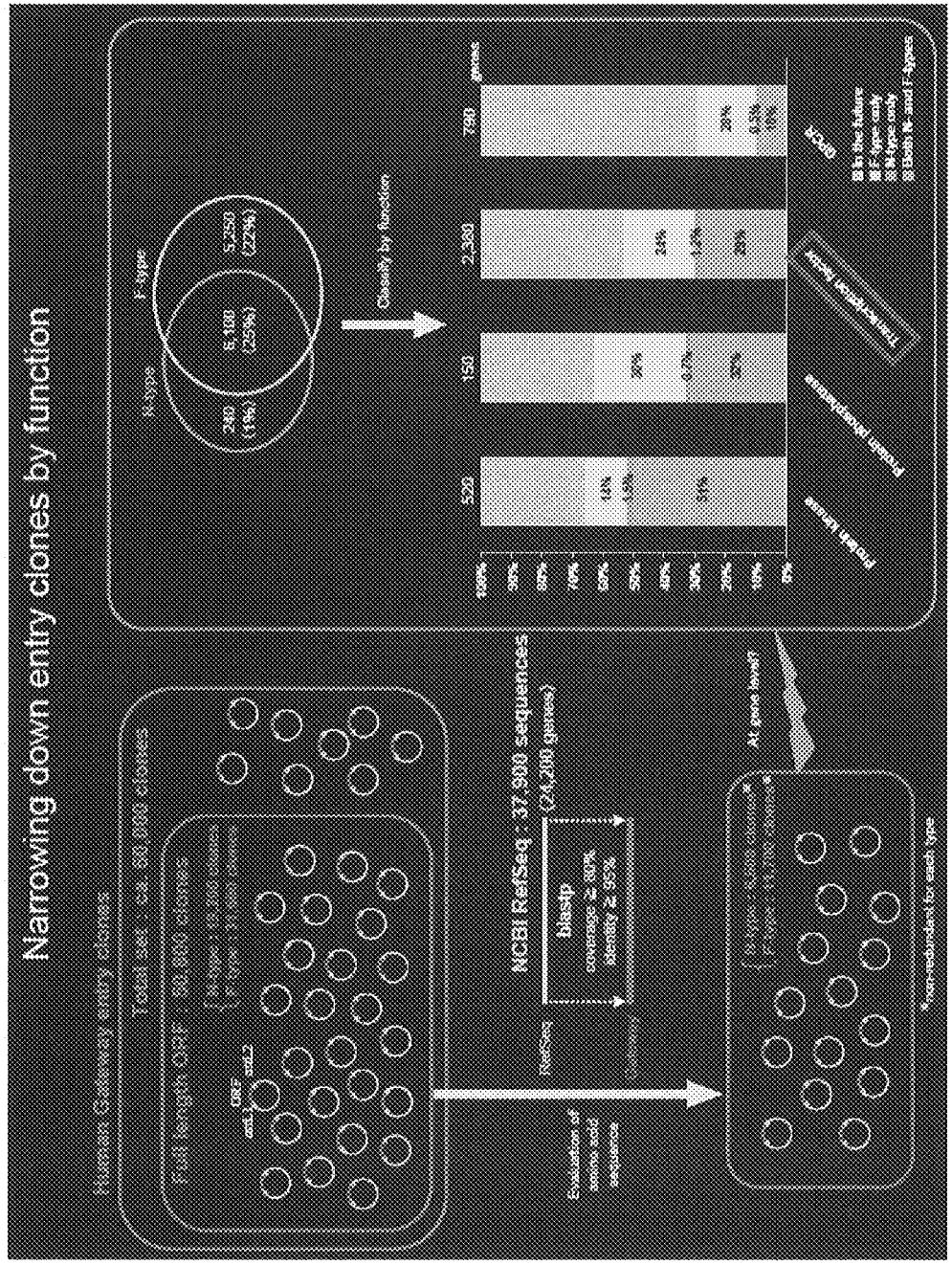
FIG. 1 is a schematic diagram showing the steps to the selection of entry clones by function from the human Gateway® entry clone (N. Goshima et al., Nature methods, 2008).
Figure 2:
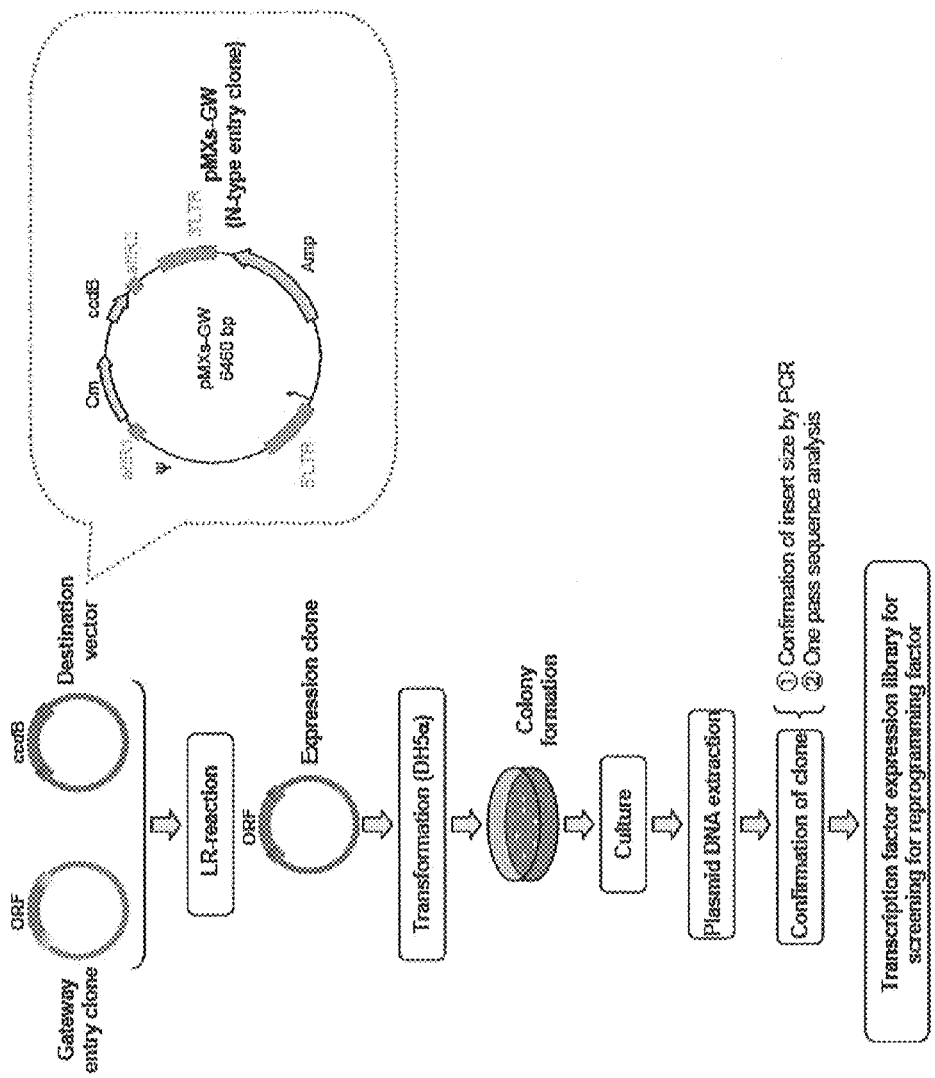
FIG. 2 shows a flow chart of generating a transcriptional factor expression library for somatic cell reprogramming factor screening from an entry clone of transcriptional factor.

Human Gateway® entry clones (The library described in N. Goshima et al., Nature Methods, 2008 was used. Database is disclosed in Y. Maruyama et al., Nucleic Acid Res., 2009.) produced by Goshima et al. were used to construct approximately 20000 clone contigs of human comprehensive genes according to the method described in FIG. 1. More specifically, blastp search of approximately 50000 clones containing the full length ORF from the human Gateway® entry clones was performed against the NCBI RefSeq 37900 sequences (24200 genes) using the criteria of 80% or better coverage, and amino acid identity of 95% or more, and a sublibrary was constructed consisting of approximately 20000 entry clones which did not have overlapping sequences within either an N-type having a stop codon at the 3' end of the ORF, or an F-type not having a stop codon. These approximately 20000 entry clone contigs were classified using bioinformatics techniques into protein kinases, protein phosphatases, transcription factors, GPCRs, or other groups of clones, and a sublibrary consisting of entry clones of transcription factors (covering not less than 50% of all human transcription factors) was constructed (FIG. 1). From this sublibrary of transcription factors, expression clone DNA was produced for every entry clone by LR reaction with a pMXs-GW destination vector as shown in FIG. 2, and this reaction solution was transfected into *E. coli* DH5a, cloned and a transcription factor expression library (transcription factor expression library for screening reprogramming factors) was constructed. Furthermore, human genes, Oct3/4, Sox2, Klf4 and c-Myc, were respectively integrated into the same pMXs-GW, and each expression clone was constructed. Recombinant retroviruses were produced from these DNA, which were used for the following experiments.

Induction experiments of iPS cells were carried out using dermal fibroblasts of Nanog-GFP mouse (Okita et al., Nature, 448, 313-317 (2007)). In this regard, experiments were carried out in two systems: one is a system in which infection of retroviruses was performed on MSTO (mytomicin-C treated SNL cells which have stopped cell division) feeder cells (hereinafter called the MSTO method, Cell, 126, 663-676 (2006)), and the other is a system in which feeder cells were not used at the time of infection, and cultivation was performed on MSTO after the cells were reseeded post infection (hereinafter called the Reseed method, Nature Biotech., 26, 101-106 (2008)).

For the first screening, iPS cell induction was carried out in 24-well plates. Nanog-GFP mouse dermal fibroblasts were seeded on Gelatin (Reseed method) or MSTO (MSTO method), and the next day, were infected with retroviruses produced by various plasmids (Day 0). Specifically, the cells were infected with the 3 genes, Oct3/4, Sox2 and c-Myc, and 1 gene from the aforementioned library of transcription factors at a ratio of 1:1:1:1. As a negative control, the cells were infected with the 3 genes, Oct3/4, Sox2 and c-Myc, at a ratio of 1:1:1. As a positive control, the 4 genes, Oct3/4, Sox2, Klf4 and c-Myc, at a ratio of 1:1:1:1.

Figure 3:
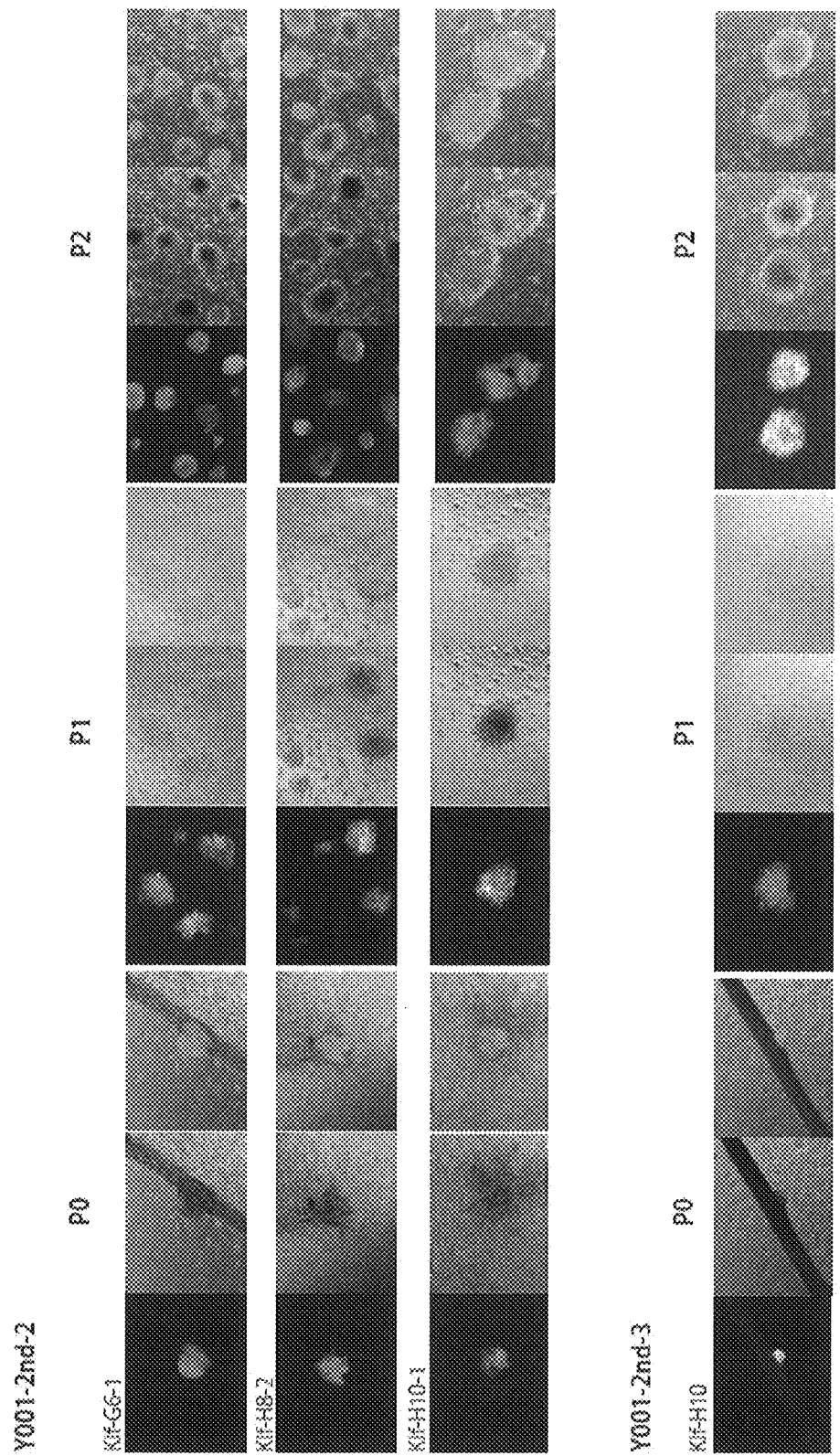
FIG. 3 is a photographic representation of the morphology of GFP-positive colonies obtained by transferring a total of 4 kinds of genes, i.e., 3 genes (Oct3/4, Sox2, c-Myc) and G06 (gene name: GLIS1), H08 (gene name: DMRTB1) or H10 (gene name: PITX2), into Nanog-GFP mouse skin fibroblasts by means of retrovirus. "Klf-G6-1" indicates an iPS cell clone obtained by transferring G06 (gene name: GLIS1) along with the 3 genes; "Klf-H8-2" indicates an iPS cell clone obtained by transferring H08 (gene name: DMRTB1) along with the 3 genes; "Klf-H10-1" and "Klf-H10" indicate iPS cell clones obtained by transferring H10 (gene name: PITX2) along with the 3 genes. P0 shows images taken at the time of colony establishment; P1 shows images for the 1st generation (24 wells); P2 shows images for the 2nd generation (6 wells). For each set of three photographs, the left panel shows an image of a GFP-positive colony, the central panel shows a phase-contrast image, and the right panel shows a superposed photograph of the GFP-positive colony image and phase-contrast image. Only Klf-H10-1 was established by the Reseed method, whereas the others were established by the MSTO method.
Figure 4:
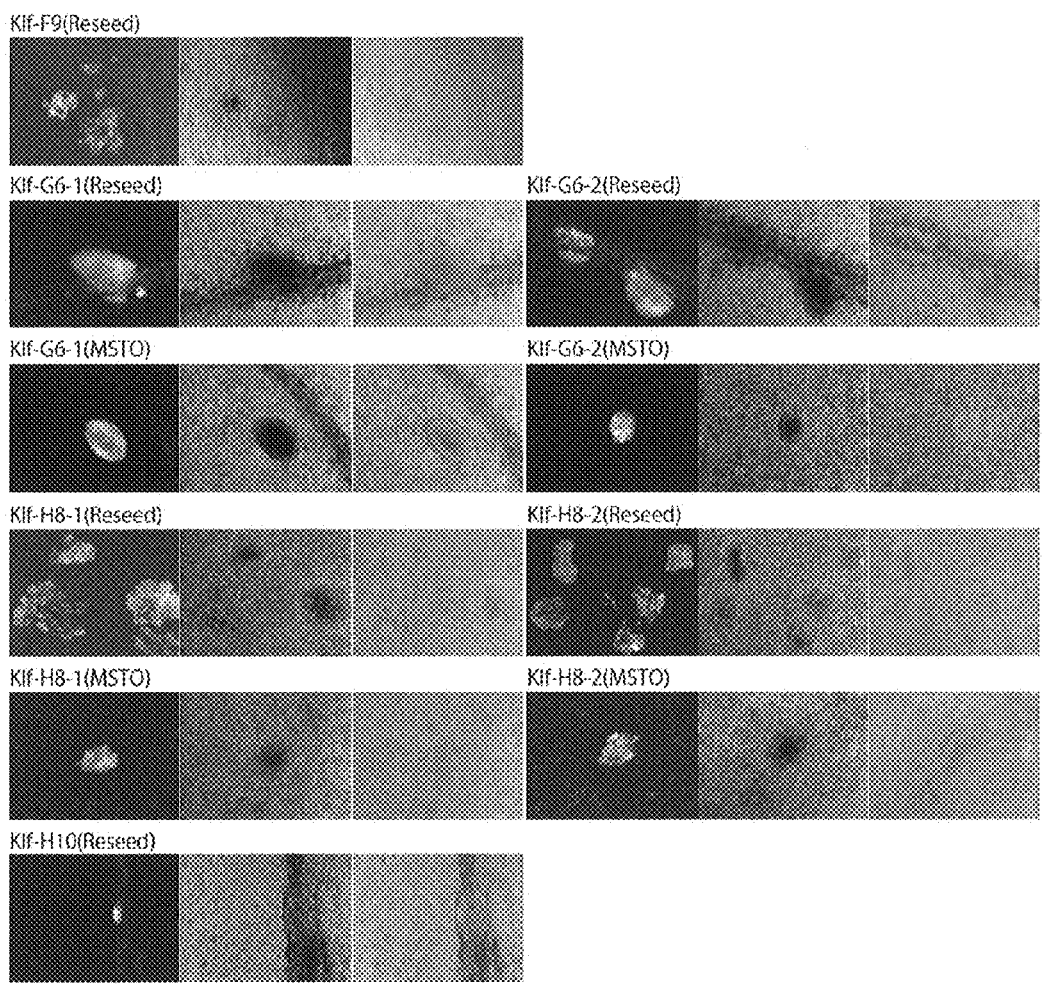
FIG. 4 is a photographic representation of the morphology of GFP-positive colonies obtained by transferring a total of 4 kinds of genes, i.e., 3 genes (Oct3/4, Sox2, c-Myc) and F09 (gene name: IRX6), G06 (gene name: GLIS1), H08 (gene name: DMRTB1) or H10 (gene name: PITX2), into Nanog-GFP mouse skin fibroblasts by means of retrovirus, as of the time of establishment of the colonies. "Klf-F9" indicates an iPS cell clone obtained by transferring F09 (gene name: IRX6) along with the 3 genes; "Klf-G6-1" and "Klf-G6-2" indicate iPS cell clones obtained by transferring G06 (gene name: GLIS1) along with the 3 genes; "Klf-H8-1" and "Klf-H8-2" indicate iPS cell clones obtained by transferring H08 (gene name: DMRTB1) along with the 3 genes; "Klf-H10" indicates an iPS cell clone obtained by transferring H10 (gene name: PITX2) along with the 3 genes. "Reseed" shows the results obtained by the Reseed method; "MSTO" shows the results obtained by the MSTO method.

The cells were cultivated in 10% FBS/DMEM until the second day from infection, and were cultivated in ES culture medium (Cell, 126, 663-676 (2006)) from day 3. When the cells were first seeded onto Gelatin (Reseed method), they were reseeded onto MSTO on day 3. Thereafter, the culture medium was replaced every 2 days, and these cells were subject to puromycin selection from day 21, and observed on day 28. As a result, in the wells in which the gene of sample F09 (gene name: IRX6), sample G06 (gene name: GLIS1), sample H08 (gene name: DMRTB1), or sample H10 (gene name: PITX2) was respectively transfected with the 3 genes, GFP-positive colonies appeared and the establishment of mouse iPS cells was confirmed. Furthermore, when iPS induction was performed again using 6-well plates, GFP-positive colonies also appeared and reproducibility was confirmed. GFP-positive colony image and the phase contrast image of respective iPS cells at the time of colony formation, passage 1 and passage 2, are shown in FIGS. 3 and 4.

From the above results, it was revealed that these 4 factors are novel reprogramming factors which substitute Klf4. Meantime, when MEF was used instead of adult mouse dermal fibroblasts, iPS cells (GFP-positive colonies) were also established.

Example 2

Analysis of Established Mouse iPS Cells

Figure 5:
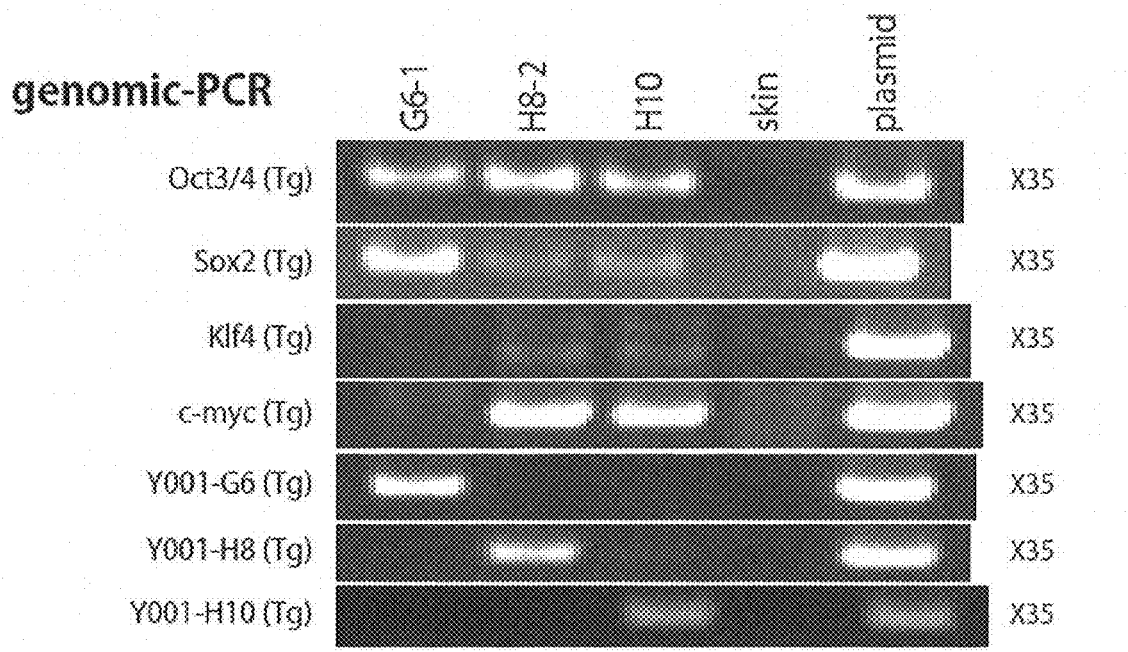
FIG. 5 is a photographic representation of the results of genomic-PCR on G6-1 (Klf-G6-1), H8-2 (Klf-H8-2) and H10 (Klf-H10) iPS cell clones. In this figure, "skin" indicates the fibroblast used as a source of somatic cells, and "plasmid" indicates positive controls prepared by amplifying each gene incorporated into pMXs.
Figure 6:
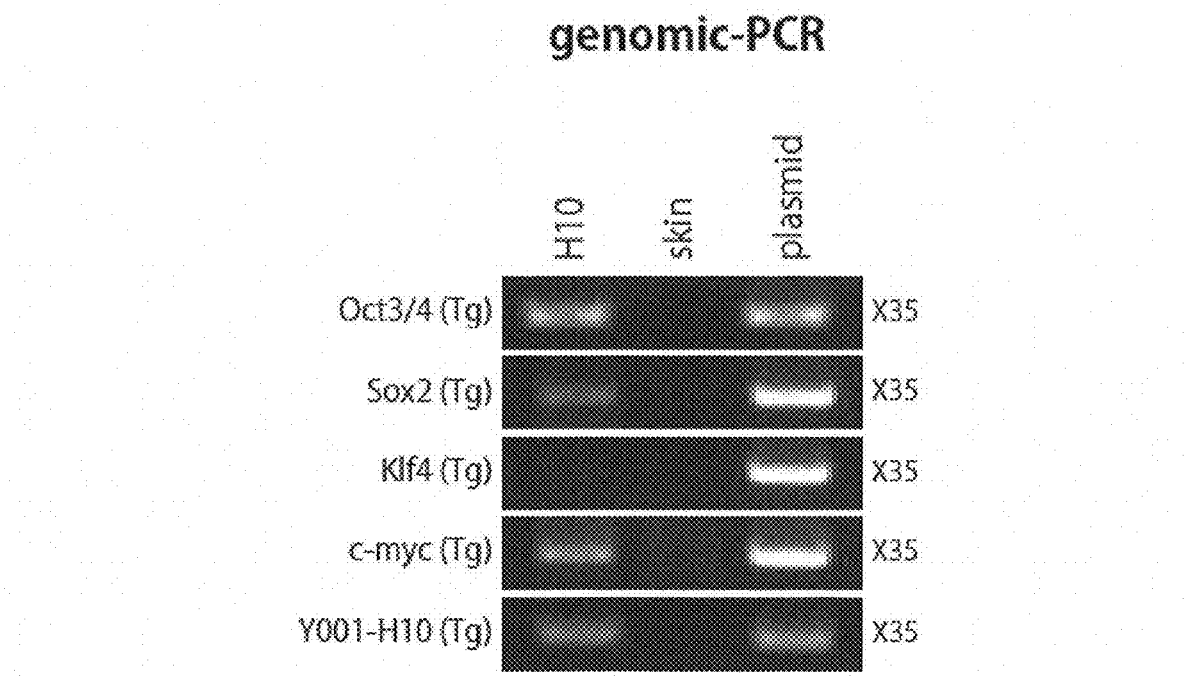
FIG. 6 is a photographic representation of the results of genomic-PCR on another H10 (Klf-H10) iPS cell clone other than that in FIG. 5. In this figure, "skin" indicates the fibroblast used as a source of somatic cells, and "plasmid" indicates positive controls prepared by amplifying each gene incorporated into pMXs.

Genome was extracted using QIAGEN "Gentra Puregene Cell Kit", and using a PCR enzyme (Takara Ex Taq), genomic-PCR was performed using the iPS cells established in Example 1. The results are shown in FIGS. 5 and 6. In all iPS cells, it was confirmed that only the transfected genes were inserted into the genome and the genes that were not used for transfection were not inserted into the genome. Meantime, in the G6-1 clone (gene name: GLIS1), c-Myc which was used for transfection, had not been inserted into the genome (FIG. 5). Since retrovirus vectors are not stably expressed unless they are inserted into the genome, it is presumed that this G6-1 clone was established by the expression of only the 3 factors of Oct3/4, Sox2 and GLIS1.

Figure 7:
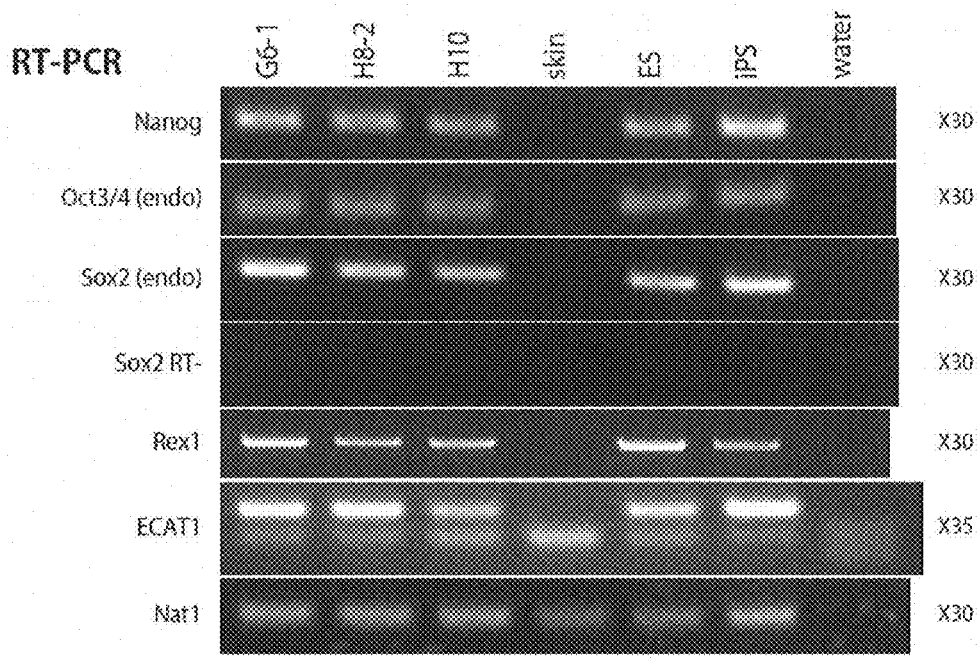
FIG. 7 is a photographic representation of the results of RT-PCR on G6-1 (Klf-G6-1), H8-2 (Klf-H8-2) and H10 (Klf-H10) iPS cell clones. In this figure, "skin" indicates the fibroblast used as a source of somatic cells; "ES" and "iPS" indicate mouse ES cells and iPS cells; "Sox2 RT-" is a negative control.
Figure 8:
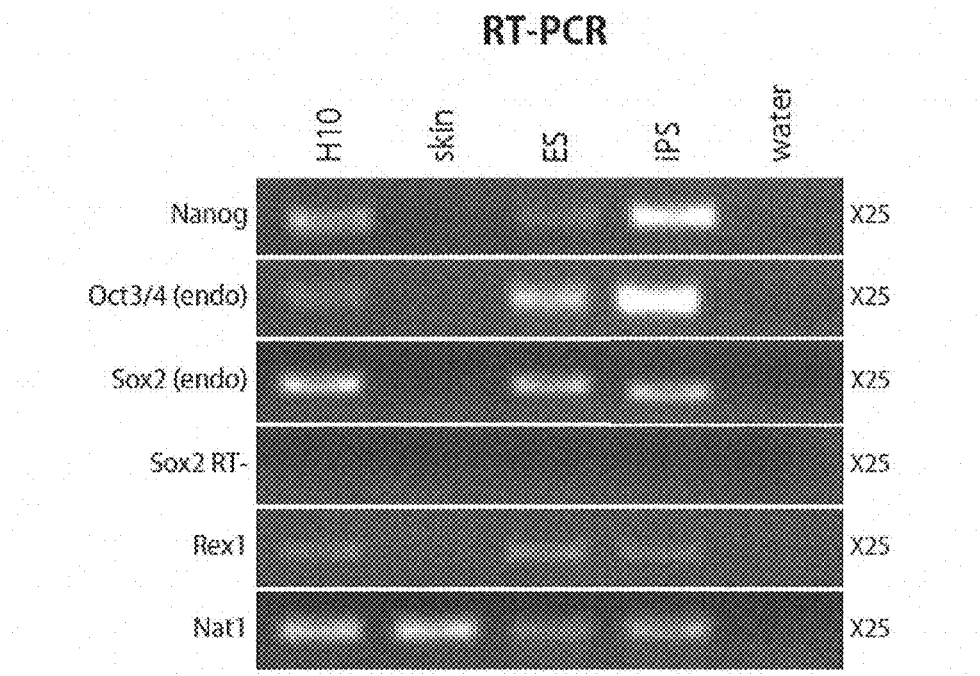
FIG. 8 is a photographic representation of the results of RT-PCR on another H10 (Klf-H10) iPS cell clone other than that in FIG. 7. In this figure, "skin" indicates the fibroblast used as a source of somatic cells; "ES" and "iPS" indicate mouse ES cells and iPS cells; "Sox2 RT-" is a negative control.

Next, RT-PCR analysis was performed using Rever Tra Ace kit (Takara). The results are shown in FIGS. 7 and 8. The iPS cells established in Example 1 all expressed the ES cell specific marker genes Nanog, Oct3/4, Sox2, Rex1 and ECAT1. From these results, the cells that were established using the novel reprogramming factors were confirmed to be iPS cells.

Example 3

Establishment and Analysis of Mouse iPS Cells (2)

Using the same method as Example 1, mouse iPS cells were established by introducing the following reprogramming factors. Nanog-GFP mouse dermal fibroblasts which were the same as in Example 1 were used, and both the MSTO method and the Reseed method were carried out.
(1) Oct3/4, Sox2, c-Myc, and G6 (gene name: GLIS1)
(2) Oct3/4, Sox2, c-Myc, and H8 (gene name: DMRTB1)
(3) Oct3/4, Sox2, c-Myc, and H10 (gene name: PITX2)
(4) Oct3/4, Sox2, and G6
(5) Oct3/4, Sox2, and H8
(6) Oct3/4, Sox2, and H10

Figure 9:
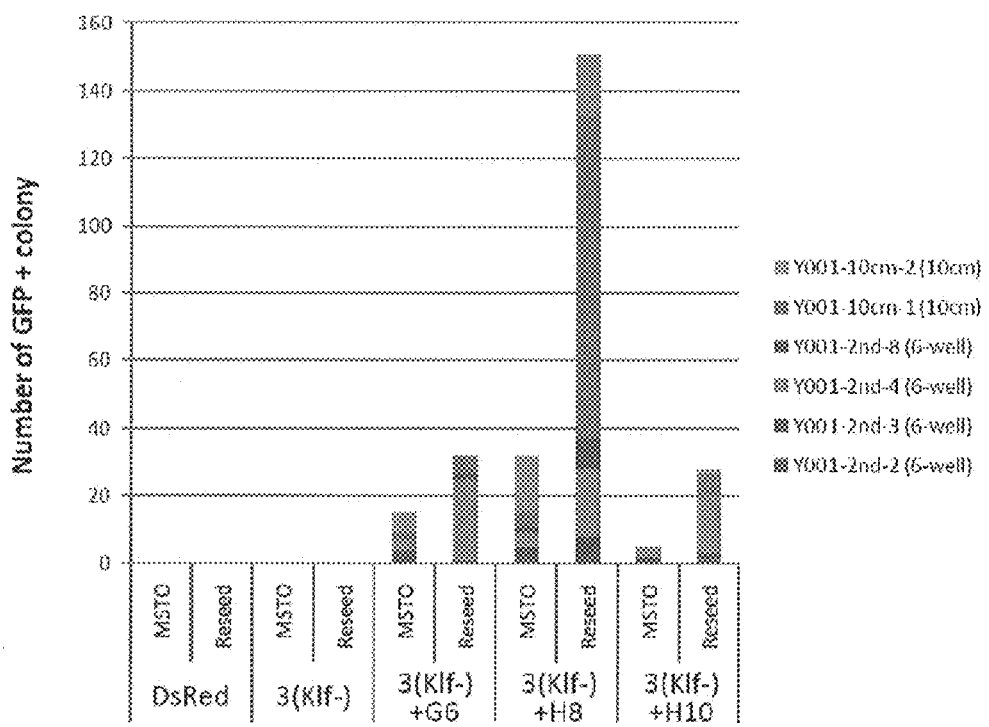
FIG. 9 is a graphic representation of the results of counting the number of colonies of iPS cells (GFP-positive cells) established by transferring a combination of 3 factors (Oct3/4, Sox2, c-Myc) and G6 (GLIS1), H8 (DMRTB1) or H10 (PITX2) into Nanog-GFP mouse skin fibroblasts. The results of six independent experiments are summarized.

The numbers of GFP-positive colonies were counted 28 days after gene transfection. The results of the above (1)-(3) are shown in FIG. 9 (it is a summarized result of 6 experiments). While no colonies were established using only 3 factors (Oct3/4, Sox2, c-Myc), colonies were established by adding the reprogramming factor of the present invention (GLIS1, DMRTB1 or PITX2). A particularly remarkable effect was observed when DMRTB1 was added. From these results, these factors of the present invention were confirmed to be reprogramming factors.

Figure 10:
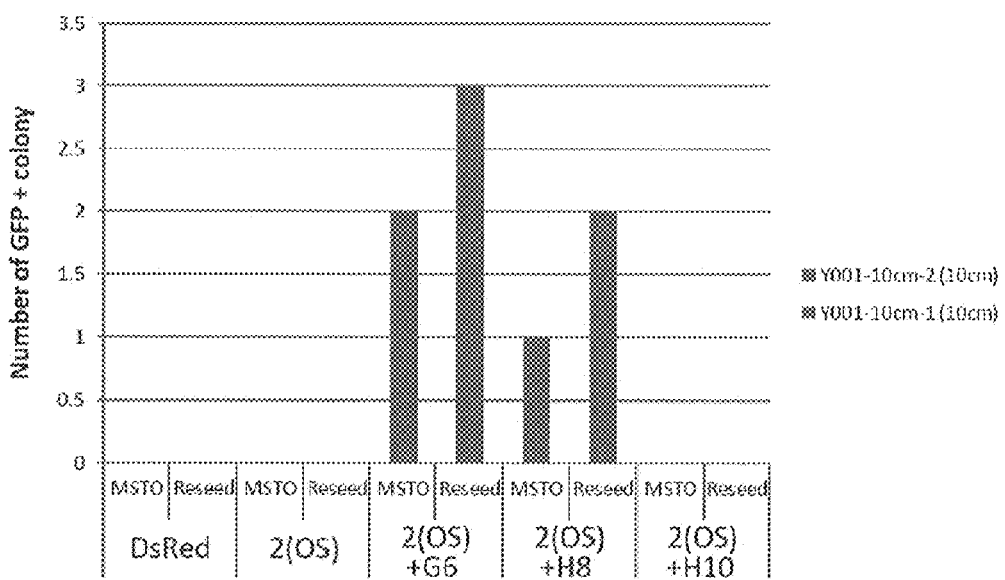
FIG. 10 is a graphic representation of the results of counting the number of colonies of iPS cells (GFP-positive cells) established by transferring a combination of 2 factors (Oct3/4, Sox2) and G6 (GLIS1), H8 (DMRTB1) or H10 (PITX2) into Nanog-GFP mouse skin fibroblasts. The results of two independent experiments are summarized.

The results of the above (4)-(6) are shown in FIG. 10 (it is a summarized result of 2 experiments). While no colonies were established with only 2 factors (Oct3/4, Sox2), colonies were established by adding the reprogramming factor of the present invention (GLIS1 or DMRTB1). Meantime, colonies were not observed in the 2 experiments in which PITX2 was added.

Figure 11:
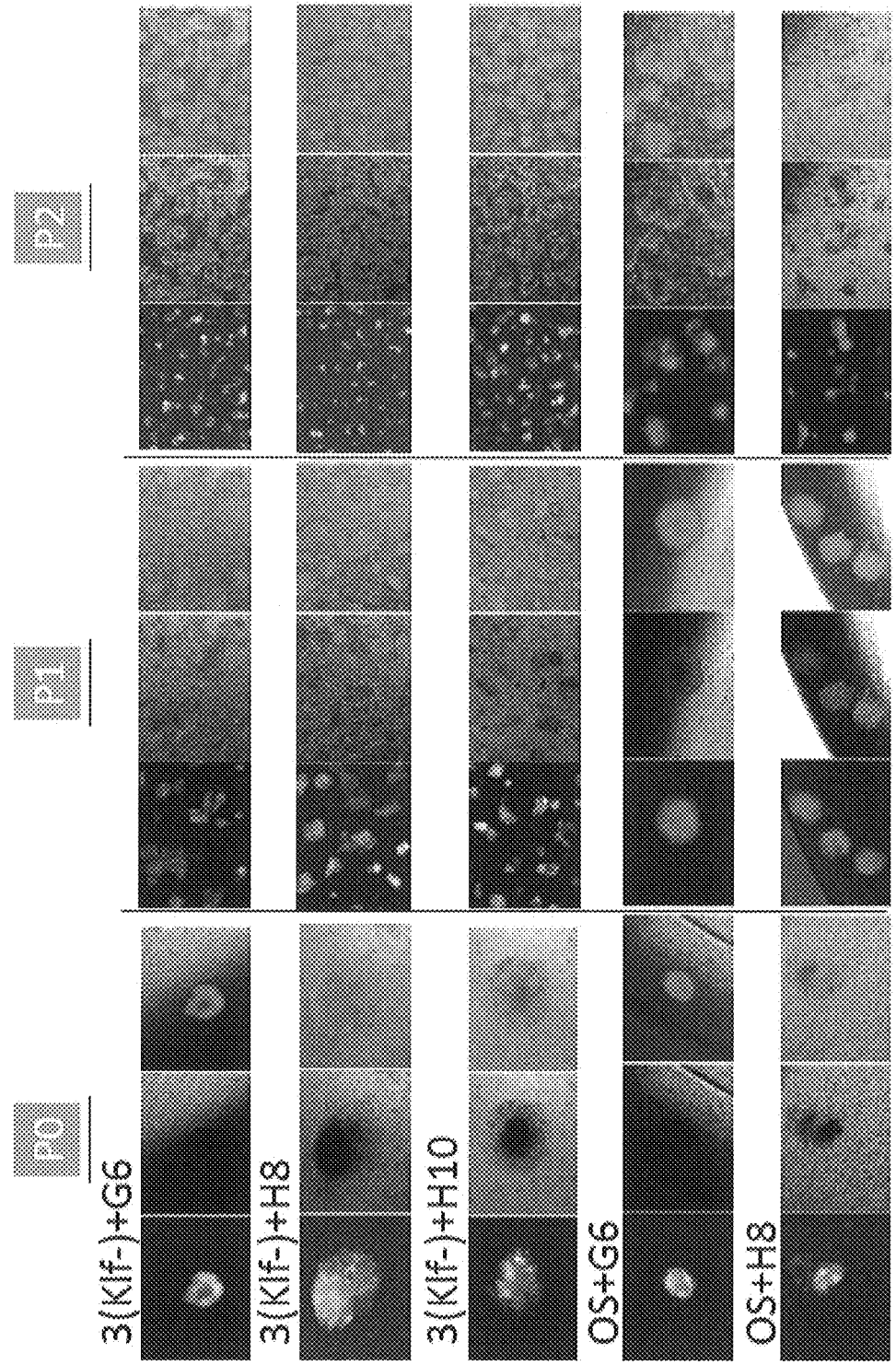
FIG. 11 is a photographic representation of colonies of iPS cells established by transferring a combination of 3 factors (Oct3/4, Sox2, c-Myc) and G6 (GLIS1), H8 (DMRTB1) or H10 (PITX2) into Nanog-GFP mouse skin fibroblasts, and colonies of iPS cells established by transferring a combination of 2 factors (Oct3/4, Sox2) and G6 (GLIS1) or H8 (DMRTB1) into Nanog-GFP mouse skin fibroblasts. P0 shows images taken at the time of colony establishment; P1 shows images for the 1st generation; P2 shows images for the 2nd generation. For each set of three photographs, the left panel shows an image of a GFP-positive colony, the central panel shows a phase-contrast image, and the right panel shows a superposed photograph of the GFP-positive colony image and phase-contrast image.

GFP-positive colony image and the phase contrast image of respective iPS cells at the time of colony formation (P0), passage 1 (P1) and passage 2 (P2), are shown in FIG. 11.

Figure 12:
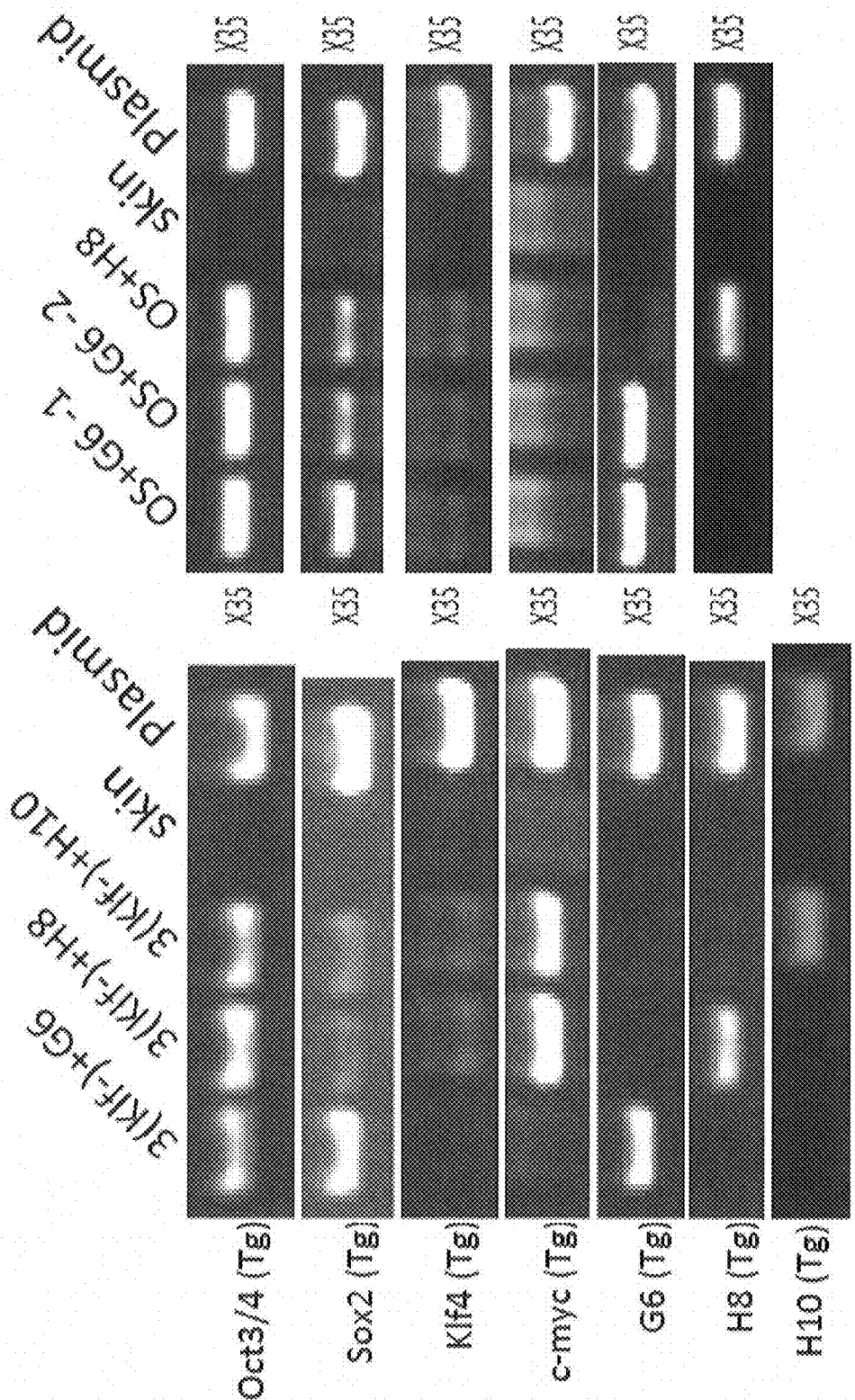
FIG. 12 is a photographic representation of the results of genomic-PCR on the iPS cell clones shown in FIG. 11. In this figure, "skin" indicates the fibroblast used as a source of somatic cells, and "plasmid" indicates positive controls prepared by amplifying each gene incorporated into pMXs.

Next, genome was extracted using QIAGEN "Gentra Puregene Cell Kit", and using a PCR enzyme (Takara Ex Taq), genomic-PCR was performed using the iPS cells established above. The results are shown in FIG. 12. In all iPS cells, it was confirmed that only the transfected genes were inserted into the genome and the genes that were not used for transfection were not inserted into the genome. Meantime, c-Myc which was used for transfection, had not been inserted into the genome in the experiment with 3 factors+G6 (GLIS1) (the leftmost lane of FIG. 12). Since retrovirus vectors are not stably expressed unless they are inserted into the genome, it is presumed that this clone was established by the expression of only the 3 factors of Oct3/4, Sox2 and GLIS1.

Figure 13:
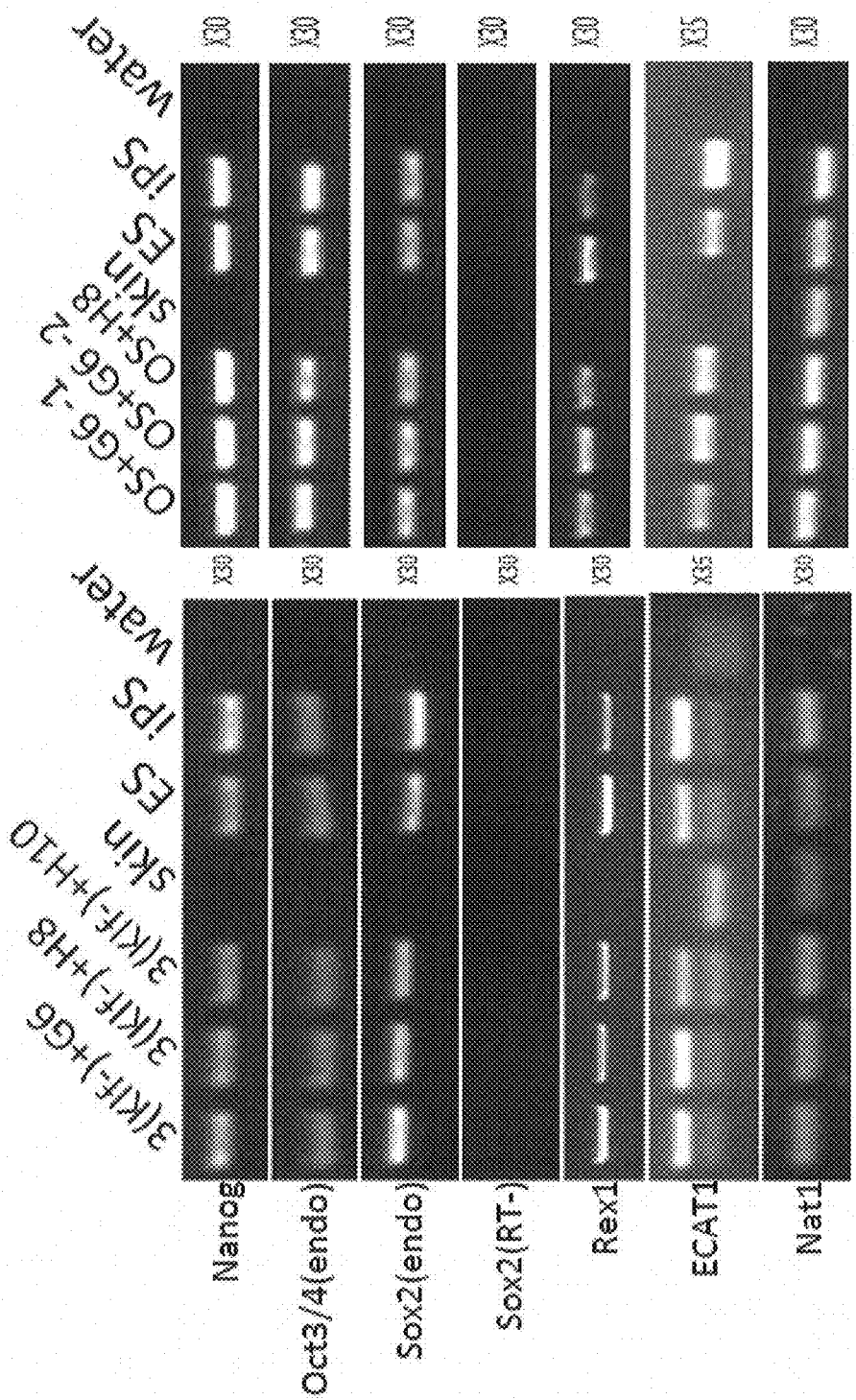
FIG. 13 is a photographic representation of the results of RT-PCR on the iPS cell clones shown in FIG. 11. In this figure, "skin" indicates the fibroblast used as a source of somatic cells, and "ES" and "iPS" indicate mouse ES cells and iPS cells established using 4 factors (Oct3/4, Sox2, c-Myc, Klf4).

Next, RT-PCR analysis was performed using Rever Tra Ace kit (Takara). The results are shown in FIG. 13. The iPS cells established above, all expressed the ES cell specific marker genes Nanog, Oct3/4, Sox2, Rex1 and ECAT1. From these results, the cells that were established using the novel reprogramming factors were confirmed to be iPS cells.

Example 4

Establishment and Analysis of Mouse iPS Cells (3)

Figure 14:
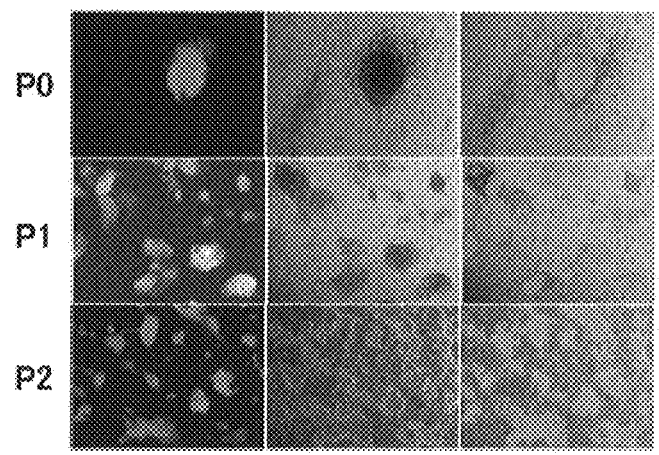
FIG. 14 is a photographic representation of colonies of iPS cells established by transferring a combination of 2 factors (Oct3/4,c-Myc) and H10 (PITX2) into Nanog-GFP mouse skin fibroblasts. P0 shows images taken at the time of colony establishment; P1 shows images for the 1st generation; P2 shows images for the 2nd generation. For each set of three photographs, the left panel shows a GFP-positive colony image, the central panel shows a phase-contrast image, and the right panel shows a superposed photograph of the GFP-positive colony image and phase-contrast image.

Using the same method as Example 3, mouse iPS cells were established by introducing Oct3/4 and c-Myc in combination with the reprogramming factors of the present invention (G6 (GLIS1), H8 (DMRTB1) or H10 (PITX2)). As a result, in the combination of Oct3/4, c-Myc and H10 (PITX2), GFP-positive colonies (iPS colonies) were detected. GFP-positive colony image and the phase contrast image of iPS colonies at the time of colony formation (P0), passage 1 (P1) and passage 2 (P2), are shown in FIG. 14.

Figure 15:
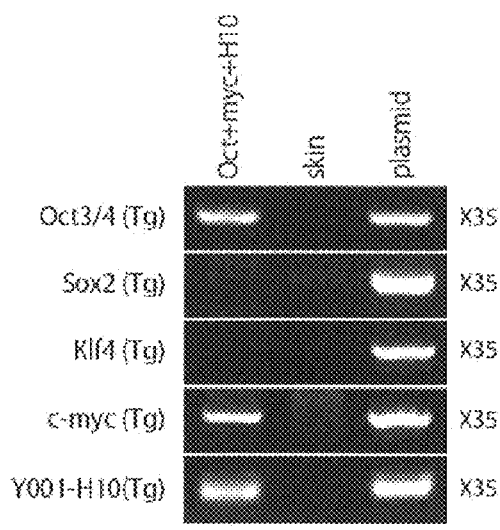
FIG. 15 is a photographic representation of the results of genomic-PCR on the iPS cell clones shown in FIG. 14. In this figure, "skin" indicates the fibroblast used as a source of somatic cells, and "plasmid" indicates positive controls prepared by amplifying each gene incorporated into pMXs.

Next, genome was extracted using QIAGEN "Gentra Puregene Cell Kit", and using a PCR enzyme (Takara Ex Taq), genomic-PCR was performed using the iPS cells established above. The results are shown in FIG. 15. In the established iPS cells, it was confirmed that only the transfected genes were inserted into the genome and the genes that were not used for transfection were not inserted into the genome.

Figure 16:
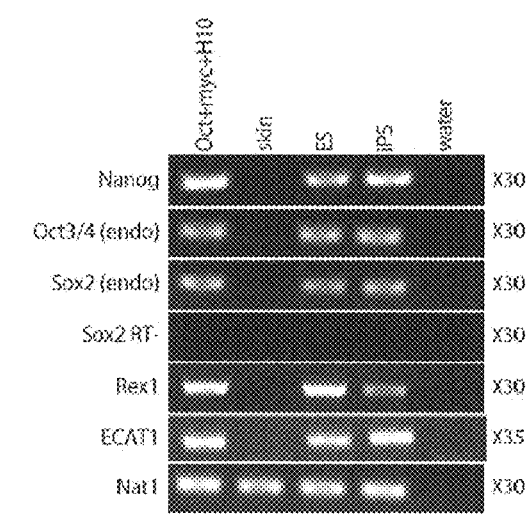
FIG. 16 is a photographic representation of the results of RT-PCR on the iPS cell clones shown in FIG. 14. In this figure, "skin" indicates the fibroblast used as a source of somatic cells, and "ES" and "iPS" indicate mouse ES cells and iPS cells established using 4 factors (Oct3/4, Sox2, c-Myc, Klf4).

Next, RT-PCR analysis was performed using Rever Tra Ace kit (Takara). The results are shown in FIG. 16. The iPS cells established above, expressed the ES cell specific marker genes Nanog, Oct3/4, Sox2, Rex1 and ECAT1. From these results, the cells that were established using the novel reprogramming factors were confirmed to be iPS cells.

Example 5

Establishment and Analysis of Mouse iPS Cells (4)

Fibroblasts (MEF) were isolated from fetal Nanog-GFP mouse (13.5 days after fertilization). The following reprogramming is factors were introduced into these MEF using the same technique as Examples 3 and 4.
(1) Oct3/4, Sox2, c-Myc, and G6 (gene name: GLIS1)
(2) Oct3/4, Sox2, c-Myc, and H8 (gene name: DMRTB1)
(3) Oct3/4, Sox2, c-Myc, and H10 (gene name: PITX2)
(4) Oct3/4, Sox2, and G6
(5) Oct3/4, Sox2, and H8
(6) Oct3/4, Sox2, and H10

Figure 17:
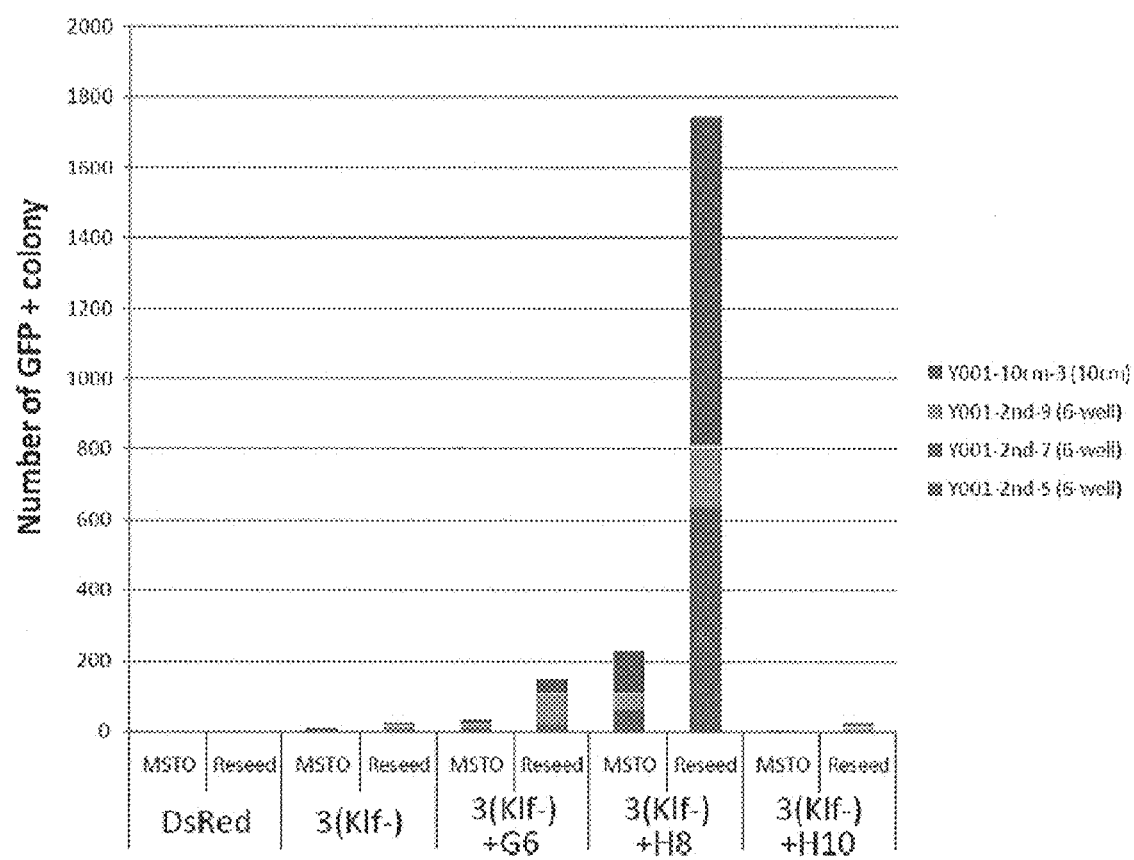
FIG. 17 is a graphic representation of the results of counting the number of colonies of iPS cells (GFP-positive cells) established by transferring a combination of 3 factors (Oct3/4, Sox2, c-Myc) and G6 (GLIS1), H8 (DMRTB1) or H10 (PITX2) into Nanog-GFP mouse MEF. The results of four independent experiments are summarized.

The numbers of GFP-positive colonies were counted 28 days after gene transfection. The results of the above (1)-(3) are shown in FIG. 17 (it is a summarized result of 4 experiments). While hardly any colonies were established using only 3 factors (Oct3/4, Sox2, c-Myc), colonies were established by adding the reprogramming factor of the present invention (GLIS1, DMRTB1 or PITX2), with a particularly remarkable effect observed when DMRTB1 was added.

Figure 18:
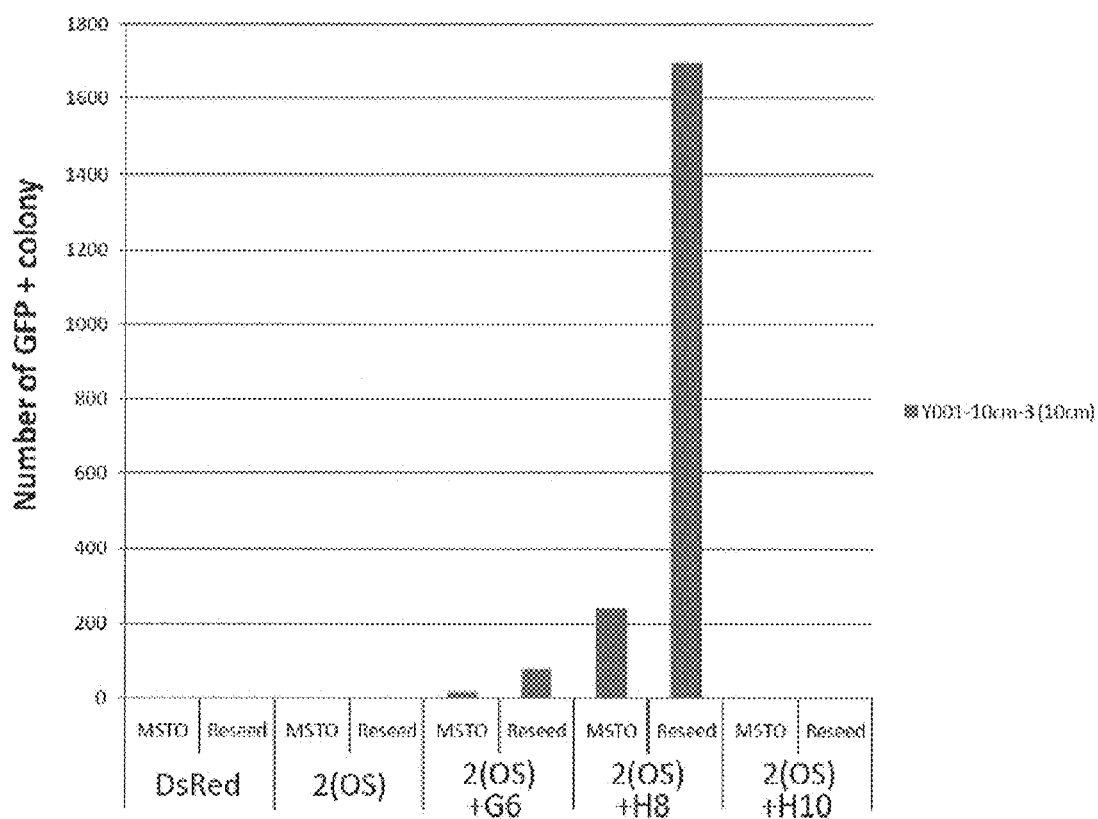
FIG. 18 is a graphic representation of the results of counting the number of colonies of iPS cells (GFP-positive cells) established by transferring a combination of 2 factors (Oct3/4, Sox2) and G6 (GLIS1), H8 (DMRTB1) or H10 (PITX2) into Nanog-GFP mouse MEF. The number of colonies established in 2(OS)+H10 was 1 for the MSTO method and 1 for the Reseed method.

The results of the above (4)-(6) are shown in FIG. 18 (result of 1 experiment). While no colonies were established using only 2 factors (Oct3/4, Sox2), colonies were established by adding the reprogramming factor of the present invention (GLIS1, DMRTB1 or PITX2). A particularly remarkable effect was observed when DMRTB1 was added.

GFP-positive colony image and the phase contrast image of respective iPS cells at the time of colony formation (P0), passage 1 (P1) and passage 2 (P2), are shown in FIG. 19.

Next, genome was extracted using QIAGEN "Gentra Puregene Cell Kit", and using a PCR enzyme (Takara Ex Taq), genomic-PCR was performed using the iPS cells established above. The results of the above (1)-(3) are shown in FIG. 20. In all iPS cells, it was confirmed that only the transfected genes were inserted into the genome and the genes that were not used for transfection were not inserted into the genome.

Next, RT-PCR analysis was performed using Rever Tra Ace kit (Takara). The results of the above (1)-(3) are shown in FIG. 21. The iPS cells established above, all expressed the ES cell specific marker genes Nanog, Oct3/4, Sox2, Rex1 and ECAT1. From these results, the cells that were established using the novel reprogramming factors were confirmed to be iPS cells.

Example 6

Production of Teratomas and Generation of Chimeric Mice

The following iPS cell clones which were established in the aforementioned Examples from the dermal fibroblasts of adult mice (Nanog-GFP mice), were used to produce teratomas.

G6-1 clone: established with the 3 factors, Oct3/4, Sox2, and G6 (GLIS1)

G6-6 clone: established with the 4 factors, Oct3/4, Sox2, c-Myc, and G6 (GLIS1)

H8-2 clone: established with the 4 factors, Oct3/4, Sox2, c-Myc, and H8 (DMRTB1)

H10 clone: established with the 4 factors, Oct3/4, Sox2, c-Myc, and H10 (PITX2)

The production of teratomas was carried out according to the method described in Cell, 126, 663-676 (2006). Specifically, $1 \times 10^6$ iPS cells were injected subcutaneously into immunodeficient mice, from which teratomas were isolated after 4 weeks. From these teratomas, genome was extracted in the same manner as described above, and genomic-PCR was performed using a PCR enzyme (Takara Ex Taq). The results are shown in FIG. 22. In all teratomas, it was confirmed that only the transfected genes were inserted into the genome and the genes that were not used for transfection were not inserted into the genome.

Next, these teratomas were cut and fixed in PBS(-) containing 4% formaldehyde. Paraffin embedded tissues were sliced and stained with hematoxylin-eosin. The results are shown in FIGS. 23 and 24. From a histological point of view, the tumors consisted of multiple types of cells, and since adipose tissue, striated muscular tissue, keratosis tissue, ciliated columnar epithelium tissue, nerve tissue, cartilage, collagen fiber tissue, smooth muscle tissue and the like were observed, the pluripotency of iPS cells was demonstrated.

Furthermore, as a result of microinjection of these iPS cells into blastocysts derived from ICR mouse, adult chimeras were generated.

Example 7

Microarray Analysis

DNA microarray analysis was performed to investigate whether there is a difference in gene expression between the iPS cells established using the novel reprogramming factors of the present invention (G6, H8, H10), and the iPS cells established using the conventional 4 factors (Oct3/4, Sox2, Klf4, c-Myc). Analysis was performed according to the technique described in Cell, 131, 861-872 (2007), using the iPS cells described below and total RNA derived from MEF.

K-G6: iPS cell established by transfection of the 4 genes, Oct3/4, Sox2, c-Myc and G6, into MEF (passage 5)

K-H8: iPS cell established by transfection of the 4 genes, Oct3/4, Sox2, c-Myc and H8, into MEF (passage 5)

K-H10: iPS cell established by the transfection of the 4 genes, Oct3/4, Sox2, c-Myc and H10, into MEF (passage 5)

4F: iPS cell established by the transfection of the 4 genes, Oct3/4, Sox2, c-Myc and Klf4, into MEF (passage 5)

MEF: MEF cell used for transfection (passage 1)

The results of the scatter plot are shown in FIGS. 25-27 (fold change line: 2-fold). Additionally, the correlation coefficient between each cell is shown in Table 2, and the result of clustering based on the correlation coefficient is shown in FIG. 28.

TABLE 2

| Array Name | K-G6-MEF | K-H8-MEF | K-H10-MEF | 4F-MEF | MEF |
|---|---|---|---|---|---|
| K-G6-MEF | 1 | 0.997012 | 0.99035835 | 0.9905535 | 0.8930298 |
| K-H8-MEF | 0.997012 | 1 | 0.9897563 | 0.9940246 | 0.89402026 |

TABLE 2-continued

| Array Name | K-G6-MEF | K-H8-MEF | K-H10-MEF | 4F-MEF | MEF |
|---|---|---|---|---|---|
| K-H10-MEF | 0.99035835 | 0.9897563 | 1 | 0.9888173 | 0.89811915 |
| 4F-MEF | 0.9905535 | 0.9940246 | 0.9888173 | 1 | 0.8940898 |
| MEF | 0.8930298 | 0.89402026 | 0.89811915 | 0.8940898 | 1 |

From the fact that the iPS cells that were established using the novel reprogramming factors of the present invention all showed gene expression patterns similar to those of the iPS cells that were established by using the conventional 4 factors, it was shown that the iPS cells of the present invention are comparable to the iPS cells that are established with the 4 factors, i.e., that the novel reprogramming factors of the present invention substitute Klf4.

Example 8

Establishment and Analysis of Human iPS Cells (1)

According to the method described in Takahashi, K. et al., Cell, 131: 861-872 (2007), mouse ecotropic virus receptor Slc7a1 gene was expressed in adult or neonatal human dermal fibroblasts (HDF) using lentiviruses (pLenti6/UbC-Slc7a1). 4 genes, Oct3/4, Sox2, c-Myc and G6 (GLIS1), were transfected into these cells ($1 \times 10^5$ cells/well, 6 well plate) using retroviruses, according to the method described in Takahashi, K. et al., Cell, 131: 861-872 (2007). Additionally, transfection of 4 genes, Oct3/4, Sox2, c-Myc and Klf4, was performed as a control.

The cells were collected 6 days after virus infection, and reseeded onto feeder cells ($5 \times 10^5$ cells/100 mm dish). mitomycin C treated SNL cells which have stopped cell division (McMahon, A. P. & Bradley, A. Cell 62, 1073-1085 (1990)) were used as the feeder cells. From the 7th day after infection, the cells were cultivated in a primate ES cell culture medium (ReproCELL) containing 4 ng/ml of recombinant human bFGF (WAKO). The colony image of the iPS cells around 35 days from infection is shown in FIG. 29, and the colony image of passage 2 iPS cells is shown in FIG. 30. iPS cells established with Oct3/4, Sox2, c-Myc and G6 (GLIS1) showed ES cell-like morphology that was similar to that of the iPS cells that were established with Oct3/4, Sox2, c-Myc and Klf4. Furthermore, they were positive for alkaline phosphatase activity.

Next, genome was extracted using QIAGEN "Gentra Puregene Cell Kit", and using a PCR enzyme (Takara Ex Taq), genomic-PCR was performed using the iPS cells established above. The results are shown in FIG. 31. In the established iPS cells, it was confirmed that only the transfected genes were inserted into the genome and the genes that were not used for transfection were not inserted into the genome.

Next, RT-PCR analysis was performed using Rever Tra Ace kit (Takara). The results are shown in FIG. 32. The established iPS cells all expressed the ES cell specific marker genes Oct3/4, Sox2 and Rex1. From these results, the cells that were established using the novel reprogramming factor G6 (GLIS1) were confirmed to be iPS cells.

Example 9

Establishment and Analysis of Human iPS Cells (2)

Using the same technique as Example 8, 3 genes, Oct3/4, Sox2 and H8 (DMRTB1), or 4 genes, Oct3/4, Sox2, c-Myc and H10 (PITX2), were transfected into dental pulp stem cells (J. Dent. Res., 87(7): 676-681 (2008)) using a retrovirus. In addition, 4 genes, Oct3/4, Sox2, c-Myc and Klf4, were transfected as a control.

Using the same technique as Example 8, colony image of the cultivated iPS cells around 35 days from infection is shown in FIG. 33, and the colony images of passage 1 iPS cells are shown in FIG. 34 (Oct3/4, Sox2, H8) and FIG. 37 (Oct3/4, Sox2, c-Myc, H10). The established iPS cells showed ES cell-like morphology that was similar to that of the iPS cells that were established with Oct3/4, Sox2, c-Myc and Klf4. Furthermore, they were positive for alkaline phosphatase activity.

Next, genome was extracted using QIAGEN "Gentra Puregene Cell Kit", and using a PCR enzyme (Takara Ex Taq), genomic-PCR was performed using the iPS cells established above. The results are shown in FIG. 35 (Oct3/4, Sox2, H8) and FIG. 38 (Oct3/4, Sox2, c-Myc, H10). In the established iPS cells, it was confirmed that only the transfected genes were inserted into the genome and the genes that were not used for transfection were not inserted into the genome.

Next, RT-PCR analysis was performed using Rever Tra Ace kit (Takara). The results are shown in FIG. 36 (Oct3/4, Sox2, H8) and FIG. 39 (Oct3/4, Sox2, c-Myc, H10). The established iPS cells expressed the ES cell specific marker genes Oct3/4, Sox2, Nanog and Rex1. From these results, the cells that were established using the novel reprogramming factors H8 (DMRTB1), and H10 (PITX2) were confirmed to be human iPS cells.

Example 10

Production of Teratomas

Human iPS cells established by the introduction of the 4 factors Oct3/4, Sox2, c-Myc and G6 (GLIS1) into HDF, were inserted into the testis of Scid mouse and tested for their pluripotent differentiation. Specifically, the aforementioned iPS cells were first cultivated in a primate ES cell culture medium (ReproCELL, Cosmo Bio) containing recombinant human bFGF (4 ng/ml) and Rho kinase inhibitor Y-27632 (10 µM). 1 hour later, the cells were treated with collagen IV and collected, and then recovered by centrifugation, and suspended in DMEM/F12 containing Y-27632 (10 µM). ¼ amount of the confluent cells (100 mm dish) was injected into the testis of a Scid mouse. 2-3 months later, the tumor was cut and fixed using PBS(−) containing 4% formaldehyde. Paraffin embedded tissue was sliced and stained with hematoxylin-eosin. The result is shown in FIG. 40. From a histological point of view, the tumor consisted of multiple types of cells, and since it had differentiated into 3 germ layers such as the cartilage, epithelia smooth muscle, epithelia, and nerve tissue, the pluripotency of iPS cells was demonstrated.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on U.S. provisional patent application Nos. 61/208,853 and 61/276,123, the contents of which are hereby incorporated by reference.

The invention claimed is:

1. A method of making induced pluripotent stem iPS cells, comprising the step of introducing a nuclear reprogramming substance into a somatic cell, wherein the nuclear reprogramming substance comprises the following (1), (2), (3), or (4):
   (1) Oct3/4, Sox2, and GLIS family zinc finger 1 (GLIS1), or nucleic acids that encode the same,
   (2) Oct3/4, Sox2, and DMRTB1, or nucleic acids that encode the same,
   (3) Oct3/4, Sox2, c-Myc, and iroquois homeobox protein 6 (IRX6), or nucleic acids that encode the same, or
   (4) Oct3/4, c-Myc, and paired-like homeodomain transcription factor 2 isoform b (PITX2), or nucleic acids that encode the same.

2. The method according to claim 1, wherein the nuclear reprogramming substance comprises Oct3/4, Sox2, and GLIS1, or nucleic acids that encode the same.

3. The method of according to claim 2, wherein the nuclear reprogramming substance further comprises c-Myc.

4. The method according to claim 1, wherein the nuclear reprogramming substance comprises Oct3/4, Sox2, and DMRTB1, or nucleic acids that encode the same.

5. The method according to claim 4, wherein the nuclear reprogramming substance further comprises c-Myc.

6. The method according to claim 1, wherein the nuclear reprogramming substance comprises Oct3/4, Sox2, c-Myc, and IRX6, or nucleic acids that encode the same.

7. The method according to claim 1, wherein the nuclear reprogramming substance comprises Oct3/4, c-Myc, and PITX2, or nucleic acids that encode the same.

8. The method according to claim 7, wherein the nuclear reprogramming substance further comprises Sox2.

9. An inducer of iPS cells from a somatic cell, comprising the nuclear reprogramming substance of the following (1), (2), (3), or (4):
   (1) Oct3/4, Sox2, and GLIS1, or nucleic acids that encode the same,
   (2) Oct3/4, Sox2, and DMRTB1, or nucleic acids that encode the same,
   (3) Oct3/4, Sox2, c-Myc, and IRX6, or nucleic acids that encode the same, or
   (4) Oct3/4, c-Myc, and PITX2, or nucleic acids that encode the same.

10. The inducer according to claim 9, wherein the nuclear reprogramming substance comprises Oct3/4, Sox2, and GLIS1, or nucleic acids that encode the same.

11. The inducer according to claim 10, wherein the nuclear reprogramming substance further comprises c-Myc.

12. The inducer according to claim 9, wherein the nuclear reprogramming substance comprises Oct3/4, Sox2, and DMRTB1, or nucleic acids that encode the same.

13. The inducer according to claim 12, wherein the nuclear reprogramming substance further comprises c-Myc.

14. The inducer according to claim 9, wherein the nuclear reprogramming substance comprises Oct3/4, Sox2, c-Myc, and IRX6, or nucleic acids that encode the same.

15. The inducer according to claim 9, wherein the nuclear reprogramming substance comprises Oct3/4, c-Myc, and PITX2, or nucleic acids that encode the same.

16. The inducer according to claim 15, wherein the nuclear reprogramming substance further comprises Sox2.

* * * * *

SEQUENCE LISTING

```
<160> NUMBER OF SEQ ID NOS: 19

<210> SEQ ID NO 1
<211> LENGTH: 2337
<212> TYPE: DNA
<213> ORGANISM: Homo sapiens
<220> FEATURE:
<221> NAME/KEY: CDS
<222> LOCATION: (534)..(1874)

<400> SEQUENCE: 1
gggtcagggt ttttgacgtt cctcgccagc tgcacaaacc tcccggagca agtgtgagtg      60
tgggtgagag tgcgcgcgcg cgcacgggct ggctgcgctt ggcacgcttg gtggcccagg     120
gtcccggggc ccggggtccc gtctggcggc ccgggattac cgtgacgtca cattgagcct     180
ctggccacct tggactggga cacctccgga gcctcacagc cccgcgccgc gccgcgcctc     240
acctcgccac cacgcgcctt tgggaacccg catcttcttc cttcccctgc ccatccatgg     300
gcccttctgt cttccggacc ccacgggccg gaggggcgcc ttccggagcg cagggctcgg     360
cagccgggct gccctcggct ctgcctccac tggggccaac caggcgaagg aaccggcgct     420
gggcatccgc agcggtgtaa ggaactgaga cacctcactg ctgggggcgc ggaacagctg     480
ggctgagacg ggaactcgac agggaagaga gagacgggcc agggacagcc acc atg       536
                                                            Met
                                                             1 tcc ttc cca cac ttt gga cac ccg tac cgc ggc gct tcc cag ttt ctg      584
Ser Phe Pro His Phe Gly His Pro Tyr Arg Gly Ala Ser Gln Phe Leu
            5                  10                  15 gcg tcg gca agt tcc agc acc aca tgc tgc gaa tct acc caa cgc tct      632
Ala Ser Ala Ser Ser Ser Thr Thr Cys Cys Glu Ser Thr Gln Arg Ser
        20                  25                  30 gtc tca gat gtg gca tca ggc tcc acc cca gcg ccc gct ctc tgc tgc      680
Val Ser Asp Val Ala Ser Gly Ser Thr Pro Ala Pro Ala Leu Cys Cys
    35                  40                  45 gca ccc tac gat agt cga ctg ctg ggc agt gcg cga ccg gag ctg ggc      728
Ala Pro Tyr Asp Ser Arg Leu Leu Gly Ser Ala Arg Pro Glu Leu Gly
50                  55                  60                  65 gcc gcc ttg ggc atc tat gga gca ccc tat gcg gcc gct gca gct gcc      776
Ala Ala Leu Gly Ile Tyr Gly Ala Pro Tyr Ala Ala Ala Ala Ala Ala
                70                  75                  80 cag agc tac cct ggc tac ctg ccc tat agc cca gag ccc ccc tca ctg      824
Gln Ser Tyr Pro Gly Tyr Leu Pro Tyr Ser Pro Glu Pro Pro Ser Leu
            85                  90                  95 tat ggg gca ctg aat cca cag tat gaa ttt aag gag gct gca ggg agt      872
Tyr Gly Ala Leu Asn Pro Gln Tyr Glu Phe Lys Glu Ala Ala Gly Ser
        100                 105                 110 ttt aca tcc agc ctg gca caa cca gga gcc tat tat ccc tat gag cgg      920
Phe Thr Ser Ser Leu Ala Gln Pro Gly Ala Tyr Tyr Pro Tyr Glu Arg
    115                 120                 125 act ctg ggg cag tac caa tat gaa cgg tat ggc gca gtg gaa ttg agt      968
Thr Leu Gly Gln Tyr Gln Tyr Glu Arg Tyr Gly Ala Val Glu Leu Ser
130                 135                 140                 145
```

```
ggc gcc ggt cgc cga aag aac gcg acc cgg gag acc acc agt aca ctc      1016
Gly Ala Gly Arg Arg Lys Asn Ala Thr Arg Glu Thr Thr Ser Thr Leu
            150                 155                 160 aag gcc tgg ctc aac gag cac cgc aaa aac ccc tac ccc act aag ggt      1064
Lys Ala Trp Leu Asn Glu His Arg Lys Asn Pro Tyr Pro Thr Lys Gly
        165                 170                 175 gag aag atc atg ctg gcc atc atc acc aag atg acc ctc acc cag gtg      1112
Glu Lys Ile Met Leu Ala Ile Ile Thr Lys Met Thr Leu Thr Gln Val
    180                 185                 190 tcc acc tgg ttc gcc aac gca cgc cgg cgc ctc aag aaa gag aac aaa      1160
Ser Thr Trp Phe Ala Asn Ala Arg Arg Arg Leu Lys Lys Glu Asn Lys
195                 200                 205 atg aca tgg gcg ccc aag aac aaa ggt ggg gag gag agg aag gca gag      1208
Met Thr Trp Ala Pro Lys Asn Lys Gly Gly Glu Glu Arg Lys Ala Glu
210                 215                 220                 225 gga gga gag gag gac tca cta ggc tgc cta act gct gac acc aaa gaa      1256
Gly Gly Glu Glu Asp Ser Leu Gly Cys Leu Thr Ala Asp Thr Lys Glu
            230                 235                 240 gtt act gct agc cag gag gcc cgg ggg ctc cgg ctg agt gac ctg gaa      1304
Val Thr Ala Ser Gln Glu Ala Arg Gly Leu Arg Leu Ser Asp Leu Glu
        245                 250                 255 gac ctg gag gaa gag gag gag gag gag gaa gct gaa gac gag gag          1352
Asp Leu Glu Glu Glu Glu Glu Glu Glu Glu Ala Glu Asp Glu Glu
    260                 265                 270 gta gtg gcc aca gct ggg gac agg ctg acg gag ttc cga aag ggc gcg      1400
Val Val Ala Thr Ala Gly Asp Arg Leu Thr Glu Phe Arg Lys Gly Ala
275                 280                 285 cag tca ctg cct ggg ccg tgc gct gca gct cga gag ggc cga ttg gag      1448
Gln Ser Leu Pro Gly Pro Cys Ala Ala Ala Arg Glu Gly Arg Leu Glu
290                 295                 300                 305 cgc agg gag tgc ggc ctg gct gcg ccc cgc ttc tcc ttc aat gac cct      1496
Arg Arg Glu Cys Gly Leu Ala Ala Pro Arg Phe Ser Phe Asn Asp Pro
            310                 315                 320 tcc gga tcg gaa gaa gct gac ttc ctc tcg gcg gag aca ggc agc cct      1544
Ser Gly Ser Glu Glu Ala Asp Phe Leu Ser Ala Glu Thr Gly Ser Pro
        325                 330                 335 agg ttg acc atg cac tac cca tgc ttg gag aaa ccg cgc atc tgg tct      1592
Arg Leu Thr Met His Tyr Pro Cys Leu Glu Lys Pro Arg Ile Trp Ser
    340                 345                 350 ctg gcg cac acc gcg aca gcc agc gct gtt gaa ggt gca ccc cca gcc      1640
Leu Ala His Thr Ala Thr Ala Ser Ala Val Glu Gly Ala Pro Pro Ala
355                 360                 365 cgg cct agg cca cga agt cct gag tgc cgt atg att cct gga cag cct      1688
Arg Pro Arg Pro Arg Ser Pro Glu Cys Arg Met Ile Pro Gly Gln Pro
370                 375                 380                 385 cct gcc tct gcc cgg cga ctc tca gtc ccc aga gac tcc gcg tgc gac      1736
Pro Ala Ser Ala Arg Arg Leu Ser Val Pro Arg Asp Ser Ala Cys Asp
            390                 395                 400 gag tct tcc tgc ata ccc aaa gcc ttt gga aac ccc aag ttt gcc ctg      1784
Glu Ser Ser Cys Ile Pro Lys Ala Phe Gly Asn Pro Lys Phe Ala Leu
        405                 410                 415 cag gga cta ccg ctg aac tgt gcg ccg tgc ccg cgg agg agc gag cct      1832
Gln Gly Leu Pro Leu Asn Cys Ala Pro Cys Pro Arg Arg Ser Glu Pro
    420                 425                 430 gta gtg cag tgc cag tac ccg tct gga gca gaa gca ggt tag              1874
Val Val Gln Cys Gln Tyr Pro Ser Gly Ala Glu Ala Gly
435                 440                 445 cgcaatggct gcgatttgcg aaagaatctt ggaaatgggc cccacgtttc gaattcatct    1934
```

```
ccaggttaag aagctgccag accttgccag ggaccaggag ctctcacttt gcctaagaga    1994
cagacacaca gaaaccctcc tagcagctgt ccttgcacgc agagctgggg tggtgggccg    2054
acttgaacct tagcagtccc cacgggagat ggcagggcac cttggggaag gccaagtggg    2114
aggctgggag gctgccccac ccaccgactc taccaagtct ctcttcctcc tgtggattca    2174
gcaaggcttc ctctcctgct caccctgtc tctcacctcc accaacccca ctcactttgt     2234
aacttcatca ctgacccggc caataaggac cctgtgcgtc ttctccccct cctaagccct    2294
tgtgtcctta aaataatca gtccgaaccc atgtaaaaaa aaa                       2337

<210> SEQ ID NO 2
<211> LENGTH: 446
<212> TYPE: PRT
<213> ORGANISM: Homo sapiens

<400> SEQUENCE: 2

Met Ser Phe Pro His Phe Gly His Pro Tyr Arg Gly Ala Ser Gln Phe
1               5                   10                  15

Leu Ala Ser Ala Ser Ser Ser Thr Thr Cys Cys Glu Ser Thr Gln Arg
            20                  25                  30

Ser Val Ser Asp Val Ala Ser Gly Ser Thr Pro Ala Pro Ala Leu Cys
        35                  40                  45

Cys Ala Pro Tyr Asp Ser Arg Leu Leu Gly Ser Ala Arg Pro Glu Leu
    50                  55                  60

Gly Ala Ala Leu Gly Ile Tyr Gly Ala Pro Tyr Ala Ala Ala Ala Ala
65                  70                  75                  80

Ala Gln Ser Tyr Pro Gly Tyr Leu Pro Tyr Ser Pro Glu Pro Pro Ser
                85                  90                  95

Leu Tyr Gly Ala Leu Asn Pro Gln Tyr Glu Phe Lys Glu Ala Ala Gly
            100                 105                 110

Ser Phe Thr Ser Ser Leu Ala Gln Pro Gly Ala Tyr Tyr Pro Tyr Glu
        115                 120                 125

Arg Thr Leu Gly Gln Tyr Gln Tyr Glu Arg Tyr Gly Ala Val Glu Leu
    130                 135                 140

Ser Gly Ala Gly Arg Arg Lys Asn Ala Thr Arg Glu Thr Thr Ser Thr
145                 150                 155                 160

Leu Lys Ala Trp Leu Asn Glu His Arg Lys Asn Pro Tyr Pro Thr Lys
                165                 170                 175

Gly Glu Lys Ile Met Leu Ala Ile Ile Thr Lys Met Thr Leu Thr Gln
            180                 185                 190

Val Ser Thr Trp Phe Ala Asn Ala Arg Arg Arg Leu Lys Lys Glu Asn
        195                 200                 205

Lys Met Thr Trp Ala Pro Lys Asn Lys Gly Gly Glu Glu Arg Lys Ala
    210                 215                 220

Glu Gly Gly Glu Glu Asp Ser Leu Gly Cys Leu Thr Ala Asp Thr Lys
225                 230                 235                 240

Glu Val Thr Ala Ser Gln Glu Ala Arg Gly Leu Arg Leu Ser Asp Leu
                245                 250                 255

Glu Asp Leu Glu Glu Glu Glu Glu Glu Glu Glu Ala Glu Asp Glu
            260                 265                 270

Glu Val Val Ala Thr Ala Gly Asp Arg Leu Thr Glu Phe Arg Lys Gly
        275                 280                 285

Ala Gln Ser Leu Pro Gly Pro Cys Ala Ala Ala Arg Glu Gly Arg Leu
    290                 295                 300
```

```
Glu Arg Arg Glu Cys Gly Leu Ala Ala Pro Arg Phe Ser Phe Asn Asp
305                 310                 315                 320

Pro Ser Gly Ser Glu Glu Ala Asp Phe Leu Ser Ala Glu Thr Gly Ser
            325                 330                 335

Pro Arg Leu Thr Met His Tyr Pro Cys Leu Glu Lys Pro Arg Ile Trp
                340                 345                 350

Ser Leu Ala His Thr Ala Thr Ala Ser Ala Val Glu Gly Ala Pro Pro
            355                 360                 365

Ala Arg Pro Arg Pro Arg Ser Pro Glu Cys Arg Met Ile Pro Gly Gln
370                 375                 380

Pro Pro Ala Ser Ala Arg Arg Leu Ser Val Pro Arg Asp Ser Ala Cys
385                 390                 395                 400

Asp Glu Ser Ser Cys Ile Pro Lys Ala Phe Gly Asn Pro Lys Phe Ala
            405                 410                 415

Leu Gln Gly Leu Pro Leu Asn Cys Ala Pro Cys Pro Arg Arg Ser Glu
            420                 425                 430

Pro Val Val Gln Cys Gln Tyr Pro Ser Gly Ala Glu Ala Gly
            435                 440                 445

<210> SEQ ID NO 3
<211> LENGTH: 2380
<212> TYPE: DNA
<213> ORGANISM: Mus musculus
<220> FEATURE:
<221> NAME/KEY: CDS
<222> LOCATION: (634)..(1953)

<400> SEQUENCE: 3
```

| | | |
|---|---|---|
| acttctcccg gggaatttgg agagggtctg tgtgcgcgcg cgcgcgtgag ctgcaggcga | 60 |
| aagagggtag gatctagcgg cgagtcgagg gtcagggtct ttgacgtttc tcgcccgttg | 120 |
| cacaaacctc gcagagcaag aacgagtgta tccgagagtg cgtgcatgta cacgggctgg | 180 |
| ctgcccttgg cacactcggt ggcccggggc cccggggccc gcggtcccct ctggcggccg | 240 |
| gggattaccg tgacgtcacg ttgagcctct ggccaccttg gactgggaca cctcgggaac | 300 |
| ctcacagccc gacgctgcgc tgtacctcac cttgccgctg cgcgcctttg caccctact | 360 |
| ccttcttcct aattctgccg ccgatccatg ggcccctctg cctctggaa cccacaggcc | 420 |
| gtaggggtgc cttaccaatc gcagaactcg gcagccctc tgcctttgat tctgcctccc | 480 |
| gtctctcccc tcctgccaac gaactggcgg ccagctcctg cagccctgta agaaaaccag | 540 |
| acgctgcgct gcgctgctgg ggtcatcgaa tcacagagct gagcaaggga ctcgaaagga | 600 |

```
aagagggact caagtccctg aagacgccct gct atg gcc ttt tca cct ttt gga       654
                                    Met Ala Phe Ser Pro Phe Gly
                                     1               5 cac ccg tat ggc agc aca tcc cag ttt ctg gtg tct gca agt tcc agt       702
His Pro Tyr Gly Ser Thr Ser Gln Phe Leu Val Ser Ala Ser Ser
         10                  15                  20 gcc act tgc tgc gaa acg gcc cct cgg cca gtg tca gat gtg gcc tca       750
Ala Thr Cys Cys Glu Thr Ala Pro Arg Pro Val Ser Asp Val Ala Ser
     25                  30                  35 gcc tcc acc tct gcc tct act ctt tgc tgt aca ccc tat gac agt cgg       798
Ala Ser Thr Ser Ala Ser Thr Leu Cys Cys Thr Pro Tyr Asp Ser Arg
 40                  45                  50                  55 ctg ctg ggc agt gct cgg cca gag ctg gga gct gcc ttg ggc atc tat       846
Leu Leu Gly Ser Ala Arg Pro Glu Leu Gly Ala Ala Leu Gly Ile Tyr
                 60                  65                  70 gga gca ccc tat gca gct gcc cag agt tac cct ggg tac ctg acc tat       894
```

```
       Gly Ala Pro Tyr Ala Ala Ala Gln Ser Tyr Pro Gly Tyr Leu Thr Tyr
                    75                  80                  85 ggc cca gag cca ccc aca ctg tgt ggc gca ctg aat cct cag tat gag          942
Gly Pro Glu Pro Pro Thr Leu Cys Gly Ala Leu Asn Pro Gln Tyr Glu
        90                  95                 100 ttc aag gat gct gca gga agc ttt gcc ccc agc ctg acc cag cca ggg          990
Phe Lys Asp Ala Ala Gly Ser Phe Ala Pro Ser Leu Thr Gln Pro Gly
        105                 110                115 gcc tac tac ccc tat gaa aca act ctg ggg cag tat caa tac gac agg         1038
Ala Tyr Tyr Pro Tyr Glu Thr Thr Leu Gly Gln Tyr Gln Tyr Asp Arg
120                 125                 130                135 tat ggc gga gtg gaa ttg agc agt gct ggc cgc agg aag aat gcc aca         1086
Tyr Gly Gly Val Glu Leu Ser Ser Ala Gly Arg Arg Lys Asn Ala Thr
                140                 145                 150 agg gag agc acc agc gca ctg aag gcc tgg ctc cac gag cac cgc aag         1134
Arg Glu Ser Thr Ser Ala Leu Lys Ala Trp Leu His Glu His Arg Lys
            155                 160                 165 aac ccg tac ccc acc aag ggc gag aag atc atg ctg gcc atc atc acc         1182
Asn Pro Tyr Pro Thr Lys Gly Glu Lys Ile Met Leu Ala Ile Ile Thr
        170                 175                 180 aag atg acc ctc acc cag gtg tcc acc tgg ttc gcc aac gcg cgc cgg         1230
Lys Met Thr Leu Thr Gln Val Ser Thr Trp Phe Ala Asn Ala Arg Arg
        185                 190                 195 cgc ctc aag aag gag aac aag atg aca tgg gcg ccc aag aac aag gga         1278
Arg Leu Lys Lys Glu Asn Lys Met Thr Trp Ala Pro Lys Asn Lys Gly
200                 205                 210                 215 ggg gag gag agg aaa gca gac agt gga gaa gac tct ctg gga tgc ctg         1326
Gly Glu Glu Arg Lys Ala Asp Ser Gly Glu Asp Ser Leu Gly Cys Leu
                220                 225                 230 aat ggt gac acc aaa gat gct act gcc agc cag gaa gcc cgg ggg ctg         1374
Asn Gly Asp Thr Lys Asp Ala Thr Ala Ser Gln Glu Ala Arg Gly Leu
            235                 240                 245 agg ctg agt gac ctg gaa gac ctg gag gaa gag gag gaa gag gaa gaa         1422
Arg Leu Ser Asp Leu Glu Asp Leu Glu Glu Glu Glu Glu Glu Glu Glu
        250                 255                 260 gca gag gag gag gca gcg gtc tca gca gca cgc agg ctg gcg gat ttt         1470
Ala Glu Glu Glu Ala Ala Val Ser Ala Ala Arg Arg Leu Ala Asp Phe
265                 270                 275 cag aag agc acg caa ccc ctg cct gct ccc tgc gcc gcc gcc cag gag         1518
Gln Lys Ser Thr Gln Pro Leu Pro Ala Pro Cys Ala Ala Ala Gln Glu
280                 285                 290                 295 aga tgc ttg gag agc aga gag tgc ggc ctg ggg cta ccc cgt ttc tct         1566
Arg Cys Leu Glu Ser Arg Glu Cys Gly Leu Gly Leu Pro Arg Phe Ser
                300                 305                 310 ttt act gag gcc cca caa tca ggg gaa gct gac ttc atc aca gca gag         1614
Phe Thr Glu Ala Pro Gln Ser Gly Glu Ala Asp Phe Ile Thr Ala Glu
            315                 320                 325 cca ggc ggc ccc acg atg atc tta cac tac cca agt ggc cac aaa ccc         1662
Pro Gly Gly Pro Thr Met Ile Leu His Tyr Pro Ser Gly His Lys Pro
        330                 335                 340 cgc att tgg tcc tta gct cac act gcg gca gcc agc gct gtc gaa agt         1710
Arg Ile Trp Ser Leu Ala His Thr Ala Ala Ala Ser Ala Val Glu Ser
        345                 350                 355 gct ccc tca act ccg ccc agg gca caa agt cca gag tgc cac atg att         1758
Ala Pro Ser Thr Pro Pro Arg Ala Gln Ser Pro Glu Cys His Met Ile
360                 365                 370                 375 ccc aga cag ccc agt tct atc agg cga ctc ctg gta ccc aga gac tcc         1806
Pro Arg Gln Pro Ser Ser Ile Arg Arg Leu Leu Val Pro Arg Asp Ser
                380                 385                 390
```

-continued

| | | | | | | | | | | | | | | | |
|---|---|---|---|---|---|---|---|---|---|---|---|---|---|---|---|
| gaa | ggc | gaa | gag | gat | tct | cct | gca | gcc | aaa | gct | ttt | gga | aac | tcc | acg | 1854 |
| Glu | Gly | Glu | Glu | Asp | Ser | Pro | Ala | Ala | Lys | Ala | Phe | Gly | Asn | Ser | Thr |
| | | 395 | | | | 400 | | | | | 405 | | | | |
| ttc | acc | ctg | cag | ggg | ctg | cca | ctg | aac | tgt | gca | cca | tac | ccg | agg | cgg | 1902 |
| Phe | Thr | Leu | Gln | Gly | Leu | Pro | Leu | Asn | Cys | Ala | Pro | Tyr | Pro | Arg | Arg |
| | 410 | | | | | 415 | | | | | 420 | | | | |
| aga | gag | cct | gaa | gtg | cgg | ttc | cag | tac | cca | tct | gga | gca | gaa | gca | ggt | 1950 |
| Arg | Glu | Pro | Glu | Val | Arg | Phe | Gln | Tyr | Pro | Ser | Gly | Ala | Glu | Ala | Gly |
| 425 | | | | | 430 | | | | | 435 | | | | | | tag tgcaatggct gcggtttgca gaagactttt ggaaatggct gcttccggat    2003 ccacattcat attaagaagt tccagacct tggcatggac tgggagctct cactttgcct    2063 gtgacaaaca cacagaacca tcctagctgt atcttgcacg caggactggg gacaggccag    2123 atgcacacaca cctcatcaga cttggaggag agaaggtggg agaccttggg ggaaagccct    2183 gtgtgtgctc acaggatact tgaccaagt ctctcttcct cccatgaatg gaggccctga    2243 gcagcatctc ctcctgctca cccacccctg cccagcccac tcactgtgta actttcttgc    2303 tgaaatggtc tccaaggact gtctgtgtct ccttcctctt ccccggctct accttcaaaa    2363 ataacttagc tgagtcc    2380

<210> SEQ ID NO 4
<211> LENGTH: 439
<212> TYPE: PRT
<213> ORGANISM: Mus musculus

<400> SEQUENCE: 4

Met Ala Phe Ser Pro Phe Gly His Pro Tyr Gly Ser Thr Ser Gln Phe
1               5                   10                  15

Leu Val Ser Ala Ser Ser Ala Thr Cys Cys Glu Thr Ala Pro Arg
            20                  25                  30

Pro Val Ser Asp Val Ala Ser Ala Ser Thr Ser Ala Ser Thr Leu Cys
        35                  40                  45

Cys Thr Pro Tyr Asp Ser Arg Leu Leu Gly Ser Ala Arg Pro Glu Leu
    50                  55                  60

Gly Ala Ala Leu Gly Ile Tyr Gly Ala Pro Tyr Ala Ala Ala Gln Ser
65                  70                  75                  80

Tyr Pro Gly Tyr Leu Thr Tyr Gly Pro Glu Pro Pro Thr Leu Cys Gly
                85                  90                  95

Ala Leu Asn Pro Gln Tyr Glu Phe Lys Asp Ala Ala Gly Ser Phe Ala
            100                 105                 110

Pro Ser Leu Thr Gln Pro Gly Ala Tyr Tyr Pro Tyr Glu Thr Thr Leu
        115                 120                 125

Gly Gln Tyr Gln Tyr Asp Arg Tyr Gly Gly Val Glu Leu Ser Ser Ala
    130                 135                 140

Gly Arg Arg Lys Asn Ala Thr Arg Glu Ser Thr Ser Ala Leu Lys Ala
145                 150                 155                 160

Trp Leu His Glu His Arg Lys Asn Pro Tyr Pro Thr Lys Gly Glu Lys
                165                 170                 175

Ile Met Leu Ala Ile Ile Thr Lys Met Thr Leu Thr Gln Val Ser Thr
            180                 185                 190

Trp Phe Ala Asn Ala Arg Arg Arg Leu Lys Lys Glu Asn Lys Met Thr
        195                 200                 205

Trp Ala Pro Lys Asn Lys Gly Gly Glu Glu Arg Lys Ala Asp Ser Gly
    210                 215                 220

Glu Asp Ser Leu Gly Cys Leu Asn Gly Asp Thr Lys Asp Ala Thr Ala

```
                225                 230                 235                 240
        Ser Gln Glu Ala Arg Gly Leu Arg Leu Ser Asp Leu Glu Asp Leu Glu
                        245                 250                 255

Glu Glu Glu Glu Glu Glu Ala Glu Glu Ala Ala Val Ser Ala
                        260                 265                 270

Ala Arg Arg Leu Ala Asp Phe Gln Lys Ser Thr Gln Pro Leu Pro Ala
                        275                 280                 285

Pro Cys Ala Ala Ala Gln Glu Arg Cys Leu Glu Ser Arg Glu Cys Gly
                290                 295                 300

Leu Gly Leu Pro Arg Phe Ser Phe Thr Glu Ala Pro Gln Ser Gly Glu
        305                 310                 315                 320

Ala Asp Phe Ile Thr Ala Glu Pro Gly Gly Pro Thr Met Ile Leu His
                        325                 330                 335

Tyr Pro Ser Gly His Lys Pro Arg Ile Trp Ser Leu Ala His Thr Ala
                        340                 345                 350

Ala Ala Ser Ala Val Glu Ser Ala Pro Ser Thr Pro Arg Ala Gln
                        355                 360                 365

Ser Pro Glu Cys His Met Ile Pro Arg Gln Pro Ser Ile Arg Arg
                370                 375                 380

Leu Leu Val Pro Arg Asp Ser Glu Gly Glu Asp Ser Pro Ala Ala
        385                 390                 395                 400

Lys Ala Phe Gly Asn Ser Thr Phe Thr Leu Gln Gly Leu Pro Leu Asn
                        405                 410                 415

Cys Ala Pro Tyr Pro Arg Arg Glu Pro Glu Val Arg Phe Gln Tyr
                        420                 425                 430

Pro Ser Gly Ala Glu Ala Gly
                    435

<210> SEQ ID NO 5
<211> LENGTH: 2816
<212> TYPE: DNA
<213> ORGANISM: Homo sapiens
<220> FEATURE:
<221> NAME/KEY: CDS
<222> LOCATION: (568)..(2430)

<400> SEQUENCE: 5
cactgtgtac tgagactgga tgcatccttg caataaaaaa gaggttgatc acgacaaatg        60 tgaacccgc cgttataaaa acagccatca tggctgtaaa tgccaaaaag cagtcagtct       120
tgtaacttga aaaaaaaaa aaaggaattg tagattgtgc gcatggactc ggagtggggg       180
cggtggacag taagtcatga tgtttggtg gtaccacctg gttgaatttc ttcatctgaa       240
taagaagctc ctgtgatgtt ctggggaggc cttggaaggc tagcgcatcc ctcatagaaa       300
gtgaatggga gctacggaca ccgtaccccg ggctcagaga agagcctgct ggacctggac       360
cttgctgagg gccctggccc cacctgctgc cagggcctgt ttctccctgc aggaagccca       420
ccgccccggg ctcaccccca gcttgtgag aggctgctgc atttccccca ccctgacagg       480
tcacctagac cccaggccac gtatgtgaac ggcagcctcc caaccacaca acacatcaaa       540
caggagtcct tgcccgacta ccaagcc atg gca gag gcc cgc aca tcc ctg tct       594
                                Met Ala Glu Ala Arg Thr Ser Leu Ser
                                  1               5 gcc cac tgt cgg ggc ccg ctg gcc act ggc ctg cac cca gac ctg gac       642
Ala His Cys Arg Gly Pro Leu Ala Thr Gly Leu His Pro Asp Leu Asp
 10                  15                  20                  25 ctc ccg ggc cga agc ctc gcc acc cct gcg cct tcc tgc tac ctt ctg       690
```

-continued

| | | | | | | | | | | | | | | |
|---|---|---|---|---|---|---|---|---|---|---|---|---|---|---|
| Leu | Pro | Gly | Arg | Ser | Leu | Ala | Thr | Pro | Ala | Pro | Ser | Cys | Tyr | Leu |
| | | | 30 | | | | 35 | | | | | 40 | | |

```
ggc agc gaa ccc agc tct ggc ctg ggc ctc cag ccc gag acc cac ctc      738
Gly Ser Glu Pro Ser Ser Gly Leu Gly Leu Gln Pro Glu Thr His Leu
         45                  50                  55 ccc gag ggc agc ctg aag cgg tgc tgc gtc ttg ggc cta ccc ccc acc      786
Pro Glu Gly Ser Leu Lys Arg Cys Cys Val Leu Gly Leu Pro Pro Thr
         60                  65                  70 tcc cca gcc tcc tcc tca ccc tgt gcc tcc tcc gac gtc acc tcc atc      834
Ser Pro Ala Ser Ser Ser Pro Cys Ala Ser Ser Asp Val Thr Ser Ile
         75                  80                  85 atc cgc tcc tcc cag acg tct ctg gtc acc tgt gta aat gga ctc cgg      882
Ile Arg Ser Ser Gln Thr Ser Leu Val Thr Cys Val Asn Gly Leu Arg
 90                  95                 100                 105 agc ccc cct ctg acg gga gat ctg ggg ggc cct tcc aag cgg gcc cgg      930
Ser Pro Pro Leu Thr Gly Asp Leu Gly Gly Pro Ser Lys Arg Ala Arg
                110                 115                 120 cct ggc cct gca tcg acg gac agc cat gag ggc agc ttg caa ctt gaa      978
Pro Gly Pro Ala Ser Thr Asp Ser His Glu Gly Ser Leu Gln Leu Glu
                125                 130                 135 gcc tgc cgg aag gcg agc ttc ctg aag cag gaa ccc gcg gat gag ttt     1026
Ala Cys Arg Lys Ala Ser Phe Leu Lys Gln Glu Pro Ala Asp Glu Phe
                140                 145                 150 tca gag ctc ttt ggg cct cac cag cag ggc ctg ccg ccc cct tat ccc     1074
Ser Glu Leu Phe Gly Pro His Gln Gln Gly Leu Pro Pro Pro Tyr Pro
        155                 160                 165 ctg tct cag ttg ccg cct ggc cca agc ctt gga ggc ctg ggg ctg ggc     1122
Leu Ser Gln Leu Pro Pro Gly Pro Ser Leu Gly Gly Leu Gly Leu Gly
170                 175                 180                 185 ctg gca ggc agg gtg gtg gcc ggg cgg cag gcg tgc cgc tgg gtg gac     1170
Leu Ala Gly Arg Val Val Ala Gly Arg Gln Ala Cys Arg Trp Val Asp
                190                 195                 200 tgt tgt gca gcc tat gag cag cag gag gag ctg gtg cgg cac atc gag     1218
Cys Cys Ala Ala Tyr Glu Gln Gln Glu Glu Leu Val Arg His Ile Glu
                205                 210                 215 aag agc cac atc gac cag cgc aag ggc gag gac ttc acc tgc ttc tgg     1266
Lys Ser His Ile Asp Gln Arg Lys Gly Glu Asp Phe Thr Cys Phe Trp
                220                 225                 230 gct ggc tgc gtg cgc cgc tac aag ccc ttc aac gcc cgc tac aag ctg     1314
Ala Gly Cys Val Arg Arg Tyr Lys Pro Phe Asn Ala Arg Tyr Lys Leu
        235                 240                 245 ctc atc cac atg cga gtg cac tcg ggc gag aag ccc aac aag tgc atg     1362
Leu Ile His Met Arg Val His Ser Gly Glu Lys Pro Asn Lys Cys Met
250                 255                 260                 265 ttt gaa ggc tgc agc aag gcc ttc tca cgg ctg gag aac ctc aag atc     1410
Phe Glu Gly Cys Ser Lys Ala Phe Ser Arg Leu Glu Asn Leu Lys Ile
                270                 275                 280 cac ctg agg agc cac acg ggc gag aag ccg tac ctg tgc cag cac ccg     1458
His Leu Arg Ser His Thr Gly Glu Lys Pro Tyr Leu Cys Gln His Pro
                285                 290                 295 ggt tgc cag aag gcc ttc agc aac tcc agc gac cgc gcc aag cac cag     1506
Gly Cys Gln Lys Ala Phe Ser Asn Ser Ser Asp Arg Ala Lys His Gln
                300                 305                 310 cgc acc cac cta gac acg aag ccg tac gcc tgt cag atc cct ggc tgc     1554
Arg Thr His Leu Asp Thr Lys Pro Tyr Ala Cys Gln Ile Pro Gly Cys
        315                 320                 325 tcc aag cgc tac aca gac ccc agc tcc ctc cgc aag cac gtc aag gcc     1602
Ser Lys Arg Tyr Thr Asp Pro Ser Ser Leu Arg Lys His Val Lys Ala
330                 335                 340                 345
```

-continued

| | |
|---|---|
| cat tca gcc aaa gag cag cag gtg cgt aag aag ctg cat gcg ggc cct<br>His Ser Ala Lys Glu Gln Gln Val Arg Lys Lys Leu His Ala Gly Pro<br>350 355 360 | 1650 |
| gac acc gag gcc gac gtc ctg acc gag tgt ctg gtc ctg cag cag ctc<br>Asp Thr Glu Ala Asp Val Leu Thr Glu Cys Leu Val Leu Gln Gln Leu<br>365 370 375 | 1698 |
| cac acg tcc aca cag ctg gct gcc agc gac ggc aag ggt ggc tgt ggc<br>His Thr Ser Thr Gln Leu Ala Ala Ser Asp Gly Lys Gly Gly Cys Gly<br>380 385 390 | 1746 |
| ctg ggc cag gag ctg ctc cca ggt gtg tat cct ggc tcc atc acc ccc<br>Leu Gly Gln Glu Leu Leu Pro Gly Val Tyr Pro Gly Ser Ile Thr Pro<br>395 400 405 | 1794 |
| cat aac gga ctt gca tcg ggc ctc ctg ccc cca gcg cac gac gta cct<br>His Asn Gly Leu Ala Ser Gly Leu Leu Pro Pro Ala His Asp Val Pro<br>410 415 420 425 | 1842 |
| tcc agg cac cac ccg ctg gat gcc acc acc agt tcc cac cac cat ctg<br>Ser Arg His His Pro Leu Asp Ala Thr Thr Ser Ser His His His Leu<br>430 435 440 | 1890 |
| tcc cct ctg ccc atg gct gag agc acc cgg gat ggg ttg ggg ccc ggc<br>Ser Pro Leu Pro Met Ala Glu Ser Thr Arg Asp Gly Leu Gly Pro Gly<br>445 450 455 | 1938 |
| ctc ctc tca cca ata gtc agc ccc ctg aag ggg ctg ggg cca ccg ccg<br>Leu Leu Ser Pro Ile Val Ser Pro Leu Lys Gly Leu Gly Pro Pro Pro<br>460 465 470 | 1986 |
| ctg ccc cca tcc tct cag agc cat tct ccg ggg ggc cag ccc ttc ccc<br>Leu Pro Pro Ser Ser Gln Ser His Ser Pro Gly Gly Gln Pro Phe Pro<br>475 480 485 | 2034 |
| aca ctc ccc agc aag ccg tcc tac cca ccc ttc cag agc cct cca ccc<br>Thr Leu Pro Ser Lys Pro Ser Tyr Pro Pro Phe Gln Ser Pro Pro Pro<br>490 495 500 505 | 2082 |
| ccg cct ctg ccc agc cca caa ggt tac cag ggc agt ttc cac tcc atc<br>Pro Pro Leu Pro Ser Pro Gln Gly Tyr Gln Gly Ser Phe His Ser Ile<br>510 515 520 | 2130 |
| cag agt tgc ttc ccc tat ggc gac tgc tac cgg atg gct gaa cca gca<br>Gln Ser Cys Phe Pro Tyr Gly Asp Cys Tyr Arg Met Ala Glu Pro Ala<br>525 530 535 | 2178 |
| gcc ggt ggg gac gga ctg gtc ggg gag acc cac ggt ttc aac ccc ctg<br>Ala Gly Gly Asp Gly Leu Val Gly Glu Thr His Gly Phe Asn Pro Leu<br>540 545 550 | 2226 |
| cgg ccc aat ggc tac cac agc ctc agc acg ccc ttg cct gcc aca ggc<br>Arg Pro Asn Gly Tyr His Ser Leu Ser Thr Pro Leu Pro Ala Thr Gly<br>555 560 565 | 2274 |
| tat gag gcc ctg gct gag gcc tca tgc ccc aca gcg ctg cca cag cag<br>Tyr Glu Ala Leu Ala Glu Ala Ser Cys Pro Thr Ala Leu Pro Gln Gln<br>570 575 580 585 | 2322 |
| cca tct gaa gat gtg gtg tcc agc ggc ccc gag gac tgt ggc ttc ttc<br>Pro Ser Glu Asp Val Val Ser Ser Gly Pro Glu Asp Cys Gly Phe Phe<br>590 595 600 | 2370 |
| ccc aat gga gcc ttt gac cac tgc ctg ggc cac atc ccc tcc atc tac<br>Pro Asn Gly Ala Phe Asp His Cys Leu Gly His Ile Pro Ser Ile Tyr<br>605 610 615 | 2418 |
| aca gac acc tga aggagccccc acatgcgcct gccatccag cactgcagat<br>Thr Asp Thr<br>620 | 2470 |
| gccacctcgc ccacctgctg tcgctcccac cctccgtgca cctagcagga gtgccaggcc | 2530 |
| acagccggaa cagccaggcc atgacccagg ggagccagcg ctgccacccc acccagcgct | 2590 |
| gccagggagc cgccatccga gcttgagctg ggcgcacaga ggtgcccgcc aggatctgtg | 2650 |
| gccctgtaac attccctcga tcttgtcttc ccgttcctcc ccgcagtggt tttgaaatca | 2710 |

```
cagacctcgt gtatataaaa tatgcagaac ttgtttccg ttccctgcc agttttatat      2770 ttttggtttt acaagaaaaa acattaaaaa ctggaaagga gatgtg                  2816
```

<210> SEQ ID NO 6
<211> LENGTH: 620
<212> TYPE: PRT
<213> ORGANISM: Homo sapiens

<400> SEQUENCE: 6

```
Met Ala Glu Ala Arg Thr Ser Leu Ser Ala His Cys Arg Gly Pro Leu
1               5                   10                  15

Ala Thr Gly Leu His Pro Asp Leu Asp Leu Pro Gly Arg Ser Leu Ala
            20                  25                  30

Thr Pro Ala Pro Ser Cys Tyr Leu Leu Gly Ser Glu Pro Ser Ser Gly
        35                  40                  45

Leu Gly Leu Gln Pro Glu Thr His Leu Pro Glu Gly Ser Leu Lys Arg
    50                  55                  60

Cys Cys Val Leu Gly Leu Pro Pro Thr Ser Pro Ala Ser Ser Ser Pro
65                  70                  75                  80

Cys Ala Ser Ser Asp Val Thr Ser Ile Ile Arg Ser Ser Gln Thr Ser
                85                  90                  95

Leu Val Thr Cys Val Asn Gly Leu Arg Ser Pro Pro Leu Thr Gly Asp
            100                 105                 110

Leu Gly Gly Pro Ser Lys Arg Ala Arg Pro Gly Pro Ala Ser Thr Asp
        115                 120                 125

Ser His Glu Gly Ser Leu Gln Leu Glu Ala Cys Arg Lys Ala Ser Phe
    130                 135                 140

Leu Lys Gln Glu Pro Ala Asp Glu Phe Ser Glu Leu Phe Gly Pro His
145                 150                 155                 160

Gln Gln Gly Leu Pro Pro Pro Tyr Pro Leu Ser Gln Leu Pro Pro Gly
                165                 170                 175

Pro Ser Leu Gly Gly Leu Gly Leu Gly Leu Ala Gly Arg Val Val Ala
            180                 185                 190

Gly Arg Gln Ala Cys Arg Trp Val Asp Cys Cys Ala Ala Tyr Glu Gln
        195                 200                 205

Gln Glu Glu Leu Val Arg His Ile Glu Lys Ser His Ile Asp Gln Arg
    210                 215                 220

Lys Gly Glu Asp Phe Thr Cys Phe Trp Ala Gly Cys Val Arg Arg Tyr
225                 230                 235                 240

Lys Pro Phe Asn Ala Arg Tyr Lys Leu Leu Ile His Met Arg Val His
                245                 250                 255

Ser Gly Glu Lys Pro Asn Lys Cys Met Phe Glu Gly Cys Ser Lys Ala
            260                 265                 270

Phe Ser Arg Leu Glu Asn Leu Lys Ile His Leu Arg Ser His Thr Gly
        275                 280                 285

Glu Lys Pro Tyr Leu Cys Gln His Pro Gly Cys Gln Lys Ala Phe Ser
    290                 295                 300

Asn Ser Ser Asp Arg Ala Lys His Gln Arg Thr His Leu Asp Thr Lys
305                 310                 315                 320

Pro Tyr Ala Cys Gln Ile Pro Gly Cys Ser Lys Arg Tyr Thr Asp Pro
                325                 330                 335

Ser Ser Leu Arg Lys His Val Lys Ala His Ser Ala Lys Glu Gln Gln
            340                 345                 350
```

Val Arg Lys Lys Leu His Ala Gly Pro Asp Thr Glu Ala Asp Val Leu
355                 360                 365

Thr Glu Cys Leu Val Leu Gln Gln Leu His Thr Ser Thr Gln Leu Ala
370                 375                 380

Ala Ser Asp Gly Lys Gly Gly Cys Gly Leu Gly Gln Glu Leu Leu Pro
385                 390                 395                 400

Gly Val Tyr Pro Gly Ser Ile Thr Pro His Asn Gly Leu Ala Ser Gly
                405                 410                 415

Leu Leu Pro Pro Ala His Asp Val Pro Ser Arg His Pro Leu Asp
        420                 425                 430

Ala Thr Thr Ser Ser His His His Leu Ser Pro Leu Pro Met Ala Glu
            435                 440                 445

Ser Thr Arg Asp Gly Leu Gly Pro Gly Leu Leu Ser Pro Ile Val Ser
    450                 455                 460

Pro Leu Lys Gly Leu Gly Pro Pro Leu Pro Pro Ser Ser Gln Ser
465                 470                 475                 480

His Ser Pro Gly Gly Gln Pro Phe Pro Thr Leu Pro Ser Lys Pro Ser
                485                 490                 495

Tyr Pro Pro Phe Gln Ser Pro Pro Pro Leu Pro Ser Pro Gln
            500                 505                 510

Gly Tyr Gln Gly Ser Phe His Ser Ile Gln Ser Cys Phe Pro Tyr Gly
        515                 520                 525

Asp Cys Tyr Arg Met Ala Glu Pro Ala Ala Gly Gly Asp Gly Leu Val
530                 535                 540

Gly Glu Thr His Gly Phe Asn Pro Leu Arg Pro Asn Gly Tyr His Ser
545                 550                 555                 560

Leu Ser Thr Pro Leu Pro Ala Thr Gly Tyr Glu Ala Leu Ala Glu Ala
                565                 570                 575

Ser Cys Pro Thr Ala Leu Pro Gln Gln Pro Ser Glu Asp Val Val Ser
            580                 585                 590

Ser Gly Pro Glu Asp Cys Gly Phe Phe Pro Asn Gly Ala Phe Asp His
        595                 600                 605

Cys Leu Gly His Ile Pro Ser Ile Tyr Thr Asp Thr
610                 615                 620

<210> SEQ ID NO 7
<211> LENGTH: 2904
<212> TYPE: DNA
<213> ORGANISM: Mus musculus
<220> FEATURE:
<221> NAME/KEY: CDS
<222> LOCATION: (222)..(2591)

<400> SEQUENCE: 7
ggggacccag tggcgtccga atccgggagc tctggggtgg cgcggggctc gccgaggggc      60
gaggcgaatt tggggccct gaggcctcgc tctcgcggga atgatgctgg aaatgatgct     120
gaggctccgg cgtgagactt gcggctgccg gcggagcgga gtgtgagccg gtgaatgggg    180
agcctggcgc gaccccagc cgtgcgcccc gccccggcgc c atg cat tgc gag gtg    236
                                              Met His Cys Glu Val
                                              1               5 gcc gag gca ctt tcg gac aag agg cca aag gag gcc cct ggt gct cct    284
Ala Glu Ala Leu Ser Asp Lys Arg Pro Lys Glu Ala Pro Gly Ala Pro
            10                  15                  20 ggc cag ggc cgc ggg cct gtc agc ctg gga gcg cac atg gcc ttc agg    332
Gly Gln Gly Arg Gly Pro Val Ser Leu Gly Ala His Met Ala Phe Arg
        25                  30                  35

```
att gct gtg agt ggt ggc ggc tgc ggg gac ggg aac ccg cta gac ctg      380
Ile Ala Val Ser Gly Gly Gly Cys Gly Asp Gly Asn Pro Leu Asp Leu
        40                  45                  50 ctg cct cgg cta ccg gtg cca cca cca cgt gcc cac gat ctc ctt cgg      428
Leu Pro Arg Leu Pro Val Pro Pro Pro Arg Ala His Asp Leu Leu Arg
55                  60                  65 ccc cgg agc cct cga gac tat ggt gtg tcc aag acc ggc agc ggg aag      476
Pro Arg Ser Pro Arg Asp Tyr Gly Val Ser Lys Thr Gly Ser Gly Lys
70                  75                  80                  85 gtg aac ggg agc tac ggg cac agc tca gag aag agc ctg ctg gac ctg      524
Val Asn Gly Ser Tyr Gly His Ser Ser Glu Lys Ser Leu Leu Asp Leu
                90                  95                  100 gac ctg gcc gag ggt ccc agc ccc tcc tgc cac cag ggt ctg ttt ctt      572
Asp Leu Ala Glu Gly Pro Ser Pro Ser Cys His Gln Gly Leu Phe Leu
                105                 110                 115 cct gca ggg acc cca cca ccc cgg ggt cac ccc cct gtc tgt gag aag      620
Pro Ala Gly Thr Pro Pro Pro Arg Gly His Pro Pro Val Cys Glu Lys
            120                 125                 130 ctg ctg cac ttc ccc cac cca aac agg tca ccc aga cct cag gct acg      668
Leu Leu His Phe Pro His Pro Asn Arg Ser Pro Arg Pro Gln Ala Thr
    135                 140                 145 ttt gtg aac ggc agc ctc cca gcc gct cag cac atc aag caa gaa gcc      716
Phe Val Asn Gly Ser Leu Pro Ala Ala Gln His Ile Lys Gln Glu Ala
150                 155                 160                 165 cta ccg gac tac cag gcc atg gtc agc gcc cac aca ccc ctg ccc acc      764
Leu Pro Asp Tyr Gln Ala Met Val Ser Ala His Thr Pro Leu Pro Thr
                170                 175                 180 cac tgc cga gcc cca tcg tcc atg ggt ctg ccc tca gac ctg gac ttt      812
His Cys Arg Ala Pro Ser Ser Met Gly Leu Pro Ser Asp Leu Asp Phe
                185                 190                 195 cca gac cga ggc ctc acc aac cct gca cct tcc tgc tac ctt ctg ggc      860
Pro Asp Arg Gly Leu Thr Asn Pro Ala Pro Ser Cys Tyr Leu Leu Gly
            200                 205                 210 aat gaa ccc atc tca gac ctg ggt ccc caa ccc gag gcc cac ctc ccc      908
Asn Glu Pro Ile Ser Asp Leu Gly Pro Gln Pro Glu Ala His Leu Pro
    215                 220                 225 gag ggc agc ctg aaa cgc tgc tgc ctc ctg ggc ctg ccc ccc acc tct      956
Glu Gly Ser Leu Lys Arg Cys Cys Leu Leu Gly Leu Pro Pro Thr Ser
230                 235                 240                 245 tca gcc tcc tcc tca ccc tgt gcc tcc tca gat atc aat cct gtc atc     1004
Ser Ala Ser Ser Ser Pro Cys Ala Ser Ser Asp Ile Asn Pro Val Ile
                250                 255                 260 cac tcc tcc cag aca gct cta gtt agc tgt gta aat gga ctc cga agc     1052
His Ser Ser Gln Thr Ala Leu Val Ser Cys Val Asn Gly Leu Arg Ser
                265                 270                 275 cca cct ctg ccg gga gac ctg ggg ggc cct ccc aag cgg tca cgg ccc     1100
Pro Pro Leu Pro Gly Asp Leu Gly Gly Pro Pro Lys Arg Ser Arg Pro
            280                 285                 290 ggg cct gca tcc agt gac ggc cag gag ggc agc ttg cag ctt gaa gca     1148
Gly Pro Ala Ser Ser Asp Gly Gln Glu Gly Ser Leu Gln Leu Glu Ala
    295                 300                 305 tgc cgg aag tca ggc ttc ctg aag cag gag ccc atg gac gag ttt tca     1196
Cys Arg Lys Ser Gly Phe Leu Lys Gln Glu Pro Met Asp Glu Phe Ser
310                 315                 320                 325 gag ctt ttt gct cca cac cac cag ggt ttg cca ccc cct tac ccc ttg     1244
Glu Leu Phe Ala Pro His His Gln Gly Leu Pro Pro Pro Tyr Pro Leu
                330                 335                 340 cct cag ttg cca act ggc ccc ggc ctc gga ggc cta ggg ctg ggc ctg     1292
Pro Gln Leu Pro Thr Gly Pro Gly Leu Gly Gly Leu Gly Leu Gly Leu
```

```
                    345                 350                 355
gca ggt agg atg gtt gcc ggt cgg cag gca tgc cgc tgg gtg gac tgc    1340
Ala Gly Arg Met Val Ala Gly Arg Gln Ala Cys Arg Trp Val Asp Cys
            360                 365                 370 tgc gca gcc tac gag cag cag gag gag ctg gtg cgg cac atc gag aag    1388
Cys Ala Ala Tyr Glu Gln Gln Glu Glu Leu Val Arg His Ile Glu Lys
375                 380                 385 agc cac atc gac cag cgc aag ggc gaa gac ttc acc tgc ttc tgg gcc    1436
Ser His Ile Asp Gln Arg Lys Gly Glu Asp Phe Thr Cys Phe Trp Ala
390                 395                 400                 405 ggg tgt gtg cgg cgc tac aag ccc ttc aat gcc cgc tac aag ctg ctc    1484
Gly Cys Val Arg Arg Tyr Lys Pro Phe Asn Ala Arg Tyr Lys Leu Leu
                410                 415                 420 atc cac atg agg gta cac tca ggc gag aag ccc aac aag tgc atg ttc    1532
Ile His Met Arg Val His Ser Gly Glu Lys Pro Asn Lys Cys Met Phe
                425                 430                 435 gaa ggc tgc agt aaa gcc ttt tcc cgt ctg gag aac ctg aag atc cat    1580
Glu Gly Cys Ser Lys Ala Phe Ser Arg Leu Glu Asn Leu Lys Ile His
                440                 445                 450 ctg cgg agc cac aca ggc gag aaa cca tac ctg tgc cag cac cca ggc    1628
Leu Arg Ser His Thr Gly Glu Lys Pro Tyr Leu Cys Gln His Pro Gly
455                 460                 465 tgc cag aag gcc ttc agc aac tcc agc gac cgt gcc aag cac caa cgc    1676
Cys Gln Lys Ala Phe Ser Asn Ser Ser Asp Arg Ala Lys His Gln Arg
470                 475                 480                 485 acc cac ctc gac acg aag cca tat gct tgt cag atc cct ggc tgc tcc    1724
Thr His Leu Asp Thr Lys Pro Tyr Ala Cys Gln Ile Pro Gly Cys Ser
                490                 495                 500 aag cgc tac acg gac ccc agc tcc ctc cgc aag cac gtg aag gcc cac    1772
Lys Arg Tyr Thr Asp Pro Ser Ser Leu Arg Lys His Val Lys Ala His
                505                 510                 515 tca gcc aaa gag cag cag gtg cgt aag aag ctg cac aca ggt gcc gac    1820
Ser Ala Lys Glu Gln Gln Val Arg Lys Lys Leu His Thr Gly Ala Asp
                520                 525                 530 cca gag gct gat gtt ctg tcc gag tgt ctg tcc ctg cag cag ctc caa    1868
Pro Glu Ala Asp Val Leu Ser Glu Cys Leu Ser Leu Gln Gln Leu Gln
535                 540                 545 gca tcc aca ctg ttg ccg gcc agc aga ggg aag ggc agc caa acc ctg    1916
Ala Ser Thr Leu Leu Pro Ala Ser Arg Gly Lys Gly Ser Gln Thr Leu
550                 555                 560                 565 agc cag gag ctc ctc cca ggt gtg tat cct ggc tcc gtc acc cca caa    1964
Ser Gln Glu Leu Leu Pro Gly Val Tyr Pro Gly Ser Val Thr Pro Gln
                570                 575                 580 aac ggg ctt gct tca ggc atc ctg tcc ccc tcc cac gat gtc cct tcc    2012
Asn Gly Leu Ala Ser Gly Ile Leu Ser Pro Ser His Asp Val Pro Ser
                585                 590                 595 agg cac cac cca ctg gag gtc ccc act ggt tcc cac cac cac ctg tcc    2060
Arg His His Pro Leu Glu Val Pro Thr Gly Ser His His His Leu Ser
                600                 605                 610 cct ctg ccc aca gct gag agc acc agg gat ggc ctg ggg ccc agt ctc    2108
Pro Leu Pro Thr Ala Glu Ser Thr Arg Asp Gly Leu Gly Pro Ser Leu
                615                 620                 625 ctt tca ccc atg gtc agc cca ctg aag ggg ctt ggt cca cca ccg cta    2156
Leu Ser Pro Met Val Ser Pro Leu Lys Gly Leu Gly Pro Pro Pro Leu
630                 635                 640                 645 cca cca gcc tcc cag agt cag tct cca ggg gga cag tca ttc tct aca    2204
Pro Pro Ala Ser Gln Ser Gln Ser Pro Gly Gly Gln Ser Phe Ser Thr
                650                 655                 660 gtc ccc agc aag cct acc tac cca tcc ttc caa agc cca cca cct ctg    2252
```

-continued

```
Val Pro Ser Lys Pro Thr Tyr Pro Ser Phe Gln Ser Pro Pro Pro Leu
            665                 670                 675 ccc agc ccc caa ggc tac caa ggc agt ttc cat tcc atc cag aac tgc      2300
Pro Ser Pro Gln Gly Tyr Gln Gly Ser Phe His Ser Ile Gln Asn Cys
680                 685                 690 ttc ccc tac gct gac tgc tac cgg gcc act gag cca gca gcc tcc agg      2348
Phe Pro Tyr Ala Asp Cys Tyr Arg Ala Thr Glu Pro Ala Ala Ser Arg
    695                 700                 705 gat gga ctg gtg ggt gat gcc cac ggt ttc aac ccc ttg cga ccc agc      2396
Asp Gly Leu Val Gly Asp Ala His Gly Phe Asn Pro Leu Arg Pro Ser
710                 715                 720                 725 aca tac tcc agc ctc agc aca cct tta tcc gca cca ggc tac gag acc      2444
Thr Tyr Ser Ser Leu Ser Thr Pro Leu Ser Ala Pro Gly Tyr Glu Thr
                730                 735                 740 ctg gca gaa acg ccg tgt ccc cca gcg ctg cag cca cag cca gct gaa      2492
Leu Ala Glu Thr Pro Cys Pro Pro Ala Leu Gln Pro Gln Pro Ala Glu
            745                 750                 755 gac ctg gta cct agt ggt cct gag gac tgt ggc ttc ttc ccc aat ggg      2540
Asp Leu Val Pro Ser Gly Pro Glu Asp Cys Gly Phe Phe Pro Asn Gly
        760                 765                 770 gcc ttt gac cac tgt ctg agt cac atc ccg tcc atc tac act gac acc      2588
Ala Phe Asp His Cys Leu Ser His Ile Pro Ser Ile Tyr Thr Asp Thr
775                 780                 785 tga aggaagggc gctgctctgc ctgcctgcct ggctcctgag ctacttcacc            2641
tacctgccat ctgctggtgc ttcccacacg gggcagcaag ccacaccac agggtacttc    2701 cctacctgga gggctgtctg gtccagagct gcctgccagg agctatggcc ctctgacagc   2761
cccatggctg tgtcttcctc tctctccata aggttctcaa atcacagacc tcgtgtatat   2821
acaatgtaca ggacctcttt tccgccgccc tgcaagtttt atattttttgg ttttacaaga  2881 aaaacattaa aaactggaaa cta                                            2904

<210> SEQ ID NO 8
<211> LENGTH: 789
<212> TYPE: PRT
<213> ORGANISM: Mus musculus

<400> SEQUENCE: 8

Met His Cys Glu Val Ala Glu Ala Leu Ser Asp Lys Arg Pro Lys Glu
1               5                   10                  15

Ala Pro Gly Ala Pro Gly Gln Gly Arg Gly Pro Val Ser Leu Gly Ala
            20                  25                  30

His Met Ala Phe Arg Ile Ala Val Ser Gly Gly Cys Gly Asp Gly
        35                  40                  45

Asn Pro Leu Asp Leu Leu Pro Arg Leu Pro Val Pro Pro Arg Ala
    50                  55                  60

His Asp Leu Leu Arg Pro Arg Ser Pro Arg Asp Tyr Gly Val Ser Lys
65                  70                  75                  80

Thr Gly Ser Gly Lys Val Asn Gly Ser Tyr Gly His Ser Ser Glu Lys
                85                  90                  95

Ser Leu Leu Asp Leu Asp Leu Ala Glu Gly Pro Ser Pro Ser Cys His
            100                 105                 110

Gln Gly Leu Phe Leu Pro Ala Gly Thr Pro Pro Arg Gly His Pro
        115                 120                 125

Pro Val Cys Glu Lys Leu Leu His Phe Pro His Pro Asn Arg Ser Pro
    130                 135                 140

Arg Pro Gln Ala Thr Phe Val Asn Gly Ser Leu Pro Ala Ala Gln His
```

```
            145                 150                 155                 160
        Ile Lys Gln Glu Ala Leu Pro Asp Tyr Gln Ala Met Val Ser Ala His
                        165                 170                 175
        Thr Pro Leu Pro Thr His Cys Arg Ala Pro Ser Ser Met Gly Leu Pro
                        180                 185                 190
        Ser Asp Leu Asp Phe Pro Asp Arg Gly Leu Thr Asn Pro Ala Pro Ser
                        195                 200                 205
        Cys Tyr Leu Leu Gly Asn Glu Pro Ile Ser Asp Leu Gly Pro Gln Pro
                        210                 215                 220
        Glu Ala His Leu Pro Glu Gly Ser Leu Lys Arg Cys Cys Leu Leu Gly
        225                 230                 235                 240
        Leu Pro Pro Thr Ser Ala Ser Ser Pro Cys Ala Ser Ser Asp
                        245                 250                 255
        Ile Asn Pro Val Ile His Ser Ser Gln Thr Ala Leu Val Ser Cys Val
                        260                 265                 270
        Asn Gly Leu Arg Ser Pro Pro Leu Pro Gly Asp Leu Gly Gly Pro Pro
                        275                 280                 285
        Lys Arg Ser Arg Pro Gly Pro Ala Ser Ser Asp Gly Gln Glu Gly Ser
                        290                 295                 300
        Leu Gln Leu Glu Ala Cys Arg Lys Ser Gly Phe Leu Lys Gln Glu Pro
        305                 310                 315                 320
        Met Asp Glu Phe Ser Glu Leu Phe Ala Pro His His Gln Gly Leu Pro
                        325                 330                 335
        Pro Pro Tyr Pro Leu Pro Gln Leu Pro Thr Gly Pro Gly Leu Gly Gly
                        340                 345                 350
        Leu Gly Leu Gly Leu Ala Gly Arg Met Val Ala Gly Arg Gln Ala Cys
                        355                 360                 365
        Arg Trp Val Asp Cys Cys Ala Ala Tyr Glu Gln Gln Glu Glu Leu Val
                        370                 375                 380
        Arg His Ile Glu Lys Ser His Ile Asp Gln Arg Lys Gly Glu Asp Phe
        385                 390                 395                 400
        Thr Cys Phe Trp Ala Gly Cys Val Arg Arg Tyr Lys Pro Phe Asn Ala
                        405                 410                 415
        Arg Tyr Lys Leu Leu Ile His Met Arg Val His Ser Gly Glu Lys Pro
                        420                 425                 430
        Asn Lys Cys Met Phe Glu Gly Cys Ser Lys Ala Phe Ser Arg Leu Glu
                        435                 440                 445
        Asn Leu Lys Ile His Leu Arg Ser His Thr Gly Glu Lys Pro Tyr Leu
                        450                 455                 460
        Cys Gln His Pro Gly Cys Gln Lys Ala Phe Ser Asn Ser Ser Asp Arg
        465                 470                 475                 480
        Ala Lys His Gln Arg Thr His Leu Asp Thr Lys Pro Tyr Ala Cys Gln
                        485                 490                 495
        Ile Pro Gly Cys Ser Lys Arg Tyr Thr Asp Pro Ser Ser Leu Arg Lys
                        500                 505                 510
        His Val Lys Ala His Ser Ala Lys Glu Gln Gln Val Arg Lys Lys Leu
                        515                 520                 525
        His Thr Gly Ala Asp Pro Glu Ala Asp Val Leu Ser Glu Cys Leu Ser
                        530                 535                 540
        Leu Gln Gln Leu Gln Ala Ser Thr Leu Leu Pro Ala Ser Arg Gly Lys
        545                 550                 555                 560
        Gly Ser Gln Thr Leu Ser Gln Glu Leu Leu Pro Gly Val Tyr Pro Gly
                        565                 570                 575
```

```
Ser Val Thr Pro Gln Asn Gly Leu Ala Ser Gly Ile Leu Ser Pro Ser
            580                 585                 590

His Asp Val Pro Ser Arg His His Pro Leu Glu Val Pro Thr Gly Ser
        595                 600                 605

His His His Leu Ser Pro Leu Pro Thr Ala Glu Ser Thr Arg Asp Gly
    610                 615                 620

Leu Gly Pro Ser Leu Leu Ser Pro Met Val Ser Pro Lys Gly Leu
625                 630                 635                 640

Gly Pro Pro Pro Leu Pro Pro Ala Ser Gln Ser Gln Ser Pro Gly Gly
                645                 650                 655

Gln Ser Phe Ser Thr Val Pro Ser Lys Pro Thr Tyr Pro Ser Phe Gln
            660                 665                 670

Ser Pro Pro Pro Leu Pro Ser Pro Gln Gly Tyr Gln Gly Ser Phe His
        675                 680                 685

Ser Ile Gln Asn Cys Phe Pro Tyr Ala Asp Cys Tyr Arg Ala Thr Glu
    690                 695                 700

Pro Ala Ala Ser Arg Asp Gly Leu Val Gly Asp Ala His Gly Phe Asn
705                 710                 715                 720

Pro Leu Arg Pro Ser Thr Tyr Ser Ser Leu Ser Thr Pro Leu Ser Ala
                725                 730                 735

Pro Gly Tyr Glu Thr Leu Ala Glu Thr Pro Cys Pro Ala Leu Gln
            740                 745                 750

Pro Gln Pro Ala Glu Asp Leu Val Pro Ser Gly Pro Glu Asp Cys Gly
        755                 760                 765

Phe Phe Pro Asn Gly Ala Phe Asp His Cys Leu Ser His Ile Pro Ser
    770                 775                 780

Ile Tyr Thr Asp Thr
785

<210> SEQ ID NO 9
<211> LENGTH: 2250
<212> TYPE: DNA
<213> ORGANISM: Homo sapiens
<220> FEATURE:
<221> NAME/KEY: CDS
<222> LOCATION: (583)..(1536)

<400> SEQUENCE: 9
tgggagtccg tgctcctgct cctcggttgg ctcctaagtg ccccgccagg tccctctcc      60 tttcgctctc ccggctccgg ctcccgactc ttcggcccgc tggcatctgc ttccctcccc    120
tgcctcgttt ctcgtcgccc ctgctcgctc ccccggcgc tcgcccgggc gctgtgctcg    180
ctcctggatc gccagccgcg cagccgggct cggccggccg cccgcgcgcc actgtgcagt    240
ggagtttggt ggaatctctg ctgacgtcac gtcactcccc acacggagta ggagcagagg    300
gaagagagag ggatgagagg gagggagagg agagagagtg cgagaccgag cgagaaagct    360
ggagaggagc agaaagaaac tgccagtggc ggctagattt cggaggcccc agtgcacccg    420
tggactcctt cggaacttgg caccctcagg agccctgcag tcctctcagg cccggctttc    480
gggcgcttgc cgtgcagccg gaggctcggc tcgctggaaa tcgccccggg aagcagtggg    540
acgcggagac agcagctctc tcccggtagc cgataacggg ga atg gag acc aac      594
                                                Met Glu Thr Asn
                                                  1 tgc cgc aaa ctg gtg tcg gcg tgt gtg caa tta ggc gtg cag ccg gcg    642
Cys Arg Lys Leu Val Ser Ala Cys Val Gln Leu Gly Val Gln Pro Ala
  5              10                  15                  20
```

```
gcc gtt gaa tgt ctc ttc tcc aaa gac tcc gaa atc aaa aag gtc gag    690
Ala Val Glu Cys Leu Phe Ser Lys Asp Ser Glu Ile Lys Lys Val Glu
            25                  30                  35 ttc acg gac tct cct gag agc cga aaa gag gca gcc agc agc aag ttc    738
Phe Thr Asp Ser Pro Glu Ser Arg Lys Glu Ala Ala Ser Ser Lys Phe
        40                  45                  50 ttc ccg cgg cag cat cct ggc gcc aat gag aaa gat aaa agc cag cag    786
Phe Pro Arg Gln His Pro Gly Ala Asn Glu Lys Asp Lys Ser Gln Gln
    55                  60                  65 ggg aag aat gag gac gtg ggc gcc gag gac ccg tct aag aag aag cgg    834
Gly Lys Asn Glu Asp Val Gly Ala Glu Asp Pro Ser Lys Lys Lys Arg
70                  75                  80 caa agg cgg cag cgg act cac ttt acc agc cag cag ctc cag gag ctg    882
Gln Arg Arg Gln Arg Thr His Phe Thr Ser Gln Gln Leu Gln Glu Leu
85                  90                  95                 100 gag gcc act ttc cag agg aac cgc tac ccg gac atg tcc aca cgc gaa    930
Glu Ala Thr Phe Gln Arg Asn Arg Tyr Pro Asp Met Ser Thr Arg Glu
            105                 110                 115 gaa atc gct gtg tgg acc aac ctt acg gaa gcc cga gtc cgg gtt tgg    978
Glu Ile Ala Val Trp Thr Asn Leu Thr Glu Ala Arg Val Arg Val Trp
        120                 125                 130 ttc aag aat cgt cgg gcc aaa tgg aga aag agg gag cgc aac cag cag   1026
Phe Lys Asn Arg Arg Ala Lys Trp Arg Lys Arg Glu Arg Asn Gln Gln
    135                 140                 145 gcc gag cta tgc aag aat ggc ttc ggg ccg cag ttc aat ggg ctc atg   1074
Ala Glu Leu Cys Lys Asn Gly Phe Gly Pro Gln Phe Asn Gly Leu Met
150                 155                 160 cag ccc tac gac gac atg tac cca ggc tat tcc tac aac aac tgg gcc   1122
Gln Pro Tyr Asp Asp Met Tyr Pro Gly Tyr Ser Tyr Asn Asn Trp Ala
165                 170                 175                 180 gcc aag ggc ctt aca tcc gcc tcc cta tcc acc aag agc ttc ccc ttc   1170
Ala Lys Gly Leu Thr Ser Ala Ser Leu Ser Thr Lys Ser Phe Pro Phe
            185                 190                 195 ttc aac tct atg aac gtc aac ccc ctg tca tca cag agc atg ttt tcc   1218
Phe Asn Ser Met Asn Val Asn Pro Leu Ser Ser Gln Ser Met Phe Ser
        200                 205                 210 cca ccc aac tct atc tcg tcc atg agc atg tcg agc agc atg gtg ccc   1266
Pro Pro Asn Ser Ile Ser Ser Met Ser Met Ser Ser Ser Met Val Pro
    215                 220                 225 tca gca gtg aca ggc gtc ccg ggc tcc agt ctc aac agc ctg aat aac   1314
Ser Ala Val Thr Gly Val Pro Gly Ser Ser Leu Asn Ser Leu Asn Asn
230                 235                 240 ttg aac aac ctg agt agc ccg tcg ctg aat tcc gcg gtg ccg acg cct   1362
Leu Asn Asn Leu Ser Ser Pro Ser Leu Asn Ser Ala Val Pro Thr Pro
245                 250                 255                 260 gcc tgt cct tac gcg ccg ccg act cct ccg tat gtt tat agg gac acg   1410
Ala Cys Pro Tyr Ala Pro Pro Thr Pro Pro Tyr Val Tyr Arg Asp Thr
            265                 270                 275 tgt aac tcg agc ctg gcc agc ctg aga ctg aaa gca aag cag cac tcc   1458
Cys Asn Ser Ser Leu Ala Ser Leu Arg Leu Lys Ala Lys Gln His Ser
        280                 285                 290 agc ttc ggc tac gcc agc gtg cag aac ccg gcc tcc aac ctg agt gct   1506
Ser Phe Gly Tyr Ala Ser Val Gln Asn Pro Ala Ser Asn Leu Ser Ala
    295                 300                 305 tgc cag tat gca gtg gac cgg ccc gtg tga gccgcaccca cagcgccggg     1556
Cys Gln Tyr Ala Val Asp Arg Pro Val
310                 315 atcctaggac cttgccggat ggggcaactc cgcccttgaa agactgggaa ttatgctaga  1616
```

-continued

```
aggtcgtggg cactaaagaa agggagagaa agagaagcta tatagagaaa aggaaaccac    1676
tgaatcaaag agagagctcc tttgatttca aagggatgtc ctcagtgtct gacatctttc    1736
actacaagta tttctaacag ttgcaaggac acatacacaa acaaatgttt gactggatat    1796
gacattttaa cattactata agcttgttat ttttttaagtt tagcattgtt aacatttaaa    1856
tgactgaaag gatgtatata tatcgaaatg tcaaattaat tttataaaag cagttgttag    1916
taatatcaca acagtgtttt taaaggttag gctttaaaat aaagcatgtt atacagaagc    1976
gattaggatt tttcgcttgc gagcaaggga gtgtatatac taaatgccac actgtatgtt    2036
tctaacatat tattattatt ataaaaaatg tgtgaatatc agttttagaa tagtttctct    2096
ggtggatgca atgatgtttc tgaaactgct atgtacaacc taccctgtgt ataacatttc    2156
gtacaatatt attgttttac ttttcagcaa atatgaaaca aatgtgtttt atttcatggg    2216
agtaaaatat actgcataca aaaaaaaaaa aaaa                                2250
```

<210> SEQ ID NO 10
<211> LENGTH: 317
<212> TYPE: PRT
<213> ORGANISM: Homo sapiens

<400> SEQUENCE: 10

```
Met Glu Thr Asn Cys Arg Lys Leu Val Ser Ala Cys Val Gln Leu Gly
1               5                   10                  15

Val Gln Pro Ala Ala Val Glu Cys Leu Phe Ser Lys Asp Ser Glu Ile
            20                  25                  30

Lys Lys Val Glu Phe Thr Asp Ser Pro Glu Ser Arg Lys Glu Ala Ala
        35                  40                  45

Ser Ser Lys Phe Phe Pro Arg Gln His Pro Gly Ala Asn Glu Lys Asp
    50                  55                  60

Lys Ser Gln Gln Gly Lys Asn Glu Asp Val Gly Ala Glu Asp Pro Ser
65                  70                  75                  80

Lys Lys Lys Arg Gln Arg Arg Gln Arg Thr His Phe Thr Ser Gln Gln
                85                  90                  95

Leu Gln Glu Leu Glu Ala Thr Phe Gln Arg Asn Arg Tyr Pro Asp Met
            100                 105                 110

Ser Thr Arg Glu Glu Ile Ala Val Trp Thr Asn Leu Thr Glu Ala Arg
        115                 120                 125

Val Arg Val Trp Phe Lys Asn Arg Arg Ala Lys Trp Arg Lys Arg Glu
    130                 135                 140

Arg Asn Gln Gln Ala Glu Leu Cys Lys Asn Gly Phe Gly Pro Gln Phe
145                 150                 155                 160

Asn Gly Leu Met Gln Pro Tyr Asp Asp Met Tyr Pro Gly Tyr Ser Tyr
                165                 170                 175

Asn Asn Trp Ala Ala Lys Gly Leu Thr Ser Ala Ser Leu Ser Thr Lys
            180                 185                 190

Ser Phe Pro Phe Phe Asn Ser Met Asn Val Asn Pro Leu Ser Ser Gln
        195                 200                 205

Ser Met Phe Ser Pro Pro Asn Ser Ile Ser Ser Met Ser Met Ser Ser
    210                 215                 220

Ser Met Val Pro Ser Ala Val Thr Gly Val Pro Gly Ser Ser Leu Asn
225                 230                 235                 240

Ser Leu Asn Asn Leu Asn Asn Leu Ser Ser Pro Ser Leu Asn Ser Ala
                245                 250                 255

Val Pro Thr Pro Ala Cys Pro Tyr Ala Pro Pro Thr Pro Pro Tyr Val
```

```
                  260                 265                 270
Tyr Arg Asp Thr Cys Asn Ser Ser Leu Ala Ser Leu Arg Leu Lys Ala
            275                 280                 285

Lys Gln His Ser Ser Phe Gly Tyr Ala Ser Val Gln Asn Pro Ala Ser
        290                 295                 300

Asn Leu Ser Ala Cys Gln Tyr Ala Val Asp Arg Pro Val
305                 310                 315

<210> SEQ ID NO 11
<211> LENGTH: 1903
<212> TYPE: DNA
<213> ORGANISM: Mus musculus
<220> FEATURE:
<221> NAME/KEY: CDS
<222> LOCATION: (256)..(1209)

<400> SEQUENCE: 11
gggaggggag agagagtgcg agaccgagag agaaagccgg agagcagcag acagaaactg    60
ccggcgcccg ctagctttag cagcccccg cgtggaccct ctcggaactt ggcaccctca   120
agatccccgc agttccaccc agacccgctc cacggcgctg gctgtgcagc ccgagcctcg   180
gccgcctggc agtcaccctg ggaagcggtg gacggggaca gccgttc tctctccggt     240
```

| | | | | | | | | | | | | |
|---|---|---|---|---|---|---|---|---|---|---|---|---|
| agccgataac cggga atg gag acc aat tgt cgc aaa cta gtg tcg gcc tgc | | | | | | | | | | | | 291 |
| | Met Glu Thr Asn Cys Arg Lys Leu Val Ser Ala Cys | | | | | | | | | | | |
| | 1 | | | 5 | | | | | 10 | | | |

```
gtg caa tta ggc gtg cag ccg gca gcc gtt gaa tgt ctc ttc tcc aaa   339
Val Gln Leu Gly Val Gln Pro Ala Ala Val Glu Cys Leu Phe Ser Lys
        15                  20                  25 gac tcc gaa atc aaa aag gtc gag ttc acg gac tct ccc aag agc cgg   387
Asp Ser Glu Ile Lys Lys Val Glu Phe Thr Asp Ser Pro Lys Ser Arg
 30                  35                  40 aaa gag tcg gcc agc agc aag ctg ttc ccg cgg cag cac ccc ggc gcc   435
Lys Glu Ser Ala Ser Ser Lys Leu Phe Pro Arg Gln His Pro Gly Ala
 45                  50                  55                  60 aat gag aaa gat aag ggc cag caa gga aag aat gag gat gtg ggc gcc   483
Asn Glu Lys Asp Lys Gly Gln Gln Gly Lys Asn Glu Asp Val Gly Ala
                 65                  70                  75 gag gac ccg tcc aag aag aag cgg caa cgc cgg cag agg act cat ttc   531
Glu Asp Pro Ser Lys Lys Lys Arg Gln Arg Arg Gln Arg Thr His Phe
             80                  85                  90 act agc cag cag ctg cag gag ctg gaa gcc act ttc cag aga aac cgc   579
Thr Ser Gln Gln Leu Gln Glu Leu Glu Ala Thr Phe Gln Arg Asn Arg
         95                 100                 105 tac cca gac atg tcc act cgc gaa gaa atc gcc gtg tgg acc aac ctt   627
Tyr Pro Asp Met Ser Thr Arg Glu Glu Ile Ala Val Trp Thr Asn Leu
    110                 115                 120 acg gaa gcc cga gtc cgg gtt tgg ttc aag aat cgc cgg gcc aaa tgg   675
Thr Glu Ala Arg Val Arg Val Trp Phe Lys Asn Arg Arg Ala Lys Trp
125                 130                 135                 140 aga aag cgg gaa cgc aac cag cag gcc gag ctg tgc aag aat ggc ttt   723
Arg Lys Arg Glu Arg Asn Gln Gln Ala Glu Leu Cys Lys Asn Gly Phe
                145                 150                 155 ggg ccg cag ttc aac ggg ctc atg cag ccc tac gat gac atg tac ccc   771
Gly Pro Gln Phe Asn Gly Leu Met Gln Pro Tyr Asp Asp Met Tyr Pro
            160                 165                 170 ggc tat tcg tac aac aat tgg gct gcc aag ggc ctc acg tca gcg tct   819
Gly Tyr Ser Tyr Asn Asn Trp Ala Ala Lys Gly Leu Thr Ser Ala Ser
        175                 180                 185 ctg tcc acc aag agc ttc ccc ttc ttc aac tcc atg aac gtc aat ccc   867
```

```
                    Leu Ser Thr Lys Ser Phe Pro Phe Phe Asn Ser Met Asn Val Asn Pro
                    190                 195                 200 ctg tcc tct cag agt atg ttt tcc ccg ccc aac tcc atc tca tct atg         915
Leu Ser Ser Gln Ser Met Phe Ser Pro Pro Asn Ser Ile Ser Ser Met
205                 210                 215                 220 agt atg tcg tcc agc atg gtg ccc tcc gcg gtg acc ggc gtc ccg ggc         963
Ser Met Ser Ser Ser Met Val Pro Ser Ala Val Thr Gly Val Pro Gly
                225                 230                 235 tcc agc ctc aat agc ctg aat aac ttg aac aac ctg agc agc ccg tcg        1011
Ser Ser Leu Asn Ser Leu Asn Asn Leu Asn Asn Leu Ser Ser Pro Ser
            240                 245                 250 ctg aat tcc gcg gtg ccc acg ccc gcc tgt cct tac gcg ccg ccg act        1059
Leu Asn Ser Ala Val Pro Thr Pro Ala Cys Pro Tyr Ala Pro Pro Thr
        255                 260                 265 cct ccg tac gtt tat agg gac aca tgt aac tcg agc ctg gcc agc ctg        1107
Pro Pro Tyr Val Tyr Arg Asp Thr Cys Asn Ser Ser Leu Ala Ser Leu
    270                 275                 280 aga ctg aaa gca aag cag cac tcc agc ttc ggc tac gcc agc gtg cag        1155
Arg Leu Lys Ala Lys Gln His Ser Ser Phe Gly Tyr Ala Ser Val Gln
285                 290                 295                 300 aac ccg gcc tcc aac ctg agt gct tgc cag tat gca gtc gac cgg ccg        1203
Asn Pro Ala Ser Asn Leu Ser Ala Cys Gln Tyr Ala Val Asp Arg Pro
                305                 310                 315 gtg tga accgcgccca gggcgcgggg atccgaggac tgtcggagtg gcaactctg          1259
Val ccccagaaag actgagaatt gtgctagaag gtcgtgcgca ctatgggaag gaagaggggg      1319
gaaaaaagat cagaggaaaa gaaaccactg aattcaaaga gagagcgcct ttgatttcaa      1379
aggaatgtcc ccaagtgtct acgtctttcg ctaagagtat tcccaacagt tggaggacgc      1439
gtacgcccac aaatgtttga ctggatatga cattttaaca ttactataag cttgttattt      1499
tttaagttta gcattgttaa cattaaaatg actgaaagga tgtatatata tcgaaatgtc      1559
aaattaattt tataaaagca gttgttagta ctatcacgac agtgttttta aaggctaggc      1619
tttaaaataa agcatgttat acagaatcag ttaggatttt tcgcttgcga gcaaaggaat      1679
gtatatacta aatgccacac tgtatgtttc taacatatta ttattataaa aatgtgtgaa      1739
tataagtttt agagtagttt ctctggtgga tgccttgttt ctgaaactgc tatgtacgac      1799
ccatcctgtg tataacattt cgtacgtatt tattgtttta cttttcagca aatatgaaaa      1859
aaaatgtgtt ttatttcttg ggagtaaaat atactgcata caaa                      1903

<210> SEQ ID NO 12
<211> LENGTH: 317
<212> TYPE: PRT
<213> ORGANISM: Mus musculus

<400> SEQUENCE: 12

Met Glu Thr Asn Cys Arg Lys Leu Val Ser Ala Cys Val Gln Leu Gly
1               5                   10                  15

Val Gln Pro Ala Ala Val Glu Cys Leu Phe Ser Lys Asp Ser Glu Ile
                20                  25                  30

Lys Lys Val Glu Phe Thr Asp Ser Pro Lys Ser Arg Lys Glu Ser Ala
            35                  40                  45

Ser Ser Lys Leu Phe Pro Arg Gln His Pro Gly Ala Asn Glu Lys Asp
        50                  55                  60

Lys Gly Gln Gln Gly Lys Asn Glu Asp Val Gly Ala Glu Asp Pro Ser
65                  70                  75                  80
```

```
Lys Lys Lys Arg Gln Arg Arg Gln Arg Thr His Phe Thr Ser Gln Gln
                85                  90                  95

Leu Gln Glu Leu Glu Ala Thr Phe Gln Arg Asn Arg Tyr Pro Asp Met
            100                 105                 110

Ser Thr Arg Glu Glu Ile Ala Val Trp Thr Asn Leu Thr Glu Ala Arg
        115                 120                 125

Val Arg Val Trp Phe Lys Asn Arg Arg Ala Lys Trp Arg Lys Arg Glu
    130                 135                 140

Arg Asn Gln Gln Ala Glu Leu Cys Lys Asn Gly Phe Gly Pro Gln Phe
145                 150                 155                 160

Asn Gly Leu Met Gln Pro Tyr Asp Asp Met Tyr Pro Gly Tyr Ser Tyr
                165                 170                 175

Asn Asn Trp Ala Ala Lys Gly Leu Thr Ser Ala Ser Leu Ser Thr Lys
            180                 185                 190

Ser Phe Pro Phe Phe Asn Ser Met Asn Val Asn Pro Leu Ser Ser Gln
        195                 200                 205

Ser Met Phe Ser Pro Pro Asn Ser Ile Ser Ser Met Ser Met Ser Ser
    210                 215                 220

Ser Met Val Pro Ser Ala Val Thr Gly Val Pro Gly Ser Ser Leu Asn
225                 230                 235                 240

Ser Leu Asn Asn Leu Asn Asn Leu Ser Ser Pro Ser Leu Asn Ser Ala
                245                 250                 255

Val Pro Thr Pro Ala Cys Pro Tyr Ala Pro Pro Thr Pro Pro Tyr Val
            260                 265                 270

Tyr Arg Asp Thr Cys Asn Ser Ser Leu Ala Ser Leu Arg Leu Lys Ala
        275                 280                 285

Lys Gln His Ser Ser Phe Gly Tyr Ala Ser Val Gln Asn Pro Ala Ser
    290                 295                 300

Asn Leu Ser Ala Cys Gln Tyr Ala Val Asp Arg Pro Val
305                 310                 315

<210> SEQ ID NO 13
<211> LENGTH: 1907
<212> TYPE: DNA
<213> ORGANISM: Homo sapiens
<220> FEATURE:
<221> NAME/KEY: CDS
<222> LOCATION: (56)..(1084)

<400> SEQUENCE: 13
acttgctctg cagctcccag aggtggtggt tgtgttacga aggctgaccc tgcca atg          58
                                                              Met
                                                               1 gcc gac aaa atg gtg cgc acc ccc aag tgc tcg aga tgc agg aac cat         106
Ala Asp Lys Met Val Arg Thr Pro Lys Cys Ser Arg Cys Arg Asn His
        5                  10                  15 ggc ttc ctg gtg ccc gtc aag gga cac gcg ggc aaa tgc cgc tgg aag         154
Gly Phe Leu Val Pro Val Lys Gly His Ala Gly Lys Cys Arg Trp Lys
     20                  25                  30 cag tgc ctc tgc gag aag tgc tac ctg atc tcc gag cgc cag aag atc         202
Gln Cys Leu Cys Glu Lys Cys Tyr Leu Ile Ser Glu Arg Gln Lys Ile
 35                  40                  45 atg gcc gcg cag aag gtg ctc aag acg cag gcc gcc gag gag gag cag         250
Met Ala Ala Gln Lys Val Leu Lys Thr Gln Ala Ala Glu Glu Glu Gln
 50                  55                  60                  65 gag gcg gcc ctg tgt gcg cag ggg ccc aag cag gcc tcc ggg gct gcg         298
Glu Ala Ala Leu Cys Ala Gln Gly Pro Lys Gln Ala Ser Gly Ala Ala
             70                  75                  80
```

```
gcc gcc gcc ccc gcc ccc gtc ccc gtc ccg gcc gcg agc ctc cgc ccg      346
Ala Ala Ala Pro Ala Pro Val Pro Val Pro Ala Ala Ser Leu Arg Pro
            85                  90                  95 ctg tcc ccg ggg act ccc tcc gga gac gcc gac ccg gga ccc gag ggc      394
Leu Ser Pro Gly Thr Pro Ser Gly Asp Ala Asp Pro Gly Pro Glu Gly
        100                 105                 110 cgc gcg gcc gct tgc ttc ttc gag cag ccc ccg cgg ggc cgg aac ccc      442
Arg Ala Ala Ala Cys Phe Phe Glu Gln Pro Pro Arg Gly Arg Asn Pro
    115                 120                 125 ggc ccg aga gcc ctc cag ccg gtt ctg ggc ggc cgc agc cac gtg gag      490
Gly Pro Arg Ala Leu Gln Pro Val Leu Gly Gly Arg Ser His Val Glu
130                 135                 140                 145 ccg agc gag cga gcc gcc gtg gcg atg ccc agc ctt gcg gga ccc cct      538
Pro Ser Glu Arg Ala Ala Val Ala Met Pro Ser Leu Ala Gly Pro Pro
                150                 155                 160 ttt ggg gcg gag gcc gca ggc agt ggc tac cct ggc ccc cta gac ctg      586
Phe Gly Ala Glu Ala Ala Gly Ser Gly Tyr Pro Gly Pro Leu Asp Leu
            165                 170                 175 cgc agg ccg atg cgg acc gtg ccc ggc cca ctg ttc acc gac ttt gtg      634
Arg Arg Pro Met Arg Thr Val Pro Gly Pro Leu Phe Thr Asp Phe Val
        180                 185                 190 cgc cct ctg aac atc aac ccg gac cgt gca ctg ggc cct gag tac cct      682
Arg Pro Leu Asn Ile Asn Pro Asp Arg Ala Leu Gly Pro Glu Tyr Pro
    195                 200                 205 ggt ggc tcc agc atg cac ccc tac tgc ccg ttc ccg ctg ggc tac ctg      730
Gly Gly Ser Ser Met His Pro Tyr Cys Pro Phe Pro Leu Gly Tyr Leu
210                 215                 220                 225 gac gcc cct cct ggc gtc ccc ctg cag cag ggc ttc cgg cat gtg tcc      778
Asp Ala Pro Pro Gly Val Pro Leu Gln Gln Gly Phe Arg His Val Ser
                230                 235                 240 cgc agc cag tac caa ggc gga ggc ttg gtg tca gaa cca gga gga gac      826
Arg Ser Gln Tyr Gln Gly Gly Gly Leu Val Ser Glu Pro Gly Gly Asp
            245                 250                 255 ttc cag cca agc tac tac ctg ccg ccg ccg ccg cca ctg ccg ccc          874
Phe Gln Pro Ser Tyr Tyr Leu Pro Pro Pro Pro Pro Leu Pro Pro
        260                 265                 270 ctt cca ccg ctt cca ccg cag ccc cag ttc ctc ccg cca ggc tac ctc      922
Leu Pro Pro Leu Pro Pro Gln Pro Gln Phe Leu Pro Pro Gly Tyr Leu
    275                 280                 285 tct gcg ctc cac ttc ctc ccc ccg cca ccg cca cca cct cca tca          970
Ser Ala Leu His Phe Leu Pro Pro Pro Pro Pro Pro Pro Pro Ser
290                 295                 300                 305 tct ttc tca ctg acc gtc ctg ttt gat act gac aag gag aac act gat     1018
Ser Phe Ser Leu Thr Val Leu Phe Asp Thr Asp Lys Glu Asn Thr Asp
                310                 315                 320 gac cag gat gca gag gta ctg tcg ggt gag ccc agc cag cca tcg tct     1066
Asp Gln Asp Ala Glu Val Leu Ser Gly Glu Pro Ser Gln Pro Ser Ser
            325                 330                 335 cag gag cag tcc gac tag gccccaggcc cgccctcctg gccagcagag            1114
Gln Glu Gln Ser Asp
        340 tggggcactg gggggcaaca gcaacagttt tcctgtcttc attcagtgat atgtagggag   1174 gaaggaggtt gatagcatag atggcaactg attcccagtt taagatagga ggaaggagag   1234 caatttctaa gtttcaatcc tgcgctgtac agttgaagaa gagtgtggag gaagctatta   1294 ccaggggagg gccagggctc tgaggagtgg gcgctgggag aagctcccat ttaggaatga   1354 atttaactgt ccttgggtta cactaccatt tattggaaca agcccagag gcagtatttg    1414
```

-continued

```
atttcctcag gccccactct aggacaggag gcaccatcta tttcagcctt ctgctgcctt    1474
tgcctggtcc tccaggttgc tgggggcacc acagacatca agattccagt tcatccaggt    1534
ggctggagcc agcagccagg accagggtcg ttgacagcag gttctgcagc atcctgcctt    1594
gctgctctgt cccccacatc ttcctggcca cagcccttg ccctcctct aagggtttt       1654 actagcaagc atcctggctg ctggggctac ttcattcccc ctccataaag tttcagccat    1714
tatgggcact ggttttaaaa aatttattag tttgactatt tgatggtttt atagtgattg    1774
ccaactttaa aaagtaggct gttcataagc actgatgcag tccctaggga atagaatggt    1834
gcttctgatc acctgtgaca tgaacagttt cttctgtgag gacagttggc tattgaaata    1894
aaatgagcaa tgg                                                       1907
```

<210> SEQ ID NO 14
<211> LENGTH: 342
<212> TYPE: PRT
<213> ORGANISM: Homo sapiens

<400> SEQUENCE: 14

```
Met Ala Asp Lys Met Val Arg Thr Pro Lys Cys Ser Arg Cys Arg Asn
1               5                   10                  15

His Gly Phe Leu Val Pro Val Lys Gly His Ala Gly Lys Cys Arg Trp
            20                  25                  30

Lys Gln Cys Leu Cys Glu Lys Cys Tyr Leu Ile Ser Glu Arg Gln Lys
        35                  40                  45

Ile Met Ala Ala Gln Lys Val Leu Lys Thr Gln Ala Ala Glu Glu Glu
    50                  55                  60

Gln Glu Ala Ala Leu Cys Ala Gln Gly Pro Lys Gln Ala Ser Gly Ala
65                  70                  75                  80

Ala Ala Ala Pro Ala Pro Val Pro Val Pro Ala Ala Ser Leu Arg
                85                  90                  95

Pro Leu Ser Pro Gly Thr Pro Ser Gly Asp Ala Asp Pro Gly Pro Glu
            100                 105                 110

Gly Arg Ala Ala Ala Cys Phe Phe Glu Gln Pro Pro Arg Gly Arg Asn
        115                 120                 125

Pro Gly Pro Arg Ala Leu Gln Pro Val Leu Gly Gly Arg Ser His Val
    130                 135                 140

Glu Pro Ser Glu Arg Ala Ala Val Ala Met Pro Ser Leu Ala Gly Pro
145                 150                 155                 160

Pro Phe Gly Ala Glu Ala Ala Gly Ser Gly Tyr Pro Gly Pro Leu Asp
                165                 170                 175

Leu Arg Arg Pro Met Arg Thr Val Pro Gly Pro Leu Phe Thr Asp Phe
            180                 185                 190

Val Arg Pro Leu Asn Ile Asn Pro Asp Arg Ala Leu Gly Pro Glu Tyr
        195                 200                 205

Pro Gly Gly Ser Ser Met His Pro Tyr Cys Pro Phe Pro Leu Gly Tyr
    210                 215                 220

Leu Asp Ala Pro Pro Gly Val Pro Leu Gln Gln Gly Phe Arg His Val
225                 230                 235                 240

Ser Arg Ser Gln Tyr Gln Gly Gly Leu Val Ser Glu Pro Gly Gly
                245                 250                 255

Asp Phe Gln Pro Ser Tyr Tyr Leu Pro Pro Pro Pro Pro Leu Pro
            260                 265                 270

Pro Leu Pro Pro Leu Pro Gln Pro Gln Phe Leu Pro Pro Gly Tyr
        275                 280                 285
```

```
Leu Ser Ala Leu His Phe Leu Pro Pro Pro Pro Pro Pro Pro
    290             295                 300

Ser Ser Phe Ser Leu Thr Val Leu Phe Asp Thr Asp Lys Glu Asn Thr
305             310                 315                 320

Asp Asp Gln Asp Ala Glu Val Leu Ser Gly Glu Pro Ser Gln Pro Ser
                325                 330                 335

Ser Gln Glu Gln Ser Asp
            340

<210> SEQ ID NO 15
<211> LENGTH: 1790
<212> TYPE: DNA
<213> ORGANISM: Mus musculus
<220> FEATURE:
<221> NAME/KEY: CDS
<222> LOCATION: (1)..(1080)

<400> SEQUENCE: 15 atg ctt cgc gcc ccc aag tgc tct agg tgc cgg aac cat ggc tat ctg      48
Met Leu Arg Ala Pro Lys Cys Ser Arg Cys Arg Asn His Gly Tyr Leu
1               5                   10                  15 gta cca gtc aag ggc cat acg ggc aaa tgc cgc tgg aag cag tgc atc      96
Val Pro Val Lys Gly His Thr Gly Lys Cys Arg Trp Lys Gln Cys Ile
                20                  25                  30 tgt gac aag tgc tac ctg atc acc gag cgc cag aag atc atg gct gcc     144
Cys Asp Lys Cys Tyr Leu Ile Thr Glu Arg Gln Lys Ile Met Ala Ala
            35                  40                  45 cag aag gtt ctc aga acc caa gct gcc gag gag cag gtg gcg acc gtg     192
Gln Lys Val Leu Arg Thr Gln Ala Ala Glu Glu Gln Val Ala Thr Val
        50                  55                  60 ggc acg cag ggt ccc cag ctg cct cct agg gct cca gca gcg gcg gcc     240
Gly Thr Gln Gly Pro Gln Leu Pro Pro Arg Ala Pro Ala Ala Ala Ala
65                  70                  75                  80 acc gcc ttg agc tcc agc att tgc cca ctg cct agg gcg gtt ccg gga     288
Thr Ala Leu Ser Ser Ser Ile Cys Pro Leu Pro Arg Ala Val Pro Gly
                85                  90                  95 ggc gtt ggg cca ggc ccc acg gcc act tgc ttc ctc gag agg ccc ccg     336
Gly Val Gly Pro Gly Pro Thr Ala Thr Cys Phe Leu Glu Arg Pro Pro
            100                 105                 110 cag gcc ccg agc cca ggc ccg agc acc ttc cag ctg ggc cca agt ggc     384
Gln Ala Pro Ser Pro Gly Pro Ser Thr Phe Gln Leu Gly Pro Ser Gly
        115                 120                 125 cgc ccg ggc ccc agc acc ttc cag cct gga cca ggg gcc ccc ggg gga     432
Arg Pro Gly Pro Ser Thr Phe Gln Pro Gly Pro Gly Ala Pro Gly Gly
    130                 135                 140 ctg cgc gac cgt tcc tcc gcg tgg ctg ccc cag ctc atg cca cag gcg     480
Leu Arg Asp Arg Ser Ser Ala Trp Leu Pro Gln Leu Met Pro Gln Ala
145                 150                 155                 160 ccc agg ccg gag ctt tgc tac ccg gat cag cac ctg cca gtg cgg ccc     528
Pro Arg Pro Glu Leu Cys Tyr Pro Asp Gln His Leu Pro Val Arg Pro
                165                 170                 175 gtg cca gtg cca ggg cca gtg cgg ccc gtg ccc cga ctg ccg ttc gcc     576
Val Pro Val Pro Gly Pro Val Arg Pro Val Pro Arg Leu Pro Phe Ala
            180                 185                 190 gac tac ggg cat cct ctg aga ttc aag tct gat cat gtg gta gga gct     624
Asp Tyr Gly His Pro Leu Arg Phe Lys Ser Asp His Val Val Gly Ala
        195                 200                 205 ggg aat cct gag aga gag ccg ttc aag cag tgc cct gcc tgc gtc cct     672
Gly Asn Pro Glu Arg Glu Pro Phe Lys Gln Cys Pro Ala Cys Val Pro
    210                 215                 220
```

```
gtt tca ccc tac cag tcc ttt cca ctt tcg gaa ggc cag gat tca tcc    720
Val Ser Pro Tyr Gln Ser Phe Pro Leu Ser Glu Gly Gln Asp Ser Ser
225                 230                 235                 240 tct gct ctg ggg gtc cct caa caa aga ggc ttc cgg cat gtc tcc tgc    768
Ser Ala Leu Gly Val Pro Gln Gln Arg Gly Phe Arg His Val Ser Cys
                245                 250                 255 agc ccc tac cat aga agc ggc ttg gtg tca gag cca gcc aga gac ctg    816
Ser Pro Tyr His Arg Ser Gly Leu Val Ser Glu Pro Ala Arg Asp Leu
            260                 265                 270 cag cca acc tac tgc tca ccg ccg ccg cca ccg ccg cca cct ccg        864
Gln Pro Thr Tyr Cys Ser Pro Pro Pro Pro Pro Pro Pro Pro Pro
        275                 280                 285 cca cca cta cca gca ccc cca ccc cag cca cag cag ccc cac ttc ctc    912
Pro Pro Leu Pro Ala Pro Pro Pro Gln Pro Gln Gln Pro His Phe Leu
    290                 295                 300 cca cca ggc tac ctc tct gct ctc cac ttc ctg cca ccg ccg cca ccg    960
Pro Pro Gly Tyr Leu Ser Ala Leu His Phe Leu Pro Pro Pro Pro Pro
305                 310                 315                 320 cca cca tct cca cca tct ttc tcg ctg acc tac gat aca gac aag gag    1008
Pro Pro Ser Pro Pro Ser Phe Ser Leu Thr Tyr Asp Thr Asp Lys Glu
                325                 330                 335 aat acc aat gac cag gat gca gaa gca ccc acc gag ccc agc cag gac    1056
Asn Thr Asn Asp Gln Asp Ala Glu Ala Pro Thr Glu Pro Ser Gln Asp
            340                 345                 350 tct ccc cag gag cag tcc aac taa gctgcaggcc acctggaagg ccaccgggtg   1110
Ser Pro Gln Glu Gln Ser Asn
        355 gggacgggca tagatggcgg gggttatttt ttcaccatgt tcatgttata taggagaaag   1170 gatactgata ggtgtaagaa ggcagcgaat tcctactcca ggttagaagg cacaggtgg    1230 tttccaaggt tctctgggtc ctgggtgggt gttgaagtgg tgtacaaagg gagagaaagt   1290 ctgggatggg cagggctttt gaagagtggg ggctggtgaa acacaagttt agaaatgaat   1350 ttaaccatct gagccatgta tgaaattcac ttctagaggt ggcccctgat ttccccaagc   1410 ctcactcagg acagaaggca ccattcagtt cagccttctg cccccttgc ctgaccccca    1470 agcctgggta ccgcaaacac caaggcctcc agacagtgca gggcaggtgc cagggcctga   1530 gatgctgaca gcaggttctg cagcatccac ctttgcccaa cactgcctct cgtcctcttc   1590 cagagagtga gcgtcctgac aactgagcca cttcacttcc ctgggaaact caagcatagg   1650 tgtcctttct catttaaaaa tgtagatttt agcatttgat gttcttatgg tggggaactc   1710 atgggcactg cagcagttct cggagcaaaa aaaatggcca tttgttctct ggggacagta   1770 ttaaataaag tgagcattag                                               1790

<210> SEQ ID NO 16
<211> LENGTH: 359
<212> TYPE: PRT
<213> ORGANISM: Mus musculus

<400> SEQUENCE: 16

Met Leu Arg Ala Pro Lys Cys Ser Arg Cys Arg Asn His Gly Tyr Leu
1               5                   10                  15

Val Pro Val Lys Gly His Thr Gly Lys Cys Arg Trp Lys Gln Cys Ile
                20                  25                  30

Cys Asp Lys Cys Tyr Leu Ile Thr Glu Arg Gln Lys Ile Met Ala Ala
            35                  40                  45

Gln Lys Val Leu Arg Thr Gln Ala Ala Glu Glu Gln Val Ala Thr Val
```

```
            50                  55                  60
Gly Thr Gln Gly Pro Gln Leu Pro Pro Arg Ala Pro Ala Ala Ala
 65                  70                  75                  80

Thr Ala Leu Ser Ser Ser Ile Cys Pro Leu Pro Arg Ala Val Pro Gly
                 85                  90                  95

Gly Val Gly Pro Gly Pro Thr Ala Thr Cys Phe Leu Glu Arg Pro Pro
            100                 105                 110

Gln Ala Pro Ser Pro Gly Pro Ser Thr Phe Gln Leu Gly Pro Ser Gly
            115                 120                 125

Arg Pro Gly Pro Ser Thr Phe Gln Pro Gly Pro Gly Ala Pro Gly Gly
        130                 135                 140

Leu Arg Asp Arg Ser Ser Ala Trp Leu Pro Gln Leu Met Pro Gln Ala
145                 150                 155                 160

Pro Arg Pro Glu Leu Cys Tyr Pro Asp Gln His Leu Pro Val Arg Pro
                165                 170                 175

Val Pro Val Pro Gly Pro Val Arg Pro Val Pro Arg Leu Pro Phe Ala
            180                 185                 190

Asp Tyr Gly His Pro Leu Arg Phe Lys Ser Asp His Val Val Gly Ala
            195                 200                 205

Gly Asn Pro Glu Arg Glu Pro Phe Lys Gln Cys Pro Ala Cys Val Pro
        210                 215                 220

Val Ser Pro Tyr Gln Ser Phe Pro Leu Ser Glu Gly Gln Asp Ser Ser
225                 230                 235                 240

Ser Ala Leu Gly Val Pro Gln Gln Arg Gly Phe Arg His Val Ser Cys
                245                 250                 255

Ser Pro Tyr His Arg Ser Gly Leu Val Ser Glu Pro Ala Arg Asp Leu
            260                 265                 270

Gln Pro Thr Tyr Cys Ser Pro Pro Pro Pro Pro Pro Pro Pro Pro Pro
        275                 280                 285

Pro Pro Leu Pro Ala Pro Pro Gln Pro Gln Gln Pro His Phe Leu
290                 295                 300

Pro Pro Gly Tyr Leu Ser Ala Leu His Phe Leu Pro Pro Pro Pro
305                 310                 315                 320

Pro Pro Ser Pro Pro Ser Phe Ser Leu Thr Tyr Asp Thr Asp Lys Glu
            325                 330                 335

Asn Thr Asn Asp Gln Asp Ala Glu Ala Pro Thr Glu Pro Ser Gln Asp
            340                 345                 350

Ser Pro Gln Glu Gln Ser Asn
        355

<210> SEQ ID NO 17
<211> LENGTH: 34
<212> TYPE: DNA
<213> ORGANISM: Bacteriophage P1

<400> SEQUENCE: 17
ataacttcgt atagcataca ttatacgaag ttat                              34

<210> SEQ ID NO 18
<211> LENGTH: 34
<212> TYPE: DNA
<213> ORGANISM: Artificial Sequence
<220> FEATURE:
<223> OTHER INFORMATION: Synthetic mutant loxP (lox71) sequence

<400> SEQUENCE: 18
```

```
taccgttcgt atagcataca ttatacgaag ttat                    34

<210> SEQ ID NO 19
<211> LENGTH: 34
<212> TYPE: DNA
<213> ORGANISM: Artificial Sequence
<220> FEATURE:
<223> OTHER INFORMATION: Synthetic mutant loxP (lox66) sequence

<400> SEQUENCE: 19
ataacttcgt atagcataca ttatacgaac ggta                    34
```